(12) United States Patent
Dugi et al.

(10) Patent No.: US 8,551,957 B2
(45) Date of Patent: Oct. 8, 2013

(54) PHARMACEUTICAL COMPOSITION COMPRISING A GLUCOPYRANOSYL-SUBSTITUTED BENZENE DERIVATE

(75) Inventors: Klaus Dugi, Dresden (DE); Michael Mark, Biberach (DE); Leo Thomas, Biberach (DE); Frank Himmelsbach, Mittelbiberach (DE)

(73) Assignee: Boehringer Ingelheim International GmbH, Ingelheim Am Rhein (DE)

( * ) Notice: Subject to any disclaimer, the term of this patent is extended or adjusted under 35 U.S.C. 154(b) by 230 days.

(21) Appl. No.: 12/673,327

(22) PCT Filed: Aug. 15, 2008

(86) PCT No.: PCT/EP2008/060736
§ 371 (c)(1),
(2), (4) Date: Apr. 15, 2010

(87) PCT Pub. No.: WO2009/022007
PCT Pub. Date: Feb. 19, 2009

(65) Prior Publication Data
US 2011/0195917 A1    Aug. 11, 2011

(30) Foreign Application Priority Data
Aug. 16, 2007 (EP) .................. 07114459

(51) Int. Cl.
*A01N 43/04* (2006.01)
*A61K 31/70* (2006.01)
*C07H 1/00* (2006.01)

(52) U.S. Cl.
USPC .......................... 514/23; 536/1.11

(58) Field of Classification Search
None
See application file for complete search history.

(56) References Cited

U.S. PATENT DOCUMENTS

| | | |
|---|---|---|
| 3,174,901 A | 3/1965 | Sterne |
| 3,884,906 A | 5/1975 | Van Der Meer et al. |
| 4,379,785 A | 4/1983 | Weyer et al. |
| 4,602,023 A | 7/1986 | Kiely et al. |
| 4,639,436 A | 1/1987 | Junge et al. |
| 4,786,023 A | 11/1988 | Harris et al. |
| 4,786,755 A | 11/1988 | Kiely et al. |
| 6,303,661 B1 | 10/2001 | Demuth et al. |
| 6,414,126 B1 | 7/2002 | Ellsworth et al. |
| 6,515,117 B2 | 2/2003 | Ellsworth et al. |
| 6,613,806 B1 | 9/2003 | Aven et al. |
| 6,627,611 B2 | 9/2003 | Tomiyama et al. |
| 6,774,112 B2 | 8/2004 | Gougoutas |
| 6,794,480 B2 | 9/2004 | Goto et al. |
| 6,890,898 B2 | 5/2005 | Bachovchin et al. |
| 6,936,590 B2 | 8/2005 | Washburn et al. |
| 6,972,283 B2 | 12/2005 | Fujikura et al. |
| 7,109,192 B2 | 9/2006 | Hauel et al. |
| 7,169,761 B2 | 1/2007 | Tomiyama et al. |
| 7,173,028 B2 | 2/2007 | Dahmann et al. |
| 7,202,350 B2 | 4/2007 | Imamura et al. |
| 7,371,732 B2 | 5/2008 | Eickelmann et al. |
| 7,375,087 B2 | 5/2008 | Teranishi et al. |
| 7,375,090 B2 | 5/2008 | Himmelsbach et al. |
| 7,375,213 B2 | 5/2008 | Deshpande et al. |
| 7,393,836 B2 | 7/2008 | Eckhardt et al. |
| 7,407,955 B2* | 8/2008 | Himmelsbach et al. ... 514/234.2 |
| 7,417,032 B2 | 8/2008 | Eckhardt et al. |
| 7,419,959 B2 | 9/2008 | Eckhardt et al. |
| 7,482,337 B2 | 1/2009 | Himmelsbach et al. |
| 7,501,426 B2 | 3/2009 | Himmelsbach et al. |
| 7,541,341 B2 | 6/2009 | Fushimi et al. |
| 7,579,449 B2* | 8/2009 | Eckhardt et al. ............. 536/1.11 |
| 7,589,193 B2* | 9/2009 | Washburn et al. ............ 536/122 |
| 7,662,790 B2 | 2/2010 | Himmelsbach et al. |
| 7,674,486 B2 | 3/2010 | Bhaskaran et al. |
| 7,683,160 B2 | 3/2010 | Eckhardt et al. |
| 7,687,469 B2 | 3/2010 | Eckhardt et al. |
| 7,713,938 B2 | 5/2010 | Himmelsbach et al. |
| 7,723,309 B2 | 5/2010 | Himmelsbach et al. |
| 7,745,414 B2 | 6/2010 | Eckhardt et al. |
| 7,772,191 B2 | 8/2010 | Eckhardt et al. |
| 7,772,192 B2 | 8/2010 | Esko |
| 7,772,378 B2 | 8/2010 | Himmelsbach et al. |
| 7,772,407 B2 | 8/2010 | Imamura et al. |
| 7,776,830 B2 | 8/2010 | Eckhardt et al. |
| 7,820,815 B2 | 10/2010 | Boehringer et al. |
| 7,847,074 B2 | 12/2010 | Eckhardt et al. |
| 7,851,502 B2 | 12/2010 | Bindra et al. |
| 7,851,602 B2 | 12/2010 | Himmelsbach et al. |
| 7,858,587 B2 | 12/2010 | Eckhardt et al. |
| 7,879,806 B2 | 2/2011 | Himmelsbach et al. |
| 7,879,807 B2 | 2/2011 | Himmelsbach et al. |
| 8,039,441 B2 | 10/2011 | Himmelsbach et al. |
| 8,071,583 B2* | 12/2011 | Himmelsbach .......... 514/210.21 |
| 8,106,060 B2 | 1/2012 | Pfrengle et al. |

(Continued)

FOREIGN PATENT DOCUMENTS

| | | |
|---|---|---|
| CA | 2382480 A1 | 3/2001 |
| CA | 2388818 A1 | 4/2001 |

(Continued)

OTHER PUBLICATIONS

Adachi et al., Metabolism, vol. 49, No. 8, 2000, 990-995.*

(Continued)

*Primary Examiner* — Traviss C McIntosh, III
(74) *Attorney, Agent, or Firm* — Michael P. Morris; Edouard G. Lebel

(57) ABSTRACT

The invention relates to a pharmaceutical composition according to the claim 1 comprising a glucopyranosyl-substituted benzene derivative in combination with a DPP IV inhibitor which is suitable in the treatment or prevention of one or more conditions selected from type 1 diabetes mellitus, type 2 diabetes mellitus, impaired glucose tolerance and hyperglycemia. In addition the present invention relates to methods for preventing or treating of metabolic disorders and related conditions.

48 Claims, 2 Drawing Sheets

(56) References Cited

U.S. PATENT DOCUMENTS

Figure 1:
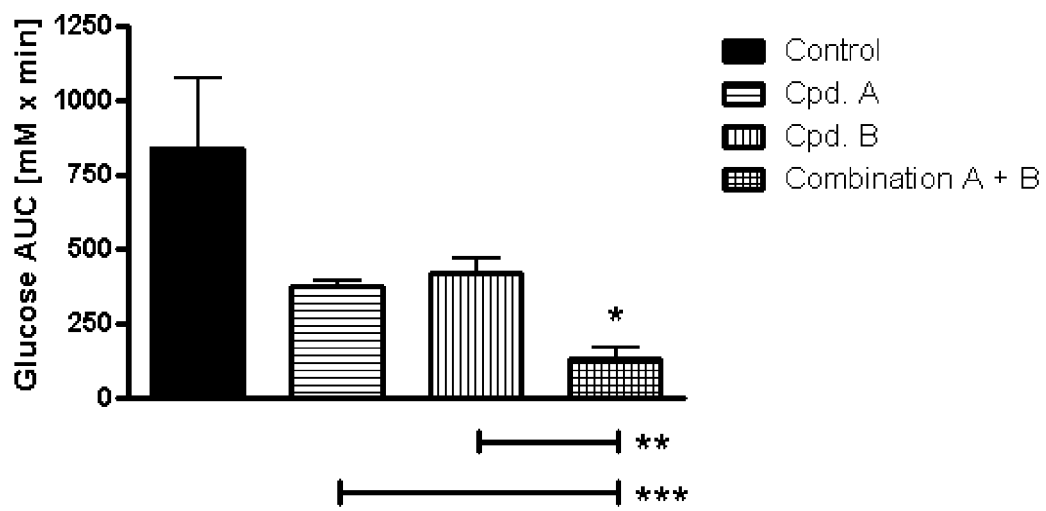

| | | |
|---|---|---|
| 8,119,648 B2 | 2/2012 | Himmelsbach et al. |
| 8,178,541 B2 | 5/2012 | Himmelsbach et al. |
| 8,232,281 B2 | 7/2012 | Dugi et al. |
| 8,283,326 B2 | 10/2012 | Eckhardt et al. |
| 2002/0137903 A1 | 9/2002 | Ellsworth et al. |
| 2002/0198205 A1 | 12/2002 | Himmelsbach et al. |
| 2003/0064935 A1 | 4/2003 | Gougoutas |
| 2003/0087843 A1 | 5/2003 | Washburn |
| 2003/0105077 A1 | 6/2003 | Kanstrup et al. |
| 2003/0114390 A1 | 6/2003 | Washburn et al. |
| 2004/0087587 A1 | 5/2004 | Himmelsbach et al. |
| 2004/0097510 A1 | 5/2004 | Himmelsbach et al. |
| 2004/0138148 A1 | 7/2004 | Fushimi et al. |
| 2004/0138439 A1 | 7/2004 | Deshpande et al. |
| 2004/0180925 A1 | 9/2004 | Matsuno et al. |
| 2005/0065098 A1 | 3/2005 | Fujikura et al. |
| 2005/0085680 A1 | 4/2005 | Auerbach et al. |
| 2005/0124555 A1 | 6/2005 | Tomiyama et al. |
| 2005/0130985 A1 | 6/2005 | Himmelsbach et al. |
| 2005/0187168 A1 | 8/2005 | Eickelmann et al. |
| 2005/0209166 A1 | 9/2005 | Eckhardt et al. |
| 2005/0233982 A1 | 10/2005 | Himmelsbach et al. |
| 2005/0234108 A1 | 10/2005 | Himmelsbach et al. |
| 2005/0256310 A1 | 11/2005 | Hulin et al. |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0079541 A1 | 4/2006 | Langkopf et al. |
| 2006/0142210 A1 | 6/2006 | Eckhardt et al. |
| 2006/0142310 A1 | 6/2006 | Pfrengle et al. |
| 2006/0154866 A1 | 7/2006 | Chu et al. |
| 2006/0189548 A1 | 8/2006 | Himmelsbach et al. |
| 2006/0205711 A1 | 9/2006 | Himmelsbach et al. |
| 2006/0210627 A1 | 9/2006 | Pfeffer et al. |
| 2006/0234953 A1 | 10/2006 | Himmelsbach et al. |
| 2006/0247226 A1 | 11/2006 | Himmelsbach et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0027168 A1 | 2/2007 | Pfrengle et al. |
| 2007/0049537 A1 | 3/2007 | Eckhardt et al. |
| 2007/0054867 A1 | 3/2007 | Eckhardt et al. |
| 2007/0060530 A1 | 3/2007 | Christopher et al. |
| 2007/0072813 A1 | 3/2007 | Himmelsbach et al. |
| 2007/0073046 A1 | 3/2007 | Eckhardt et al. |
| 2007/0249544 A1 | 10/2007 | Himmelsbach et al. |
| 2007/0259821 A1 | 11/2007 | Eckhardt et al. |
| 2007/0259900 A1 | 11/2007 | Sieger et al. |
| 2007/0281940 A1 | 12/2007 | Dugi et al. |
| 2007/0293690 A1 | 12/2007 | Tomiyama et al. |
| 2007/0299076 A1 | 12/2007 | Piotrowski et al. |
| 2008/0058379 A1 | 3/2008 | Eckhardt et al. |
| 2008/0107731 A1 | 5/2008 | Kohlrausch et al. |
| 2008/0108816 A1 | 5/2008 | Zutter |
| 2008/0207882 A1 | 8/2008 | Derdau et al. |
| 2008/0234367 A1 | 9/2008 | Washburn et al. |
| 2008/0249089 A1 | 10/2008 | Himmelsbach et al. |
| 2008/0255159 A1 | 10/2008 | Himmelsbach et al. |
| 2008/0287529 A1 | 11/2008 | Deshpande et al. |
| 2009/0023913 A1 | 1/2009 | Eckhardt et al. |
| 2009/0137801 A1 | 5/2009 | Himmelsbach et al. |
| 2009/0192314 A1 | 7/2009 | Pfrengle et al. |
| 2009/0318547 A1 | 12/2009 | Eckhardt et al. |
| 2009/0326215 A1 | 12/2009 | Eckhardt et al. |
| 2010/0069310 A1 | 3/2010 | Himmelsbach et al. |
| 2010/0074950 A1 | 3/2010 | Sesha |
| 2010/0081625 A1 | 4/2010 | Wienrich et al. |
| 2010/0093654 A1 | 4/2010 | Himmelsbach et al. |
| 2010/0099641 A1 | 4/2010 | Himmelsbach et al. |
| 2010/0173916 A1 | 7/2010 | Himmelsbach et al. |
| 2010/0179191 A1 | 7/2010 | Himmelsbach et al. |
| 2010/0204250 A1 | 8/2010 | Himmelsbach et al. |
| 2010/0209506 A1 | 8/2010 | Eisenreich |
| 2010/0210662 A1 | 8/2010 | Baroni et al. |
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0317847 A1 | 12/2010 | Eckhardt et al. |
| 2011/0014284 A1 | 1/2011 | Eisenreich et al. |
| 2011/0046076 A1 | 2/2011 | Eickelmann et al. |
| 2011/0046087 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0178033 A1 | 7/2011 | Eckhardt et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0236477 A1 | 9/2011 | Schneider et al. |
| 2011/0237526 A1 | 9/2011 | Weber et al. |
| 2011/0237532 A1 | 9/2011 | De Vries et al. |
| 2011/0237789 A1 | 9/2011 | Weber et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0071403 A1 | 3/2012 | Strumph et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0196812 A1 | 8/2012 | Eickelmann et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0283169 A1 | 11/2012 | Grempler et al. |
| 2012/0296080 A1 | 11/2012 | Eckhardt et al. |
| 2012/0296091 A1 | 11/2012 | Sieger et al. |
| 2013/0035281 A1 | 2/2013 | Klein et al. |
| 2013/0035298 A1 | 2/2013 | Broedl et al. |
| 2013/0064887 A1 | 3/2013 | Ito et al. |
| 2013/0096076 A1 | 4/2013 | Dugi et al. |

FOREIGN PATENT DOCUMENTS

| | | |
|---|---|---|
| CA | 2437240 A1 | 8/2002 |
| CA | 2435730 A1 | 9/2002 |
| CA | 2463989 A1 | 4/2003 |
| CA | 2494177 A1 | 2/2004 |
| CA | 2496249 A1 | 3/2004 |
| CA | 2505389 A1 | 5/2004 |
| CA | 2470365 A1 | 6/2004 |
| CA | 2508024 A1 | 6/2004 |
| CA | 2508226 A1 | 6/2004 |
| CA | 2508233 A1 | 6/2004 |
| CA | 2526145 A1 | 9/2004 |
| CA | 2539032 A1 | 3/2005 |
| CA | 2544480 A1 | 6/2005 |
| CA | 2548353 A1 | 7/2005 |
| CA | 2555050 A1 | 9/2005 |
| CA | 2557269 A1 | 9/2005 |
| CA | 2557320 A1 | 9/2005 |
| CA | 2557801 A1 | 10/2005 |
| CA | 2569915 A1 | 1/2006 |
| CA | 2572149 A1 | 1/2006 |
| CA | 2572819 A1 | 1/2006 |
| CA | 2573777 A1 | 2/2006 |
| CA | 2574451 A1 | 2/2006 |
| CA | 2576294 A1 | 3/2006 |
| CA | 2574500 A1 | 4/2006 |
| CA | 2586938 A1 | 5/2006 |
| CA | 2617090 A1 | 2/2007 |

| | | | | | | |
|---|---|---|---|---|---|---|
| CA | 2649922 A1 | 11/2007 | | WO | 2005000848 A1 | 1/2005 |
| CA | 2651019 A1 | 11/2007 | | WO | 2005012318 A1 | 2/2005 |
| CA | 2651089 A1 | 11/2007 | | WO | 2005012326 A1 | 2/2005 |
| CA | 2696579 A1 | 2/2009 | | WO | 2005021566 A2 | 3/2005 |
| CA | 2720450 A1 | 10/2009 | | WO | 2005049022 A2 | 6/2005 |
| CA | 2726244 A1 | 12/2009 | | WO | 2005051950 A1 | 6/2005 |
| CA | 2732803 A1 | 2/2010 | | WO | 2005063785 A2 | 7/2005 |
| CA | 2735562 A1 | 2/2010 | | WO | 2005085237 A1 | 9/2005 |
| CA | 2736421 A1 | 3/2010 | | WO | 2005085246 A1 | 9/2005 |
| CA | 2738367 A1 | 4/2010 | | WO | 2005085265 A1 | 9/2005 |
| CA | 2745037 A1 | 7/2010 | | WO | 2005092877 A1 | 10/2005 |
| CA | 2745039 A1 | 7/2010 | | WO | 2005116014 A1 | 12/2005 |
| CA | 2750798 A1 | 8/2010 | | WO | 2005117861 A1 | 12/2005 |
| CA | 2752437 A1 | 8/2010 | | WO | 2006002912 A1 | 1/2006 |
| CA | 2776296 A1 | 4/2011 | | WO | 2006005613 A1 | 1/2006 |
| CA | 2782179 A1 | 6/2011 | | WO | 2006006496 A1 | 1/2006 |
| CN | 101234105 A | 8/2008 | | WO | 2006008038 A1 | 1/2006 |
| DE | 2758025 A1 | 7/1979 | | WO | 2006010557 A1 | 2/2006 |
| DE | 2951135 A1 | 6/1981 | | WO | 2006011469 A1 | 2/2006 |
| DE | 102004044221 A1 | 3/2006 | | WO | 2006018150 A1 | 2/2006 |
| EP | 0206567 A2 | 12/1986 | | WO | 2006029769 A1 | 3/2006 |
| EP | 1224195 B | 7/2002 | | WO | 2006034489 A2 | 3/2006 |
| EP | 1344780 A1 | 9/2003 | | WO | 2006037537 A2 | 4/2006 |
| EP | 1354888 A1 | 10/2003 | | WO | 2006040625 A1 | 4/2006 |
| EP | 1385856 A | 2/2004 | | WO | 2006047248 A1 | 5/2006 |
| EP | 1406873 A2 | 4/2004 | | WO | 2006048427 A1 | 5/2006 |
| EP | 1500403 A1 | 1/2005 | | WO | 2006064033 A2 | 6/2006 |
| EP | 1553094 A1 | 7/2005 | | WO | 2006072334 A2 | 7/2006 |
| EP | 1564210 A1 | 8/2005 | | WO | 2006076231 A2 | 7/2006 |
| EP | 1586571 A1 | 10/2005 | | WO | 2006089872 A1 | 8/2006 |
| EP | 1609785 A1 | 12/2005 | | WO | 2006108842 A1 | 10/2006 |
| EP | 1791852 A2 | 6/2007 | | WO | 2006117359 A1 | 11/2006 |
| EP | 1852108 A1 | 11/2007 | | WO | 2006117360 A1 | 11/2006 |
| EP | 1852439 A1 | 11/2007 | | WO | 2006120208 A1 | 11/2006 |
| EP | 2143443 A1 | 1/2010 | | WO | 2006135693 A2 | 12/2006 |
| JP | 55007256 A | 1/1980 | | WO | 2007000445 A1 | 1/2007 |
| JP | 56039056 A | 4/1981 | | WO | 2007014886 A1 | 2/2007 |
| JP | 58164502 | 9/1983 | | WO | 2007014894 A2 | 2/2007 |
| JP | 62030750 A | 2/1987 | | WO | 2007014895 A2 | 2/2007 |
| JP | 11124392 A | 5/1999 | | WO | 2007025943 A2 | 3/2007 |
| JP | 2001288178 A | 10/2001 | | WO | 2007028814 A1 | 3/2007 |
| JP | 2003511458 A | 3/2003 | | WO | 2007031548 A2 | 3/2007 |
| JP | 2004196788 A | 7/2004 | | WO | 2007035665 A1 | 3/2007 |
| JP | 2004359630 | 12/2004 | | WO | 2007041053 A2 | 4/2007 |
| JP | 2005002092 A | 1/2005 | | WO | 2007071738 A1 | 6/2007 |
| JP | 2005060625 A | 3/2005 | | WO | 2007078726 A2 | 7/2007 |
| KR | 20070111099 A | 11/2007 | | WO | 2007093610 A1 | 8/2007 |
| WO | 9831697 A1 | 7/1998 | | WO | 2007120702 A2 | 10/2007 |
| WO | 0116147 A1 | 3/2001 | | WO | 2007120936 A2 | 10/2007 |
| WO | 0127128 A1 | 4/2001 | | WO | 2007128721 A | 11/2007 |
| WO | 0152825 A2 | 7/2001 | | WO | 2007128724 A1 | 11/2007 |
| WO | 0174834 A1 | 10/2001 | | WO | 2007128749 A1 | 11/2007 |
| WO | 0197808 A1 | 12/2001 | | WO | 2007128761 A1 | 11/2007 |
| WO | 0202560 A2 | 1/2002 | | WO | 2007144175 A2 | 12/2007 |
| WO | 02053573 A1 | 7/2002 | | WO | 2007149797 A2 | 12/2007 |
| WO | 02064606 A1 | 8/2002 | | WO | 2008017670 A1 | 2/2008 |
| WO | 02068420 A1 | 9/2002 | | WO | 2008020011 A1 | 2/2008 |
| WO | 02083066 A2 | 10/2002 | | WO | 2008034859 A1 | 3/2008 |
| WO | 03004496 A1 | 1/2003 | | WO | 2008049923 A1 | 5/2008 |
| WO | 03020737 A1 | 3/2003 | | WO | 2008055870 A1 | 5/2008 |
| WO | 03024965 A2 | 3/2003 | | WO | 2008055940 A2 | 5/2008 |
| WO | 03031458 A1 | 4/2003 | | WO | 2008062273 A1 | 5/2008 |
| WO | 03032997 A1 | 4/2003 | | WO | 2008089892 A1 | 7/2008 |
| WO | 03037327 A1 | 5/2003 | | WO | 2008090210 A1 | 7/2008 |
| WO | 03057200 A2 | 7/2003 | | WO | 2008093878 A1 | 8/2008 |
| WO | 03078404 A1 | 9/2003 | | WO | 2008093882 A1 | 8/2008 |
| WO | 03099836 A1 | 12/2003 | | WO | 2008101938 A1 | 8/2008 |
| WO | 2004007517 A1 | 1/2004 | | WO | 2008101939 A1 | 8/2008 |
| WO | 2004013118 A1 | 2/2004 | | WO | 2008101943 A1 | 8/2008 |
| WO | 2004018468 A2 | 3/2004 | | WO | 2008113000 A1 | 9/2008 |
| WO | 2004041820 A1 | 5/2004 | | WO | 2008116179 A2 | 9/2008 |
| WO | 2004046115 A1 | 6/2004 | | WO | 2008131149 A2 | 10/2008 |
| WO | 2004050658 A1 | 6/2004 | | WO | 2009022007 A1 | 2/2009 |
| WO | 2004052902 A1 | 6/2004 | | WO | 2009022008 A1 | 2/2009 |
| WO | 2004052903 A1 | 6/2004 | | WO | 2009022009 A1 | 2/2009 |
| WO | 2004063209 A2 | 7/2004 | | WO | 2009022010 A1 | 2/2009 |
| WO | 2004065380 A1 | 8/2004 | | WO | 2009024542 A2 | 2/2009 |
| WO | 2004076470 A2 | 9/2004 | | WO | 2009035969 A1 | 3/2009 |
| WO | 2004080990 A1 | 9/2004 | | WO | 2009063072 A2 | 5/2009 |

| | | | |
|---|---|---|---|
| WO | 2009091082 A1 | 7/2009 |
| WO | 2009099734 A1 | 8/2009 |
| WO | 2009121945 A2 | 10/2009 |
| WO | 2009123992 A1 | 10/2009 |
| WO | 2009147125 A1 | 12/2009 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092123 A1 | 8/2010 |
| WO | 2010092124 A1 | 8/2010 |
| WO | 2010092125 A1 | 8/2010 |
| WO | 2010092126 A1 | 8/2010 |
| WO | 2010092163 A2 | 8/2010 |
| WO | 2010138535 A1 | 12/2010 |
| WO | 2010147768 A1 | 12/2010 |
| WO | 2011039107 A1 | 4/2011 |
| WO | 2011039108 A2 | 4/2011 |
| WO | 2011039337 A1 | 4/2011 |
| WO | 2011039367 A2 | 4/2011 |
| WO | 2011060290 A2 | 5/2011 |
| WO | 2011064352 A1 | 6/2011 |
| WO | 2011113947 A1 | 9/2011 |
| WO | 2011117295 A1 | 9/2011 |
| WO | 2011120923 A1 | 10/2011 |
| WO | 2011138380 A1 | 11/2011 |
| WO | 2011138421 A1 | 11/2011 |
| WO | 2011161161 A1 | 12/2011 |
| WO | 2012062698 A1 | 5/2012 |
| WO | 2012065993 A1 | 5/2012 |
| WO | 2012107476 A1 | 8/2012 |
| WO | 2012120040 A1 | 9/2012 |

OTHER PUBLICATIONS

Benhaddou, Rachida., et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.
Byrn, Stephen et al. "Pharmaceutical Solids: A Strategic Approach to Regulatory Considerations" Pharmaceutical Research, vol. 12, No. 7, (1995) pp. 945-954.
CAS Registry No. 668270-12-0; STN database entered Mar. 28, 2004. 5 pgs.
Dohle, Wolfgang., et al; Copper-Mediated Cross-Coupling of Functionalized Arylmagnesium Reagents with Functionalized Alkyl and Benzylic Halides; Organic Letters (2001) vol. 3 No. 18 pp. 2871-2873.
Fuerstner, Alois., et al; Practical Method for the Rhodium-Catalyzed Addition of Aryl- and Alkenylboronic Acids to Aldehydes; Advanced Synthesis and Catalysis (2001) vol. 343 No. 4 pp. 343-350.
Hatsuda, Asanori., et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.
Hutton, Craig A., et al; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.
Iida, Takehiko., et al; Tributylmagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.
International Search Report for PCT/EP2005/002618 mailed Jun. 30, 2005.
International Search Report for PCT/EP2005/056806 mailed Dec. 27, 2006.
International Search Report for PCT/EP2006/061520 mailed Jul. 26, 2006.
International Search Report for PCT/EP2006/061956 mailed on Jul. 5, 2006.
International Search report for PCT/EP2006/061957 mailed on Jul. 5, 2006.
International Search Report for PCT/EP2006/062191 mailed Aug. 8, 2006.
International Search Report for PCT/EP2006/064702 mailed on Jul. 26, 2007.
International Search Report for PCT/EP2006/065710 mailed Mar. 8, 2007.
International Search Report for PCT/EP2006/066107 mailed Jan. 11, 2007.
International Search Report for PCT/EP2006/066347 mailed Mar. 7, 2007.
International Search Report for PCT/EP2007/051411 mailed on May 2, 2007.
International Search Report for PCT/EP2007/054248 mailed on Jun. 18, 2007.
Jagdmann Jr, G. Erik ; Synthesis of 5-(4-Substituted Benzyl)-2,4-Diaminoquinazolines as Inhibitors of *Candida albicans* Dihydrofolate Reductase; Journal Heterocyclic Chemical (1995) vol. 32 pp. 1461-1465.
Koo, Ja Seo., et al; 2-Pyridyl Cyanate: A Useful Reagent for he Preparation of Nitriles; Synthetic Communications (1996) vol. 26 No. 20 pp. 3709-3713; Marcel Dekker, Inc.
Kuribayashi, Takeshi., et al; Bis C-Glycosylated Diphenylmethanes for Stable Glycoepitope Mimetics; Syntletters (1999) vol. 6 pp. 737-740.
Kuribayashi, Takeshi., et al; c-Glycosylated Aryl tins: Versatile Building Blocks for Aryl C-Glycoside Glycomimetics; J. Carbohydrate Chemistry (1999) vol. 18, No. 4 pp. 371-382.
Kuribayashi, Takeshi., et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.
Langle, Sandrine., et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.
Lehmann, Ule et al. "Palladium-Catalyzed Cross-Coupling Reactions between Dihydropyranylindium Reagents and Aryl Halides, Synthesis of C-Aryl Glycals" Organic Letters, 2003, vol. 5, No. 14, pp. 2405-2408.
McLaughlin, Mark., et al; Suzuki-Miyaura Cross-Coupling of Benzylic Phospahates with Arylboronic Acids; Organic Letters (2005) vol. 7 No. 22 pp. 4875-4878.
Neamati, Ouri., et al;. "Depsides and Depsidones as Inhibiton of HIV-1 Integrase: Dimvery of Novel Inhibitors Through 3D Database Searclung", J. Med. Chem., 1997, vol. 40, pp. 942-951.
Nobre, Sabrina M., et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.
Office Action mailed Feb. 16, 2012, U.S. Appl. No. 12/703,988, filed Feb. 11, 2010. Inventor: Peter Eickelmann.
Oku, Akira., et al; T-1095, An Inhibitor or renal Na+ -Glucose Cotransporters, May Provide a Novel Approach to Treating Diabetes; Diabetes (1999) vol. 48 pp. 1794-1800.
Perner, Richard J., et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.
Rainier, Jon D. et al. "Aluminum- and Boron-Mediated C-Glycoside Synthesis from 1,2-Anhydroglycosides" Organic Letters, (2000) vol. 2, No. 17, pp. 2707-2709.
Randzio, Stanislaw L. et al. "Metastability and Instability of Organic Crystalline Substances" J. Phys. Chem. (2008) 112, pp. 1435-1444.
Revesz, Lasslo., et al; SAR of Benzoylpylpyridines and Benzophenones as p38 Alpha MAP Kinase Inhibitors with Oral Activity; Bioorganic & Medicinal Chemistry Letters (2004) vol. 14 pp. 3601-3605.
Salgado Junior, Wilson et al. "Nonalcoholic fatty liver disease and obesity" Acti Cirugica Brasiliera (2006) vol. 21, Supp. 1, pp. 72-78.
Singhal, Dharmendra et al. "Drug polymorphism and dosage form design: a practical perspective" Advanced Drug Delivery Reviews, 56, (2004) pp. 335-347.

Sommer, Michael Bech., et al; displacement of Halogen of 2-Halogeno-Substituted Benzonitriles with Carbonions. Preparation of (2-Cyanoaryparylacetonitriles; Journal of Organic Chemistry (1990) vol. 55 pp. 4817-4821.

Stazi, Federica., et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.

The Merck Manual Diagnosis and Therapy; Seventeenth Edition; "13 / Disorders of Carbohyrate Metabolism" Merck Research Laboratories (1999) pp. 165-177.

Thomas, Leo et al. "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics (2008) 325, pp. 175-182.

Threlfall, Terry "Structural and Thermodynamic Explanations of Ostwald's Rule" Organic Process Research & Development (2003) vol. 7, pp. 1017-1027.

Tykwinski, Rik R; Evolution in the Palladium-Catalyzed Cross-Coupling of sp- and sp2-Hybridized Carbon Atoms; Angew Chemical International Edition (2003) vol. 42 pp. 1566-1568.

U.S. Appl. No. 13/287,216, filed Nov. 2, 2011. Inventor: Rolf Grempler.

U.S. Appl. No. 13/367,739, filed Feb. 7, 2012. Inventor: Thomas Klein.

Ueta, Kiichiro., et al; Long-Term Treatment with the Na+ -Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.

Wallace, Debra J., et al; Cyclopropylboronic Acid: Synthesis and Suzuki Cross-Coupling Reactions; Tetrahedron Letters (2002) vol. 43 pp. 6987-6990; Pergamon Press.

Xue, Song., et al; Zinc-mediated Synthesis of Alpha-C-Glycosided from 1,2-Anhydroglycosides; Synletters (2003) vol. 6 pp. 870-872.

Final Office Action mailed Dec. 10, 2012, U.S. Appl. No. 12/703,988, filed Feb. 11, 2010. Inventor: Peter Eickelmann.

International Search Report for PCT/EP2007/062023 mailed Sep. 17, 2008.

International Search Report for PCT/EP2011/054734 mailed Aug. 12, 2011.

International Search Report for PCT/EP2012/052108 mailed Mar. 8, 2012.

Merriam-Webster's Collegiate Dictionary, published 1998 by Merriam-Webster Inc. "prevent".

Office Action mailed Sep. 28, 2012. U.S. Appl. No. 12/704,019, filed Feb. 11, 2010. First named inventor: Wolfram Eisenreich.

U.S. Appl. No. 13/413,702, filed Mar. 7, 2012. Inventor: Masanori Ito.

U.S. Appl. No. 13/693,239, filed Dec. 4, 2012. Inventor: Klaus Dugi.

Abstract in English for KR20070111099, Nov. 11, 2007.

Ahren B: "DPP-4 inhibitors", Best practice and research in clinical endocrinology and metabolism—New therapies for diabetes 200712 GB LNKD- DOI:10.1016/J. Beem.2007.07.005, vol. 21, No. 4, Dec. 2007, pp. 517-533.

Aulinger, B.A. et al., "Ex-4 and the DPP-IV Inhibitor Vildagliptin have Additive Effects to Suppress Food Intake in Rodents". Abstract No. 1545-P, 2008.

Ault Addison, "Techniques and experiments for organic chemistry" University Science Books, 1998, pp. 59-60.

Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 186-193.

Castaneda, Francisco et al. "Thioglycosides as inhibitors of hSGLT1 and hSGLT2: Potential therapeutic agents for the control of hyperglycemia in diabetes" International Journal of Medical Sciences (2007) 4(3), pp. 131-139.

Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCT00601250/2008_01_25 [retrieved on Feb. 27, 2009 ].

Clinical Trials. NCT00622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.govict2/ show/.

Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT0095444712010_06_14>;.

Clinical Trials: NCT00309608. Efficacy and safety of BI 1356 in combination with metformin in patients with type2 diabetes . Boehringer Ingelheim Pharmaceuticals, Jan. 27, 2009. Clinical Trials.gov . http://clinicaltrials.gov/ archive/NCT00309608/2009_01_27.

Clinical Trials: NCT00602472. "BI 1356 in combination withe metformin and a sulphonylurea in Type 2 Diabetes". DrugLib.com, Nov. 3, 2008. http://www.druglib.com/trial/081NCT00309608.html.

Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/ NCT00622284/2010_01_13.

Clinical Trials: NCT00798161. "Safety and efficacy of BI 1356 Plus Metformin in Type 2 Diabetes, Factorial Design". Clinical Trials.gov archive. A Service of the U.S> National Institutes of Health. Nov. 24, 2008, p. 1-3. http:// clinicaltrials.gov/archive/NCT00798161/2008_11_24.

Conarello, S.L. et al., "Mice lacking dipeptidyl peptidase IV are protected against obesity and insulin resistance". PNAS, May 27, 2003, vol. 100, No. 11, p. 6825-6830.

Deacon, Carolyn F. "Perspectives in Diabetes Therapeutic Strategies Based on Glucagon-Like Peptide 1" Diabetes, (2004) vol. 53 pp. 2181-2189.

Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.

Fujimori, Yoshikazu et al. "Remogliflozin Etabonate in a Novel Category of Selective Low-Affinity Sodium Glucose Cotransporter (SGLT2) Inhibitors, Exhibits Antidiabetic Efficacy in Rodent Models" (2008) Journal of Pharmacology and Experimental Therapeutics vol. 327 No. 1, pp. 268-276.

Gallwitz, B. "Sitagliptin with Metformin: Profile of a Combination for the Treatment of Type 2 Diabetes". Drugs of Today, Oct. 2007, 43(10), p. 681-689.

Ghassemi et al. "Synthesis and properties of new sulfonated poly(p-phenylene) derivatives for proton exchange membranes" Polymer (2004) pp. 5847-5854.

Graefe-Mody et al., "The novel DPP-4 inhibitor..." Diabetes, (online) 2008, XP002561421 http://professional.diabetes.org/content/posters/2008/p553-p.pdf.

Graefe-Mody, E.U., et al., "Evaluation of the potential for steady-state pharmacokinectic and pharmacodynamic interactions between the DPP-4 inhibitor linagliptin and metformin in healthy subjects". Current Medical Research and Opinion, Informa Healthcare, GB, vol. 25. No. 8, Aug. 1, 2009, pp. 1963-1972.

Greco, Gary T. et al. "Segregation of Active Constituents from Tablet Formulations During Grinding: Theoretical Considerations" Drug Development and Industrial Pharmacy, (1982) 8(4), pp. 565-578.

Gwaltney, S. "Medicinal Chemistry Approaches to the Inhibition of Dipeptidyl Peptidase IV", Current Topics in Medicinal Chemistry, 2008, 8, p. 1545-1552.

He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.

Hussey, Elizabeth K. et al. "Safety, Pharmacokinetics and Pharmacodynamics of Remogliflozin Etabonate (SGLT2 Inhibitor)

and Metformin When Co-Administered in Type 2 Diabetes Mellitus (T2DM) Patients" Diabetes, American Diabetes Association, (2009) XP00913667, vol. 58, p. A157.

International Search Report and Written Opinion for PCT/EP2012/053910 mailed May 14, 2012.

International Search Report for PCT/EP2008/060736 mailed Nov. 28, 2008.

International Search Report for PCT/EP2008/060744 mailed Dec. 5, 2008.

International Search Report for PCT/EP2010/051735 mailed May 20, 2010.

International Search Report for PCT/EP2010/051736 mailed May 7, 2010.

International Search Report for PCT/EP2011/069532 mailed Dec. 15, 2011.

International Search Report for PCT/EP2012/053910 mailed May 14, 2012.

Isaji, Masayuki "Sodium-glucose cotransporter inhibitors for diabetes" Current Opinion in Investigational Drugs, (2007) vol. 8, No. 4, pp. 285-292.

Kadowaki, Tet al. "PPAR gamma agonist and antagonist" Nihon Yakurigaku Zasshi (2001) vol. 118, No. 9, pp. 321-326. (English abstract).

Katsuno, Kenji et al. "Sergliflozin, a Novel Selective Inhibitor of Low-Affinity Sodium Glucose Cotransporter (SGLT2) Validates the Critical Role of SGLT2 in Renal Glucose Reabsorption and Modulates Plasma Glucose Level" The Journal of Pharmacology and Experimental Therapeutics (2007) vol. 320, No. 1, pp. 323-330.

Knochel, Paul et al. "Highly functionalized Organomagnesium Reagents Prepared through Halogen-Metal Exchange" Angew. Chem. INt. Ed. (2003) vol. 42, 4302-4320.

Krasovskiy Arkady et al. "A LiCL-Mediated Br/Mg Exchange Reaction for the Preparation of Functionalized Aryl-and Heterarylmagnesium Compounds from Organic Bromides**" Angew. Chem. Int. Ed. (2004) vol. 43, pp. 3333-3336.

Levien,T.L. et al, "New drugs in development for the treatment of diabetes", Diabetes Spectrum, American Diabetes Association, US, vol. 22, No. 2, Jan. 1, 2009, pp. 92-106.

Li, T, et al. "Lack of Pharmacokinetic Interaction between Dapagliflozin and Pioglitazone in Healthy Subjects" Journal of Clinical Pharmacology, (2009) vol. 49, No. 9, pp. 1093.

Lipworth, Brian J. "Clinical pharmacology of b3-adrenoceptors" Br J Clin Pharmacol (1996) pp. 291-300.

McMaster University, Chem2006 Lab Manual, 1997/98, Expt 1, Part B, pp. 1-9.

Meece, J. "When Oral Agents Fail: Optimizing Insulin Therapy in The Older Adult". Consultant Pharmacist, the Society, Arlington, VA U.S. vol. 24, No. Suppl B, Jun. 1, 2009, p. 11-17.

Merck Manual of Diagnosis and Therapy, 17th Edition, (1999) Ch 13 / Disorders of Carohydrate Metabolism, Diabetes Mellitus. pp. 165-177.

Merck Manual Online Edition, "Diabetes Mellitus" http://www.merckmanuals.com/professional/ endocrine_and_metabolic_disorders/diabetes_mellitus_and_disorders of carbohyrate_metabolism/ diabetes_mellitus_dm.html#v987998. last revision Jun. 2008 by Preeti Kishore M.D.

Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www. webwire.com/ViewPressRel.asp?aId=96695.

Mooradian, Arsharg D. et al. "Narrative Review: a Rational Approach to Starting Insulin Therapy" (2006) Annals of Internal Medicine, vol. 145, pp. 125-134.

Office Action mailed on Jun. 5, 2012. U.S. Appl. No.: 12/673,319 filed on Apr. 15, 2010. First named inventor: Klaus Dugi.

Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.

Piya, Milan K. et al. "Emerging treatment options for type 2 diabetes" British Journal of Clinical Pharmacology, (2010) vol. 70, No. 5, pp. 631-644.

Printz, Richard L. et al. "Tweaking the Glucose Sensor: Adjusting Glucokinase Activity with Activator Compounds" Endocrinology, (2005) vol. 146, No. 9, pp. 3693-3695.

Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.

Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.

Rudnic, Edward et al. "Oral Solid Dosage Forms" Remington's Pharmaceutical Sciences, 18th Ed, Gennaro, A.R. Ed, Macie Pub. Co. (1990) pp. 1633-1665.

Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).

Sherwin, Robert S. et al. "The Prevention or Delay of Type 2 Diabetes" Diabetes Care, (2002) vol. 25, No. 4, pp. 742-749.

Silverman, et al. "Handbook of Grignard Reagents" Marcel Dekker (1996) p. 82.

Tanaka, Chikako "Therapeutic Drugs for Metabolic Diseases, Chapter 2"(2002) New Yakurigaku (New Pharmacology) pp. 524-527.

Thomas, L.,"Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.

U.S. Appl. No. 13/484,506, filed May 31, 2012. Inventor: Marion Wienrich.

U.S. Appl. No. 13/539,713, filed Jul. 2, 2012. Inventor: Uli Broedl.

U.S. Appl. No. 13/634,886, filed Sep. 14, 2012. Inventor: Peter Eickelmann.

U.S. Appl. No. 13/637,413, filed Sep. 26, 2012. Inventor: Rolf Grempler.

U.S. Appl. No. 13/695,492, filed Oct. 31, 2012. Inventor: Thomas Klein.

Wang Y et al: "BI-1356. Dipeptidyl-peptidase IV inhibitor, antidiabetic agent." Drugs of the Future, Prous Science, ES,vol. 33, No. 6, Jun. 1, 2008, pp. 473-477.

Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.

www.who.int/medicinedocs/index/assoc/s14141e/s14141e.pdf Addendum 1 to "The use of stems in the selection of International Nonproprietary names (INN) for pharmaceutical substances" World Health Organization Jun. 19, 2007, pp. 1-3, XP007906327

Yamada, Yuichiro et al. "Clinic: Careful Progress in the Field and new Therapeutic Methods" Medical Online, (2007) vol. 220, No. 13, pp. 1219-1221.

Zhang, L. et al "Dapagliflozin treatment in patients with different stages of type 2 diabetes mellitus: effects on glycaemic control and body weight" Diabetes, Obesity and Metabolism (2010) vol. 12, No. 6, p. 510-515.

Augeri , David J. "Discovery and Preclinical Profile of Saxagliptin (BMS-477118): A Highly Potent, Long-Acting, Orally Active Dipeptidyl Peptidase IV Inhibitor for the Treatment of Type 2 Diabetes" J. Med. Chem. (2005) vol. 48, pp. 5025-5037.

Drug Watch "Type 2 Diabetes Mellitus" Formulary vol. 43 Aug. 2008 p. 304.

Eckhardt, M. et al.,"8-(3-(R)-Aminopiperidin-1-y1)-7-but-2-ynyl-3-methyl-1-(4-methyl-quinazolin-2-ylmethyl)-3,7- dihydropurine-2,6-dione (BI1356), a Highly Potent, Selective, Long-Acting, and Orally Bioavailable DPP-4 Inhibitor for the Treatment of Type 2 Diabetes" J. Med Chem (2007) vol. 50, pp. 6450-6453.

Gallwitz, Baptist "Saxagliptin, a dipeptidyl peptidase IV inhibitor for the treatment of type 2 diabetes" IDrugs (2008) 11(12), pp. 906-917.

Huttner, S. et al. "Safety, Tolerability, Pharmacokinetics, and Pharmacodynamics of Single Oral Doses of BI 1356, and Inhibitor of Dipeptidyl Peptidase 4, in Healthy Male Volunteers" Journal of Clinical Pharmacology (2008) V 48, pp. 1171-1178.

Mchale, Mary "Grignard Reaction" Connexions module: m15245, (2007) pp. 1-18.

Meng, Wei et al "Discovery of Dapagliflozin: A Potent, Selective Renal Sodium-Dependent Glucose Cotransporter 2 (SGLT2) Inhibitor for the Treatment of Type 2 Diabetes" J. Med. Chem. (2008) vol. 51, pp. 1145-1149.

Redenti, Enrico et al. "Drug/Cycloclextrin/Hydroxy Acid Multicomponent Systems. Properties and Pharmaceutical Applications" Journal of Pharmaceutical Sciences, (2000) vol. 89, No. 1, pp. 1-8.

U.S. Appl. No. 13/785,365 filed Mar. 5, 2013. Inventor: Masanori Ito.

U.S. Appl. No. 13/833,097 filed Mar. 15, 2013. Inventor: Eric Williams Mayoux.

* cited by examiner

US 8,551,957 B2

PHARMACEUTICAL COMPOSITION COMPRISING A GLUCOPYRANOSYL-SUBSTITUTED BENZENE DERIVATE

This application is the national phase entry under 35 U.S.C. §371 of International Application No. PCT/EP2008/060736, filed Aug. 15, 2008, which claims priority to European Patent Application No. 07114459.6, filed Aug. 16, 2007, which are hereby incorporated by reference in their entireties.

TECHNICAL FIELD OF THE INVENTION

The invention relates to a pharmaceutical composition comprising a glucopyranosyl-substituted benzene derivative of the formula (I) as described hereinafter in combination with a DPP IV inhibitor as specified hereinafter which is suitable in the treatment or prevention of one or more conditions selected from type 1 diabetes mellitus, type 2 diabetes mellitus, impaired glucose tolerance, impaired fasting blood glucose and hyperglycemia.

Furthermore the invention relates to methods
  for preventing, slowing progression of, delaying, or treating a metabolic disorder;
  for improving glycemic control and/or for reducing of fasting plasma glucose, of postprandial plasma glucose and/or of glycosylated hemoglobin HbA1c;
  for preventing, slowing, delaying or reversing progression from impaired glucose tolerance, impaired fasting blood glucose, insulin resistance and/or from metabolic syndrome to type 2 diabetes mellitus;
  for preventing, slowing progression of, delaying or treating of a condition or disorder selected from the group consisting of complications of diabetes mellitus;
  for reducing body weight or preventing an increase in body weight or facilitating a reduction in body weight;
  for preventing or treating the degeneration of pancreatic beta cells and/or for improving and/or restoring the functionality of pancreatic beta cells and/or restoring the functionality of pancreatic insulin secretion;
  for preventing, slowing, delaying or treating diseases or conditions attributed to an abnormal accumulation of liver fat;
  maintaining and/or improving the insulin sensitivity and/or for treating or preventing hyperinsulinemia and/or insulin resistance,
in patients in need thereof characterized in that a glucopyranosyl-substituted benzene derivative of formula (I) as defined hereinafter is administered in combination or alternation with a DPP IV inhibitor as defined hereinafter.

In addition the present invention relates to the use of a glucopyranosyl-substituted benzene derivative of the formula (I) as defined hereinafter for the manufacture of a medicament for use in a method as described hereinbefore and hereinafter.

In addition, the present invention relates to the use of a DPP IV inhibitor as defined hereinafter for the manufacture of a medicament for use in a method as described hereinbefore and hereinafter.

The invention also relates to a use of a pharmaceutical composition according to this invention for the manufacture of a medicament for use in a method as described hereinbefore and hereinafter.

BACKGROUND OF THE INVENTION

Glucopyranosyl-substituted benzene derivative are described in the prior art, for example in WO 01/27128, WO 03/099836, WO 2005/092877, WO 2006/034489, WO 2006/064033, WO 2006/117359, WO 2006/117360, WO 2007/025943, WO 2007/028814, WO 2007/031548, WO 2007/093610, WO 2007/128749, WO 2008/049923, WO 2008/055870, WO 2008/055940. The glucopyranosyl-substituted benzene derivatives are proposed as inducers of urinary sugar excretion and as medicaments in the treatment of diabetes.

Renal filtration and reuptake of glucose contributes, among other mechanisms, to the steady state plasma glucose concentration and can therefore serve as an antidiabetic target. Reuptake of filtered glucose across epithelial cells of the kidney proceeds via sodium-dependent glucose cotransporters (SGLTs) located in the brush-border membranes in the tubuli along the sodium gradient[1]. There are at least 3 SGLT isoforms that differ in their expression pattern as well as in their physico-chemical properties[2]. SGLT2 is exclusively expressed in the kidney[3], whereas SGLT1 is expressed additionally in other tissues like intestine, colon, skeletal and cardiac muscle[4, 5]. SGLT3 has been found to be a glucose sensor in interstitial cells of the intestine without any transport function[6]. Potentially, other related, but not yet characterized genes, may contribute further to renal glucose reuptake[7, 8, 9]. Under normoglycemia, glucose is completely reabsorbed by SGLTs in the kidney, whereas the reuptake capacity of the kidney is saturated at glucose concentrations higher than 10 mM, resulting in glucosuria ("diabetes mellitus"). This threshold concentration can be decreased by SGLT2-inhibition. It has been shown in experiments with the SGLT inhibitor phlorizin that SGLT-inhibition will partially inhibit the reuptake of glucose from the glomerular filtrate into the blood leading to a decrease in blood glucose concentrations and to glucosuria[10, 11].

(1) Wright, E. M. (2001) Am. J. Renal Physiol. 280, F10-F18;
(2) Wright, E. M. et al. (2004) Pflugers Arch. 447(5):510-8;
(3) You, G. et al. (1995) J. Biol. Chem. 270 (49) 29365-29371;
(4) Pajor A M, Wright E M (1992) J. Biol. Chem. 267(6): 3557-3560;
(5) Zhou, L. et al. (2003) J. Cell. Biochem. 90:339-346;
(6) Diez-Sampedro, A. et al. (2003) Proc. Natl. Acad. Sci. USA 100(20), 11753-11758;
(7) Tabatabai, N. M. (2003) Kidney Int. 64, 1320-1330;
(8) Curtis, R. A. J. (2003) US Patent Appl. 2003/0054453;
(9) Bruss, M. and Bonisch, H. (2001) Cloning and functional characterization of a new human sugar transporter in kidney (Genbank Acc. No. AJ305237);
(10) Rossetti, L. Et al. (987) J. Clin. Invest. 79, 1510-1515;
(11) Gouvea, W. L. (1989) Kidney Int. 35(4):1041-1048.

DPP IV inhibitors represent a novel class of agents that are being developed for the treatment or improvement in glycemic control in patients with type 2 diabetes.

For example, DPP IV inhibitors and their uses are disclosed in WO 2002/068420, WO 2004/018467, WO 2004/018468, WO 2004/018469, WO 2004/041820, WO 2004/046148, WO 2005/051950, WO 2005/082906, WO 2005/063750, WO 2005/085246, WO 2006/027204, WO 2006/029769, WO2007/014886; WO 2004/050658, WO 2004/111051, WO 2005/058901, WO 2005/097798; WO 2006/068163, WO 2007/071738, WO 2008/017670; WO 2007/054201 or WO 2007/128761.

As further DPP IV inhibitors the following compounds can be mentioned:
  Sitagliptin (MK-0431) having the structural formula A below is (3R)-3-amino-1-[3-(trifluoromethyl)-5,6,7,8-tetrahydro-5H-[1,2,4]triazolo[4,3-a]pyrazin-7-yl]-4-(2,4,5-trifluorophenyl)butan-1-one, also named (2R)-4- oxo-4-[3-(trifluoromethyl)-5,6-dihydro[1,2,4]triazolo[4,3-a]pyrazin-7(8H)-yl]-1-(2,4,5-trifluorophenyl)butan-2-amine,

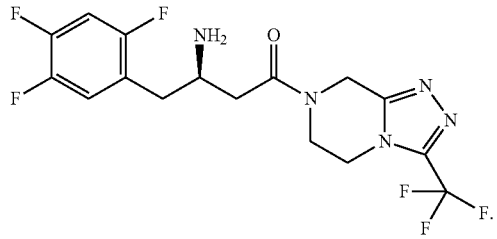

(A)

In one embodiment, sitagliptin is in the form of its dihydrogenphosphate salt, i.e. sitagliptin phosphate. In a further embodiment, sitagliptin phosphate is in the form of a crystalline anhydrate or monohydrate. A class of this embodiment refers to sitagliptin phosphate monohydrate. Sitagliptin free base and pharmaceutically acceptable salts thereof are disclosed in U.S. Pat. No. 6,699,871 and in Example 7 of WO 03/004498. Crystalline sitagliptin phosphate monohydrate is disclosed in WO 2005/003135 and in WO 2007/050485. For details, e.g. on a process to manufacture or to formulate this compound or a salt thereof, reference is thus made to these documents. A tablet formulation for sitagliptin is commercially available under the trade name Januvia®.

Vildagliptin (LAF-237) having the structural formula B below is (2S)-{[(3-hydroxyadamantan-1-yl)amino]acetyl}pyrrolidine-2-carbonitrile, also named (S)-1-[(3-hydroxy-1-adamantyl)-amino]acetyl-2-cyano-pyrrolidine,

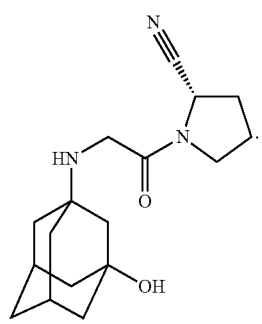

(B)

Vildagliptin is specifically disclosed in U.S. Pat. No. 6,166,063 and in Example 1 of WO 00/34241. Specific salts of vildagliptin are disclosed in WO 2007/019255. A crystalline form of vildagliptin as well as a vildagliptin tablet formulation are disclosed in WO 2006/078593. Vildagliptin can be formulated as described in WO 00/34241 or in WO 2005/067976. A modified release vildagliptin formulation is described in WO 2006/135723. For details, e.g. on a process to manufacture or to formulate this compound or a salt thereof, reference is thus made to these documents. A tablet formulation for vildagliptin is expected to be commercially available under the trade name Galvus®.

Saxagliptin (BMS-477118) having the structural formula C below is (1S,3S,5S)-2-{(2S)-2-amino-2-(3-hydroxyadamantan-1-yl)acetyl}-2-azabicyclo[3.1.0]hexane-3-carbonitrile, also named (S)-3-hydroxyadamantylglycine-L-cis-4,5-methanoprolinenitrile,

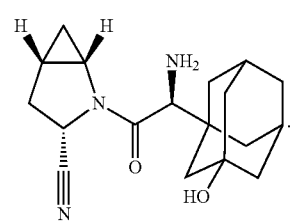

(C)

Saxagliptin is specifically disclosed in U.S. Pat. No. 6,395,767 and in Example 60 of WO 01/68603. In one embodiment, saxagliptin is in the form of its HCl salt or its monobenzoate salt as disclosed in WO 2004/052850. In a further embodiment, saxagliptin is in the form of the free base. In a yet further embodiment, saxagliptin is in the form of the monohydrate of the free base as disclosed in WO 2004/052850. A process for preparing saxagliptin is also disclosed in WO 2005/106011 and WO 2005/115982. Saxagliptin can be formulated in a tablet as described in WO 2005/117841. For details, e.g. on a process to manufacture, to formulate or to use this compound or a salt thereof, reference is thus made to these documents.

Denagliptin (GSK-823093) having the structural formula D below is (2S,4S)-1-[(2S)-2-amino-3,3-bis(4-fluorophenyl)propionyl]-4-fluoropyrrolidine-2-carbonitrile, also named (2S,4S)-4-fluoro-1-[4-fluoro-beta-(4-fluorophenyl)-L-phenylalanyl]-2-pyrrolidinecarbonitrile

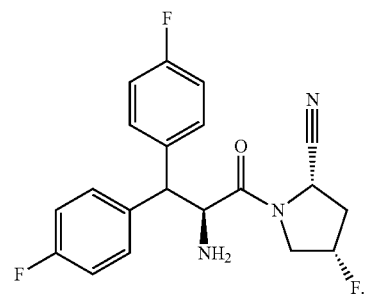

(D)

Denagliptin is specifically disclosed in U.S. Pat. No. 7,132,443 and in WO 03/002531. In one embodiment, denagliptin is in the form of its hydrochloride salt as disclosed in Example 2 of WO 03/002531 or its tosylate salt as disclosed in WO 2005/009956. A class of this embodiment refers to denagliptin tosylate. Crystalline anhydrous denagliptin tosylate is disclosed in WO 2005/009956. For details on a process to manufacture this compound or a salt thereof, reference is thus made to these documents.

Alogliptin (SYR-322) having the structural formula E below is 2-({6-[(3R)-3-aminopiperidin-1-yl]-3-methyl-2,4-dioxo-3,4-dihydro-2H-pyrimidin-1-yl}methyl)benzonitrile (E)

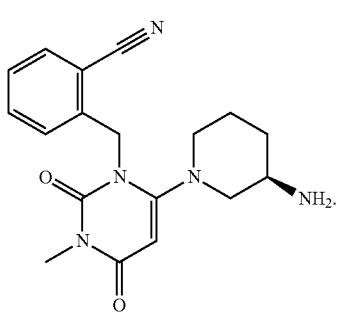

Alogliptin is specifically disclosed in US 2005/261271, EP 1586571 and in WO 2005/095381. In one embodiment, alogliptin is in the form of its benzoate salt, its hydrochloride salt or its tosylate salt each as disclosed in WO 2007/035629. A class of this embodiment refers to alogliptin benzoate. Polymorphs of alogliptin benzoate are disclosed in WO 2007/035372. A process for preparing alogliptin is disclosed in WO 2007/112368 and, specifically, in WO 2007/035629. Alogliptin (namely its benzoate salt) can be formulated in a tablet and administered as described in WO 2007/033266. For details, e.g. on a process to manufacture, to formulate or to use this compound or a salt thereof, reference is thus made to these documents.

(2S)-1-{[2-(5-Methyl-2-phenyl-oxazol-4-yl)-ethylamino]-acetyl}-pyrrolidine-2-carbonitrile or a pharmaceutically acceptable salt thereof, preferably the mesylate, or (2S)-1-{[1,1-Dimethyl-3-(4-pyridin-3-yl-imidazol-1-yl)-propylamino]-acetyl}-pyrrolidine-2-carbonitrile or a pharmaceutically acceptable salt thereof.

These compounds and methods for their preparation are disclosed in WO 03/037327. The mesylate salt of the former compound as well as crystalline polymorphs thereof are disclosed in WO 2006/100181. The fumarate salt of the latter compound as well as crystalline polymorphs thereof are disclosed in WO 2007/071576. These compounds can be formulated in a pharmaceutical composition as described in WO 2007/017423. For details, e.g. on a process to manufacture, to formulate or to use these compounds or a salt thereof, reference is thus made to these documents.

(S)-1-((2S,3S,11bS)-2-Amino-9,10-dimethoxy-1,3,4,7,11b-hexahydro-2H-pyrido[2,1-a]isoquinolin-3-yl)-4-fluoromethyl-pyrrolidin-2-one or a pharmaceutically acceptable salt thereof.

This compound and methods for its preparation are disclosed in WO 2005/000848. A process for preparing this compound (specifically its dihydrochloride salt) is also disclosed in WO 2008/031749, WO 2008/031750 and WO 2008/055814. This compound can be formulated in a pharmaceutical composition as described in WO 2007/017423. For details, e.g. on a process to manufacture, to formulate or to use this compound or a salt thereof, reference is thus made to these documents.

(3,3-Difluoropyrrolidin-1-yl)-((2S,4S)-4-(4-(pyrimidin-2-yl)piperazin-1-yl)pyrrolidin-2-yl)methanone or a pharmaceutically acceptable salt thereof.

This compound and methods for its preparation are disclosed in WO 2005/116014 and U.S. Pat. No. 7,291,618. For details, e.g. on a process to manufacture, to formulate or to use this compound or a salt thereof, reference is thus made to these documents.

(1((3S,4S)-4-amino-1-(4-(3,3-difluoropyrrolidin-1-yl)-1,3,5-triazin-2-yl)pyrrolidin-3-yl)-5,5-difluoropiperidin-2-one or a pharmaceutically acceptable salt thereof.

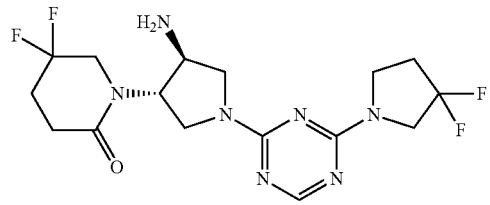 [SMILES: N[C@H]1CN(c2ncnc(N3CCC(F)(F)C3)n2)C[C@@H]1N1CC(F)(F)CCC1=O]

This compound and methods for its preparation are disclosed in WO 2007/148185 and US 20070299076. For details, e.g. on a process to manufacture, to formulate or to use this compound or a salt thereof, reference is thus made to these documents.

(2S,4S)-1-{2-[(3S,1R)-3-(1H-1,2,4-Triazol-1-ylmethyl)cyclopentylamino]-acetyl}-4-fluoropyrrolidine-2-carbonitrile or a pharmaceutically acceptable salt thereof.

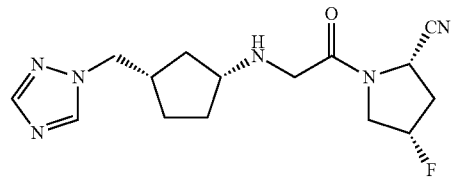 [SMILES: N#C[C@@H]1C[C@H](F)CN1C(=O)CN[C@@H]1CC[C@H](Cn2cncn2)C1]

This compound and methods for its preparation are disclosed in WO 2006/040625 and WO 2008/001195. Specifically claimed salts include the methanesulfonate and p-toluenesulfonate. For details, e.g. on a process to manufacture, to formulate or to use this compound or a salt thereof, reference is thus made to these documents.

(R)-2-[6-(3-Amino-piperidin-1-yl)-3-methyl-2,4-dioxo-3,4-dihydro-2H-pyrimidin-1-ylmethyl]-4-fluoro-benzonitrile or a pharmaceutically acceptable salt thereof.

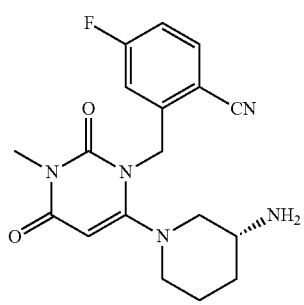 [SMILES: Cn1c(=O)cc(N2CCC[C@@H](N)C2)n(Cc2cc(F)ccc2C#N)c1=O]

This compound and methods for its preparation and use are disclosed in WO 2005/095381, US 2007060530, WO 2007/035629, WO 2007/074884, WO 2007/112368 and WO 2008/033851. Specifically claimed salts include the succinate, benzoate, benzene-sulfonate, p-toluenesulfonate, (R)-mandelate and hydrochloride. For details, e.g. on a process to manufacture, to formulate or to use this compound or a salt thereof, reference is thus made to these documents.

For avoidance of any doubt, the disclosure of each of the foregoing documents cited above in connection with the specified DPP IV inhibitors is specifically incorporated herein by reference in its entirety.

Type 2 diabetes is an increasingly prevalent disease that due to a high frequency of complications leads to a significant reduction of life expectancy. Because of diabetes-associated microvascular complications, type 2 diabetes is currently the most frequent cause of adult-onset loss of vision, renal failure, and amputations in the industrialized world. In addition, the presence of type 2 diabetes is associated with a two to five fold increase in cardiovascular disease risk.

After long duration of disease, most patients with type 2 diabetes will eventually fail on oral therapy and become insulin dependent with the necessity for daily injections and multiple daily glucose measurements.

The UKPDS (United Kingdom Prospective Diabetes Study) demonstrated that intensive treatment with metformin, sulfonylureas or insulin resulted in only a limited improvement of glycemic control (difference in HbA1c ~0.9%). In addition, even in patients within the intensive treatment arm glycemic control deteriorated significantly over time and this was attributed to deterioration of β-cell function. Importantly, intensive treatment was not associated with a significant reduction in macrovascular complications, i.e. cardiovascular events.

Therefore, there is an unmet medical need for methods, medicaments and pharmaceutical compositions with a good efficacy with regard to glycemic control, with regard to disease-modifying properties and with regard to reduction of cardiovascular morbidity and mortality while at the same time showing an improved safety profile.

AIM OF THE PRESENT INVENTION

The aim of the present invention is to provide a pharmaceutical composition and method for preventing, slowing progression of, delaying or treating a metabolic disorder, in particular of type 2 diabetes mellitus.

A further aim of the present invention is to provide a pharmaceutical composition and method for improving glycemic control in a patient in need thereof.

Another aim of the present invention is to provide a pharmaceutical composition and method for preventing, slowing or delaying progression from impaired glucose tolerance (IGT), impaired fasting blood glucose (IFG), insulin resistance and/or metabolic syndrome to type 2 diabetes mellitus.

Yet another aim of the present invention is to provide a pharmaceutical composition and method for preventing, slowing progression of, delaying or treating of a condition or disorder from the group consisting of complications of diabetes mellitus.

A further aim of the present invention is to provide a pharmaceutical composition and method for reducing the weight or preventing an increase of the weight in a patient in need thereof.

Another aim of the present invention is to provide a new pharmaceutical composition with a high efficacy for the treatment of metabolic disorders, in particular of diabetes mellitus, impaired glucose tolerance (IGT), impaired fasting blood glucose (IFG), and/or hyperglycemia, which has good to very good pharmacological and/or pharmacokinetic and/or physicochemical properties.

Further aims of the present invention become apparent to the one skilled in the art by description hereinbefore and in the following and by the examples.

SUMMARY OF THE INVENTION

Within the scope of the present invention it has now surprisingly been found that a pharmaceutical composition comprising a glucopyranosyl-substituted benzene derivative of the formula (I) as defined hereinafter can advantageously be used in combination with a DPP IV inhibitor as specified hereinafter for preventing, slowing progression of, delaying or treating a metabolic disorder, in particular in improving glycemic control in patients. This opens up new therapeutic possibilities in the treatment and prevention of type 2 diabetes mellitus, overweight, obesity, complications of diabetes mellitus and of neighboring disease states.

Therefore, in a first aspect the present invention provides a pharmaceutical composition comprising a glucopyranosyl-substituted benzene derivative of the formula (I)

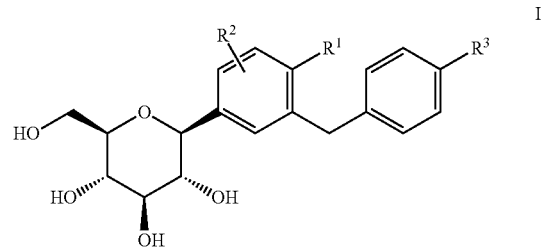

wherein $R^1$ denotes Cl, methyl or cyano; $R^2$ denotes H, methyl, methoxy or hydroxy and $R^3$ denotes ethyl, cyclopropyl, ethynyl, ethoxy, (R)-tetrahydrofuran-3-yloxy or (S)-tetrahydrofuran-3-yloxy, either, in a first embodiment (embodiment A), in combination with a DPP IV inhibitor of formula (I)

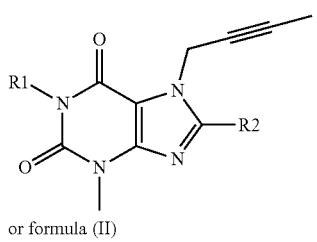

(I)

or formula (II)

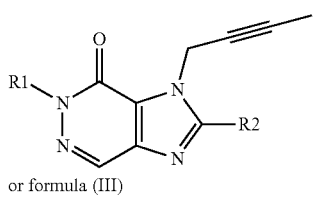

(II)

or formula (III)

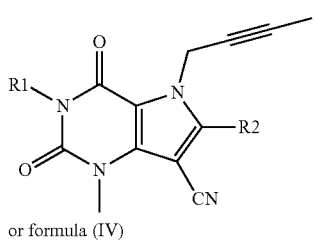

(III)

or formula (IV)

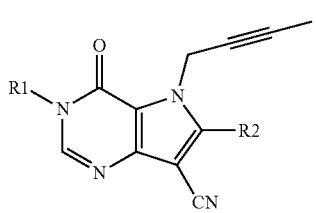

(IV)

wherein R1 denotes ([1,5]naphthyridin-2-yl)methyl, (quinazolin-2-yl)methyl, (quinoxalin-6-yl)methyl, (4-methyl-quinazolin-2-yl)methyl, 2-cyano-benzyl, (3-cyano-quinolin-2-yl)methyl, (3-cyano-pyridin-2-yl)methyl, (4-methyl-pyrimidin-2-yl)methyl, or (4,6-dimethyl-pyrimidin-2-yl)methyl and R2 denotes 3-(R)-amino-piperidin-1-yl, (2-amino-2-methyl-propyl)-methylamino or (2-(S)-amino-propyl)-methylamino,
or its pharmaceutically acceptable salt;
or, in a second embodiment (embodiment B), in combination with a DPP IV inhibitor selected from the group consisting of sitagliptin, vildagliptin, saxagliptin, alogliptin, denagliptin,
(2S)-1-{[2-(5-Methyl-2-phenyl-oxazol-4-yl)-ethylamino]-acetyl}-pyrrolidine-2-carbonitrile,
(2S)-1-{[1,1-Dimethyl-3-(4-pyridin-3-yl-imidazol-1-yl)-propylamino]-acetyl}-pyrrolidine-2-carbonitrile,
(S)-1-((2S,3S,11bS)-2-Amino-9,10-dimethoxy-1,3,4,7,11b-hexahydro-2H-pyrido[2,1-a]isoquinolin-3-yl)-4-fluoromethyl-pyrrolidin-2-one,
(3,3-Difluoropyrrolidin-1-yl)-((2S,4S)-4-(4-(pyrimidin-2-yl)piperazin-1-yl)pyrrolidin-2-yl)methanone,
(1((3S,4S)-4-amino-1-(4-(3,3-difluoropyrrolidin-1-yl)-1,3,5-triazin-2-yl)pyrrolidin-3-yl)-5,5-difluoropiperidin-2-one,
(2S,4S)-1-{2-[(3S,1R)-3-(1H-1,2,4-Triazol-1-ylmethyl)cyclopentylamino]-acetyl}-4-fluoropyrrolidine-2-carbonitrile, and
(R)-2-[6-(3-Amino-piperidin-1-yl)-3-methyl-2,4-dioxo-3,4-dihydro-2H-pyrimidin-1-ylmethyl]-4-fluoro-benzonitrile, or its pharmaceutically acceptable salt thereof.

According to another aspect of the invention, there is provided a method for preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity and metabolic syndrome in a patient in need thereof characterized in that a glucopyranosyl-substituted benzene derivative as defined hereinbefore and hereinafter is administered in combination or alternation with a DPP IV inhibitor as defined hereinbefore and hereinafter.

According to another aspect of the invention, there is provided a method for improving glycemic control and/or for reducing of fasting plasma glucose, of postprandial plasma glucose and/or of glycosylated hemoglobin HbA1c in a patient in need thereof characterized in that a glucopyranosyl-substituted benzene derivative as defined hereinbefore and hereinafter is administered in combination or alternation with a DPP IV inhibitor as defined hereinbefore and hereinafter.

The pharmaceutical composition according to this invention may also have valuable disease-modifying properties with respect to diseases or conditions related to impaired glucose tolerance (IGT), impaired fasting blood glucose (IFG), insulin resistance and/or metabolic syndrome.

According to another aspect of the invention, there is provided a method for preventing, slowing, delaying or reversing progression from impaired glucose tolerance (IGT), impaired fasting blood glucose (IFG), insulin resistance and/or from metabolic syndrome to type 2 diabetes mellitus in a patient in need thereof characterized in that a glucopyranosyl-substituted benzene derivative as defined hereinbefore and hereinafter is administered in combination or alternation with a DPP IV inhibitor as defined hereinbefore and hereinafter.

As by the use of a pharmaceutical composition according to this invention, an improvement of the glycemic control in patients in need thereof is obtainable, also those conditions and/or diseases related to or caused by an increased blood glucose level may be treated.

According to another aspect of the invention, there is provided a method for preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, arteriosclerosis, myocardial infarction, stroke and peripheral arterial occlusive disease, in a patient in need thereof characterized in that a glucopyranosyl-substituted benzene derivative as defined hereinbefore and hereinafter is administered in combination or alternation with a DPP IV inhibitor as defined hereinbefore and hereinafter. The term "tissue ischaemia" particularly comprises diabetic macroangiopathy, diabetic microangiopathy, impaired wound healing and diabetic ulcer.

By the administration of a pharmaceutical composition according to this invention and due to the SGLT2 inhibitory activity of the glucopyranosyl-substituted benzene derivative excessive blood glucose levels are not converted to insoluble storage forms, like fat, but excreted through the urine of the patient. Therefore, no gain in weight or even a reduction in body weight is the result.

According to another aspect of the invention, there is provided a method for reducing body weight or preventing an increase in body weight or facilitating a reduction in body weight in a patient in need thereof characterized in that a glucopyranosyl-substituted benzene derivative as defined hereinbefore and hereinafter is administered in combination or alternation with a DPP IV inhibitor as defined hereinbefore and hereinafter.

The pharmacological effect of the glucopyranosyl-substituted benzene derivative in the pharmaceutical composition according to this invention is independent of insulin. Therefore, an improvement of the glycemic control is possible without an additional strain on the pancreatic beta cells. By an administration of a pharmaceutical composition according to this invention a beta-cell degeneration and a decline of beta-cell functionality such as for example apoptosis or necrosis of pancreatic beta cells can be delayed or prevented. Furthermore, the functionality of pancreatic cells can be improved or restored, and the number and size of pancreatic beta cells increased. It may be shown that the differentiation status and hyperplasia of pancreatic beta-cells disturbed by hyperglycemia can be normalized by treatment with a pharmaceutical composition according to this invention.

According to another aspect of the invention, there is provided a method for preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion in a patient in need thereof characterized in that a glucopyranosyl-substituted benzene derivative as defined hereinbefore and hereinafter is administered in combination or alternation with a DPP IV inhibitor as defined hereinbefore and hereinafter.

By the administration of a combination or pharmaceutical composition according to the present invention, an abnormal accumulation of fat in the liver may be reduced or inhibited. Therefore, according to another aspect of the present invention, there is provided a method for preventing, slowing, delaying or treating diseases or conditions attributed to an abnormal accumulation of liver fat in a patient in need thereof characterized in that a glucopyranosyl-substituted benzene derivative as defined hereinbefore and hereinafter is administered in combination or alternation with a DPP IV inhibitor as defined hereinbefore and hereinafter. Diseases or conditions which are attributed to an abnormal accumulation of liver fat are particularly selected from the group consisting of general fatty liver, non-alcoholic fatty liver (NAFL), non-alcoholic steatohepatitis (NASH), hyperalimentation-induced fatty liver, diabetic fatty liver, alcoholic-induced fatty liver or toxic fatty liver.

As a result thereof, another aspect of the invention provides a method for maintaining and/or improving the insulin sensitivity and/or for treating or preventing hyperinsulinemia and/or insulin resistance in a patient in need thereof characterized in that a glucopyranosyl-substituted benzene derivative as defined hereinbefore and hereinafter is administered in combination or alternation with a DPP IV inhibitor as defined hereinbefore and hereinafter.

According to another aspect of the invention there is provided the use of a glucopyranosyl-substituted benzene derivative as defined hereinbefore and hereinafter for the manufacture of a medicament for preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity and metabolic syndrome; or improving glycemic control and/or for reducing of fasting plasma glucose, of postprandial plasma glucose and/or of glycosylated hemoglobin HbA1c; or preventing, slowing, delaying or reversing progression from impaired glucose tolerance (IGT), impaired fasting blood glucose (IFG), insulin resistance and/or from metabolic syndrome to type 2 diabetes mellitus; or preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, arteriosclerosis, myocardial infarction, stroke and peripheral arterial occlusive disease; or reducing body weight or preventing an increase in body weight or facilitating a reduction in body weight; or preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion; or preventing, slowing, delaying or treating diseases or conditions attributed to an abnormal accumulation of liver fat; or maintaining and/or improving the insulin sensitivity and/or for treating or preventing hyperinsulinemia and/or insulin resistance;

in a patient in need thereof characterized in that the glucopyranosyl-substituted benzene derivative is administered in combination or alternation with a DPP IV inhibitor as defined hereinbefore and hereinafter.

According to another aspect of the invention, there is provided the use of a DPP IV inhibitor as defined hereinbefore and hereinafter for the manufacture of a medicament for preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity and metabolic syndrome; or improving glycemic control and/or for reducing of fasting plasma glucose, of postprandial plasma glucose and/or of glycosylated hemoglobin HbA1c; or preventing, slowing, delaying or reversing progression from impaired glucose tolerance (IGT), impaired fasting blood glucose (IFG), insulin resistance and/or from metabolic syndrome to type 2 diabetes mellitus; or preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, arteriosclerosis, myocardial infarction, stroke and peripheral arterial occlusive disease; or reducing body weight or preventing an increase in body weight or facilitating a reduction in body weight; or preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion; or preventing, slowing, delaying or treating diseases or conditions attributed to an abnormal accumulation of liver fat; or maintaining and/or improving the insulin sensitivity and/or for treating or preventing hyperinsulinemia and/or insulin resistance;

in a patient in need thereof characterized in that the DPP IV inhibitor is administered in combination or alternation with a glucopyranosyl-substituted benzene derivative as defined hereinbefore and hereinafter.

According to another aspect of the invention, there is provided the use of a pharmaceutical composition according to the present invention for the manufacture of a medicament for a therapeutic and preventive method as described hereinbefore and hereinafter.

DEFINITIONS

The term "active ingredient" of a pharmaceutical composition according to the present invention means the glucopyranosyl-substituted benzene derivative and/or the DPP IV inhibitor according to the present invention.

The term "body mass index" or "BMI" of a human patient is defined as the weight in kilograms divided by the square of the height in meters, such that BMI has units of $kg/m^2$.

The term "overweight" is defined as the condition wherein the individual has a BMI greater than or 25 $kg/m^2$ and less than 30 $kg/m^2$. The terms "overweight" and "pre-obese" are used interchangeably.

The term "obesity" is defined as the condition wherein the individual has a BMI equal to or greater than 30 $kg/m^2$. According to a WHO definition the term obesity may be categorized as follows: the term "class I obesity" is the condition wherein the BMI is equal to or greater than 30 $kg/m^2$ but lower than 35 $kg/m^2$; the term "class II obesity" is the condition wherein the BMI is equal to or greater than 35 $kg/m^2$ but lower than 40 $kg/m^2$; the term "class III obesity" is the condition wherein the BMI is equal to or greater than 40 $kg/m^2$.

The term "visceral obesity" is defined as the condition wherein a waist-to-hip ratio of greater than or equal to 1.0 in men and 0.8 in women is measured. It defines the risk for insulin resistance and the development of pre-diabetes.

The term "abdominal obesity" is usually defined as the condition wherein the waist circumference is >40 inches or 102 cm in men, and is >35 inches or 94 cm in women. With regard to a Japanese ethnicity or Japanese patients abdominal obesity may be defined as waist circumference ≥85 cm in men and ≥90 cm in women (see e.g. investigating committee for the diagnosis of metabolic syndrome in Japan).

The term "euglycemia" is defined as the condition in which a subject has a fasting blood glucose concentration within the normal range, greater than 70 mg/dL (3.89 mmol/L) and less than 110 mg/dL (6.11 mmol/L). The word "fasting" has the usual meaning as a medical term.

The term "hyperglycemia" is defined as the condition in which a subject has a fasting blood glucose concentration above the normal range, greater than 110 mg/dL (6.11 mmol/L). The word "fasting" has the usual meaning as a medical term.

The term "hypoglycemia" is defined as the condition in which a subject has a blood glucose concentration below the normal range of 60 to 115 mg/dL (3.3 to 6.3 mmol/L).

The term "postprandial hyperglycemia" is defined as the condition in which a subject has a 2 hour postprandial blood glucose or serum glucose concentration greater than 200 mg/dL (11.11 mmol/L).

The term "impaired fasting blood glucose" or "IFG" is defined as the condition in which a subject has a fasting blood glucose concentration or fasting serum glucose concentration in a range from 100 to 125 mg/dl (i.e. from 5.6 to 6.9 mmol/l), in particular greater than 110 mg/dL and less than 126 mg/dl (7.00 mmol/L). A subject with "normal fasting glucose" has a fasting glucose concentration smaller than 100 mg/dl, i.e. smaller than 5.6 mmol/l.

The term "impaired glucose tolerance" or "IGT" is defined as the condition in which a subject has a 2 hour postprandial blood glucose or serum glucose concentration greater than 140 mg/dl (7.78 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dl (7.78 mmol/L).

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-to-hip ratio <1.0 (for men) or <0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford E S, et al. *JAMA*. (2002) 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. With this method, it is not possible to distinguish between hepatic and peripheral insulin resistance.

Furthermore, insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24: 362-5). Further reference is made to methods for the determination of the HOMA-index for insulin sensitivity (Matthews et al., *Diabetologia* 1985, 28:412-19), of the ratio of intact proinsulin to insulin (Forst et al., *Diabetes* 2003, 52(Suppl. 1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P, et al. Diabet Med 1992; 9:921-8):

HOMA-IR=[fasting serum insulin (pU/mL)]×[fasting plasma glucose (mmol/L)/22.5]

As a rule, other parameters are used in everyday clinical practice to assess insulin resistance. Preferably, the patient's triglyceride concentration is used, for example, as increased triglyceride levels correlate significantly with the presence of insulin resistance.

Patients with a predisposition for the development of IGT or IFG or type 2 diabetes are those having euglycemia with hyperinsulinemia and are by definition, insulin resistant. A typical patient with insulin resistance is usually overweight or obese. If insulin resistance can be detected, this is a particularly strong indication of the presence of pre-diabetes. Thus, it may be that in order to maintain glucose homoeostasis a person needs 2-3 times as much insulin as a healthy person, without this resulting in any clinical symptoms.

The methods to investigate the function of pancreatic beta-cells are similar to the above methods with regard to insulin sensitivity, hyperinsulinemia or insulin resistance: An improvement of beta-cell function can be measured for example by determining a HOMA-index for beta-cell function (Matthews et al., *Diabetologia* 1985, 28:412-19), the ratio of intact proinsulin to insulin (Forst et al., *Diabetes* 2003, 52(Suppl. 1): A459), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., *Eur J Clin Invest* 2001, 31: 380-81).

The term "pre-diabetes" is the condition wherein an individual is pre-disposed to the development of type 2 diabetes. Pre-diabetes extends the definition of impaired glucose tolerance to include individuals with a fasting blood glucose within the high normal range≥100 mg/dL (J. B. Meigs, et al. Diabetes 2003; 52:1475-1484) and fasting hyperinsulinemia (elevated plasma insulin concentration). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

Individuals likely to have insulin resistance are those who have two or more of the following attributes: 1) overweight or obese, 2) high blood pressure, 3) hyperlipidemia, 4) one or more 1$^{st}$ degree relative with a diagnosis of IGT or IFG or type 2 diabetes. Insulin resistance can be confirmed in these individuals by calculating the HOMA-IR score. For the purpose of this invention, insulin resistance is defined as the clinical condition in which an individual has a HOMA-IR score >4.0 or a HOMA-IR score above the upper limit of normal as defined for the laboratory performing the glucose and insulin assays.

The term "type 2 diabetes" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL (11.1 mmol/l) of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg, this is regarded as abnormal glucose tolerance.

The term "late stage type 2 diabetes mellitus" includes patients with a secondary drug failure, indication for insulin therapy and progression to micro- and macrovascular complications e.g. diabetic nephropathy, or coronary heart disease (CHD).

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks. Diabetic patients whose HbA1c value is consistently well adjusted by intensive diabetes treatment (i.e. <6.5% of the total haemoglobin in the sample), are significantly better protected against diabetic microangiopathy. For example, metformin on its own achieves an average improvement in the HbA1c value in the diabetic of the order of 1.0-1.5%. This reduction of the HbA1C value is not sufficient in all diabetics to achieve the desired target range of <6.5% and preferably <6% HbA1c.

The "metabolic syndrome", also called "syndrome X" (when used in the context of a metabolic disorder), also called the "dysmetabolic syndrome" is a syndrome complex with the cardinal feature being insulin resistance (Laaksonen D E, et al. *Am J Epidemiol* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference >40 inches or 102 cm in men, and >35 inches or 94 cm in women; or with regard to a Japanese ethnicity or Japanese patients defined as waist circumference ≥85 cm in men and ≥90 cm in women;
2. Triglycerides: ≥150 mg/dL
3. HDL-cholesterol <40 mg/dL in men
4. Blood pressure ≥130/85 mm Hg (SBP ≥130 or DBP ≥85)
5. Fasting blood glucose ≥110 mg/dL The NCEP definitions have been validated (Laaksonen D E, et al. *Am J Epidemiol*. (2002) 156:1070-7). Triglycerides and HDL cholesterol in the blood can also be determined by standard methods in medical analysis and are described for example in Thomas L (Editor): "Labor and Diagnose", TH-Books Verlagsgesellschaft mbH, Frankfurt/Main, 2000.

According to a commonly used definition, hypertension is diagnosed if the systolic blood pressure (SBP) exceeds a value of 140 mm Hg and diastolic blood pressure (DBP) exceeds a value of 90 mm Hg. If a patient is suffering from manifest diabetes it is currently recommended that the systolic blood pressure be reduced to a level below 130 mm Hg and the diastolic blood pressure be lowered to below 80 mm Hg.

The terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy.

The terms "prophylactically treating", "preventively treating" and "preventing" are used interchangeably and comprise a treatment of patients at risk to develop a condition mentioned hereinbefore, thus reducing said risk.

DETAILED DESCRIPTION

The aspects according to the present invention, in particular the pharmaceutical compositions, methods and uses, refer to glucopyranosyl-substituted benzene derivatives of the formula (I) as defined hereinbefore and hereinafter.

Preferably $R^1$ denotes chloro or cyano; in particular chloro.
Preferably $R^2$ denotes H.
Preferably $R^3$ denotes ethyl, cyclopropyl, ethinyl, (R)-tetrahydrofuran-3-yloxy or (S)-tetrahydrofuran-3-yloxy. Even more preferably $R^3$ denotes cyclopropyl, ethinyl, (R)-tetrahydrofuran-3-yloxy or (S)-tetrahydrofuran-3-yloxy.

Preferred glucopyranosyl-substituted benzene derivatives are selected from the group of compounds (1) to (10):
(1) 6-(4-Ethylbenzyl)-4-(β-D-glucopyranos-1-yl)-2-methoxy-benzonitrile
(2) 2-(4-Ethylbenzyl)-4-(β-D-glucopyranos-1-yl)-5-methoxy-benzonitrile
(3) 1-Cyano-2-(4-ethylbenzyl)-4-(β-D-glucopyranos-1-yl)-5-methyl-benzene
(4) 2-(4-Ethylbenzyl)-4-(β-D-glucopyranos-1-yl)-5-hydroxy-benzonitrile
(5) 2-(4-Ethyl-benzyl)-4-(β-D-glucopyranos-1-yl)-benzonitrile
(6) 2-(4-Cyclopropyl-benzyl)-4-(β-D-glucopyranos-1-yl)-benzonitrile
(7) 1-chloro-4-(β-D-glucopyranos-1-yl)-2-(4-ethynyl-benzyl)-benzene
(8) 1-chloro-4-(β-D-glucopyranos-1-yl)-2-[4-((R)-tetrahydrofuran-3-yloxy)-benzyl]-benzene
(9) 1-chloro-4-(β-D-glucopyranos-1-yl)-2-[4-((S)-tetrahydrofuran-3-yloxy)-benzyl]-benzene
(10) 1-Methyl-2-[4-((R)-tetrahydrofuran-3-yloxy)-benzyl]-4-(β-D-glucopyranos-1-yl)-benzene
(11) 1-Methyl-2-[4-((S)-tetrahydrofuran-3-yloxy)-benzyl]-4-(β-D-glucopyranos-1-yl)-benzene Even more preferred glucopyranosyl-substituted benzene derivative are selected from the compounds (6), (7), (8), (9) and (11).

According to this invention, it is to be understood that the definitions of the above listed glucopyranosyl-substituted benzene derivatives also comprise their hydrates, solvates and polymorphic forms thereof. With regard to the preferred compound (7) an advantageous crystalline form is described in the international patent application WO 2007/028814 which hereby is incorporated herein in its entirety. With regard to the preferred compound (8), an advantageous crystalline form is described in the international patent application WO 2006/117360 which hereby is incorporated herein in its entirety. With regard to the preferred compound (9) an advantageous crystalline form is described in the international patent application WO 2006/117359 which hereby is incorporated herein in its entirety. With regard to the preferred compound (II) an advantageous crystalline form is described in the international patent application WO 2008/049923 which hereby is incorporated herein in its entirety. These crystalline forms possess good solubility properties which enable a good bioavailability of the SGLT2 inhibitor. Furthermore, the crystalline forms are physico-chemically stable and thus provide a good shelf-life stability.

The aspects according to the present invention, in particular the pharmaceutical compositions, methods and uses, refer to a DPP IV inhibitor as defined hereinbefore and hereinafter, or prodrugs thereof, or pharmaceutically acceptable salts thereof.

Regarding the first embodiment (embodiment A), preferred DPP IV inhibitors are any or all of the following compounds and their pharmaceutically acceptable salts:

(A): 1-[(4-methyl-quinazolin-2-yl)methyl]-3-methyl-7-(2-butyn-1-yl)-8-(3-(R)-amino-piperidin-1-yl)-xanthine (cf. WO 2004/018468, Example 2(142)):

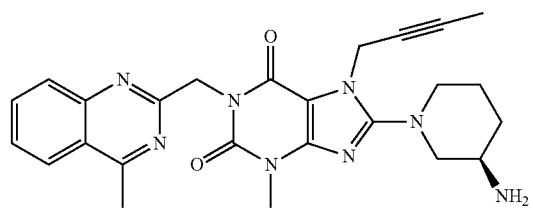 [SMILES: CC#CCn1c(N2CCC[C@@H](N)C2)nc2c1c(=O)n(Cc1nc(C)c3ccccc3n1)c(=O)n2C]

(B): 1-[([1,5]naphthyridin-2-yl)methyl]-3-methyl-7-(2-butyn-1-yl)-8-((R)-3-amino-piperidin-1-yl)-xanthine (cf. WO 2004/018468, Example 2(252)):

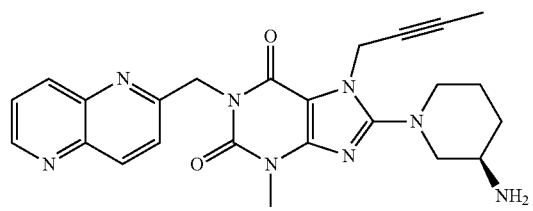 [SMILES: CC#CCn1c(N2CCC[C@@H](N)C2)nc2c1c(=O)n(Cc1ccc3ncccc3n1)c(=O)n2C]

(C): 1-[(quinazolin-2-yl)methyl]-3-methyl-7-(2-butyn-1-yl)-8-((R)-3-amino-piperidin-1-yl)-xanthine (cf. WO 2004/018468, Example 2(80)):

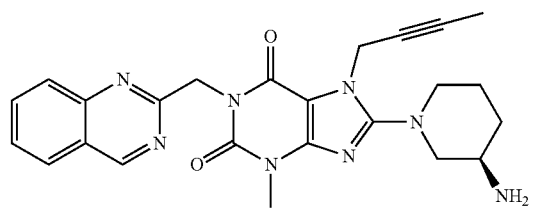 [SMILES: CC#CCn1c(N2CCC[C@@H](N)C2)nc2c1c(=O)n(Cc1ncc3ccccc3n1)c(=O)n2C]

(D): 2-((R)-3-amino-piperidin-1-yl)-3-(but-2-ynyl)-5-(4-methyl-quinazolin-2-ylmethyl)-3.5-dihydro-imidazo[4,5-c]pyridazin-4-one (cf. WO 2004/050658, Example 136):

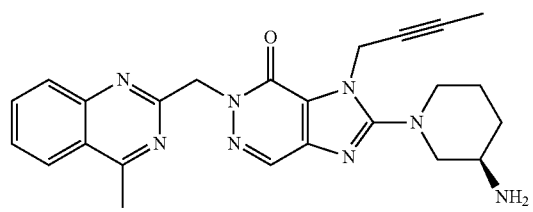 [SMILES: CC#CCn1c(N2CCC[C@@H](N)C2)nc2cnn(Cc3nc(C)c4ccccc4n3)c(=O)c21]

(E): 1-[(4-methyl-quinazolin-2-yl)methyl]-3-methyl-7-(2-butyn-1-yl)-8-[(2-amino-2-methyl-propyl)-methylamino]-xanthine (cf. WO 2006/029769, Example 2(1)):

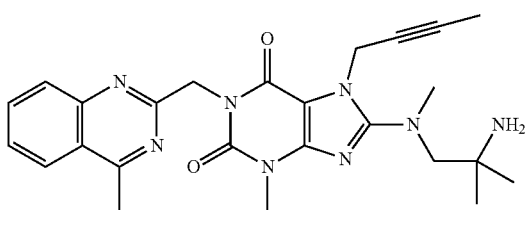 [SMILES: CC#CCn1c(N(C)CC(C)(C)N)nc2c1c(=O)n(Cc1nc(C)c3ccccc3n1)c(=O)n2C]

(F): 1-[(3-cyano-quinolin-2-yl)methyl]-3-methyl-7-(2-butyn-1-yl)-8-((R)-3-amino-piperidin-1-yl)-xanthine (cf. WO 2005/085246, Example 1(30)):

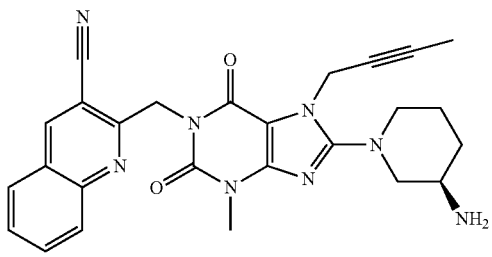 [SMILES: CC#CCn1c(N2CCC[C@@H](N)C2)nc2c1c(=O)n(Cc1nc3ccccc3cc1C#N)c(=O)n2C]

(G): 1-(2-cyano-benzyl)-3-methyl-7-(2-butyn-1-yl)-8-((R)-3-amino-piperidin-1-yl)-xanthine (cf. WO 2005/085246, Example 1(39)):

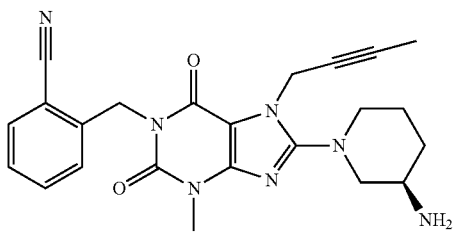

(H): 1-[(4-methyl-quinazolin-2-yl)methyl]-3-methyl-7-(2-butyn-1-yl)-8-[(S)-(2-amino-propyl)-methylamino]-xanthine (cf. WO 2006/029769, Example 2(4)):

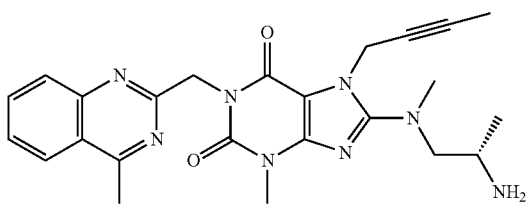 [SMILES: CC#CCn1c(N(C)C[C@H](C)N)nc2c1c(=O)n(Cc1nc(C)c3ccccc3n1)c(=O)n2C]

(I): 1-[(3-cyano-pyridin-2-yl)methyl]-3-methyl-7-(2-butyn-1-yl)-8-((R)-3-amino-piperidin-1-yl)-xanthine (cf. WO 2005/085246, Example 1(52)):

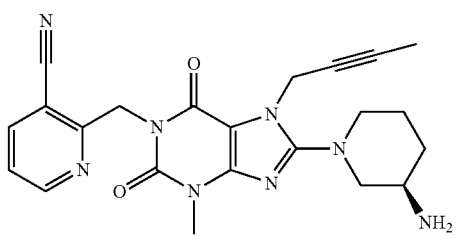 [SMILES: CC#CCn1c(N2CCC[C@@H](N)C2)nc2c1c(=O)n(Cc1ncccc1C#N)c(=O)n2C]

(J): 1-[(4-methyl-pyrimidin-2-yl)methyl]-3-methyl-7-(2-butyn-1-yl)-8-((R)-3-amino-piperidin-1-yl)-xanthine (cf. WO 2005/085246, Example 1(81)):

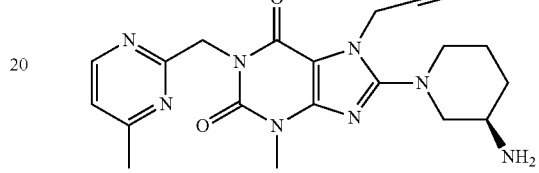

(K): 1-[(4,6-dimethyl-pyrimidin-2-yl)methyl]-3-methyl-7-(2-butyn-1-yl)-8-((R)-3-amino-piperidin-1-yl)-xanthine (cf. WO 2005/085246, Example 1(82)):

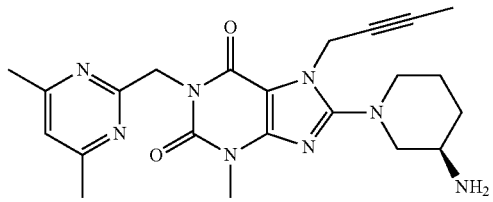 [SMILES: CC#CCn1c(N2CCC[C@@H](N)C2)nc2c1c(=O)n(Cc1nc(C)cc(C)n1)c(=O)n2C]

(L): 1-[(quinoxalin-6-yl)methyl]-3-methyl-7-(2-butyn-1-yl)-8-((R)-3-amino-piperidin-1-yl)-xanthine (cf. WO 2005/085246, Example 1(83)):

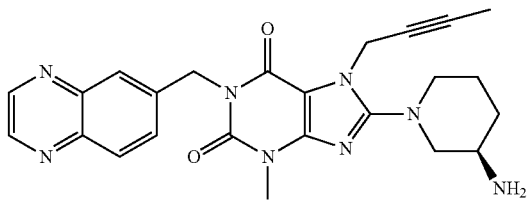 [SMILES: CC#CCn1c(N2CCC[C@@H](N)C2)nc2c1c(=O)n(Cc1ccc3nccnc3c1)c(=O)n2C]

These DPP IV inhibitors are distinguished from structurally comparable DPP IV inhibitors, as they combine exceptional potency and a long-lasting effect with favourable pharmacological properties, receptor selectivity and a favourable side-effect profile or bring about unexpected therapeutic advantages or improvements when combined with other pharmaceutical active substances. Their preparation is disclosed in the publications mentioned.

Regarding the second embodiment (embodiment B), preferred DPP IV inhibitors are selected from the group consisting of sitagliptin, vildagliptin, saxagliptin and alogliptin.

According to this invention it is to be understood that the definitions of the above listed DPP IV inhibitors also comprise their pharmaceutically acceptable salts as well as hydrates, solvates and polymorphic forms thereof. With respect to salts, hydrates and polymorphic forms thereof, particular reference is made to those which are referred to hereinabove and hereinbelow.

The pharmaceutical compositions, methods and uses according to this invention most preferably relate to combinations which are selected from the Table 1.

TABLE 1

| No. | Compound No. of the SGLT2 inhibitor | DPP IV Inhibitor |
|---|---|---|
| 1 | (1) | (A) |
| 2 | (1) | (B) |
| 3 | (1) | (C) |
| 4 | (1) | (D) |
| 5 | (1) | (E) |
| 6 | (1) | (F) |
| 7 | (1) | (G) |
| 8 | (1) | (H) |
| 9 | (1) | (I) |
| 10 | (1) | (J) |
| 11 | (1) | (K) |
| 12 | (1) | (L) |
| 13 | (2) | (A) |
| 14 | (2) | (B) |
| 15 | (2) | (C) |
| 16 | (2) | (D) |
| 17 | (2) | (E) |
| 18 | (2) | (F) |
| 19 | (2) | (G) |
| 20 | (2) | (H) |
| 21 | (2) | (I) |
| 22 | (2) | (J) |
| 23 | (2) | (K) |
| 24 | (2) | (L) |
| 25 | (3) | (A) |
| 26 | (3) | (B) |
| 27 | (3) | (C) |
| 28 | (3) | (D) |
| 29 | (3) | (E) |
| 30 | (3) | (F) |
| 31 | (3) | (G) |
| 32 | (3) | (H) |
| 33 | (3) | (I) |
| 34 | (3) | (J) |
| 35 | (3) | (K) |
| 36 | (3) | (L) |
| 37 | (4) | (A) |
| 38 | (4) | (B) |
| 39 | (4) | (C) |
| 40 | (4) | (D) |
| 41 | (4) | (E) |
| 42 | (4) | (F) |
| 43 | (4) | (G) |
| 44 | (4) | (H) |
| 45 | (4) | (I) |
| 46 | (4) | (J) |
| 47 | (4) | (K) |
| 48 | (4) | (L) |
| 49 | (5) | (A) |
| 50 | (5) | (B) |
| 51 | (5) | (C) |
| 52 | (5) | (D) |
| 53 | (5) | (E) |
| 54 | (5) | (F) |
| 55 | (5) | (G) |
| 56 | (5) | (H) |
| 57 | (5) | (I) |
| 58 | (5) | (J) |
| 59 | (5) | (K) |
| 60 | (5) | (L) |
| 61 | (6) | (A) |
| 62 | (6) | (B) |
| 63 | (6) | (C) |
| 64 | (6) | (D) |
| 65 | (6) | (E) |
| 66 | (6) | (F) |
| 67 | (6) | (G) |
| 68 | (6) | (H) |
| 69 | (6) | (I) |
| 70 | (6) | (J) |
| 71 | (6) | (K) |
| 72 | (6) | (L) |
| 73 | (7) | (A) |
| 74 | (7) | (B) |
| 75 | (7) | (C) |
| 76 | (7) | (D) |
| 77 | (7) | (E) |
| 78 | (7) | (F) |
| 79 | (7) | (G) |
| 80 | (7) | (H) |
| 81 | (7) | (I) |
| 82 | (7) | (J) |
| 83 | (7) | (K) |
| 84 | (7) | (L) |
| 85 | (8) | (A) |
| 86 | (8) | (B) |
| 87 | (8) | (C) |
| 88 | (8) | (D) |
| 89 | (8) | (E) |
| 90 | (8) | (F) |
| 91 | (8) | (G) |
| 92 | (8) | (H) |
| 93 | (8) | (I) |
| 94 | (8) | (J) |
| 95 | (8) | (K) |
| 96 | (8) | (L) |
| 97 | (9) | (A) |
| 98 | (9) | (B) |
| 99 | (9) | (C) |
| 100 | (9) | (D) |
| 101 | (9) | (E) |
| 102 | (9) | (F) |
| 103 | (9) | (G) |
| 104 | (9) | (H) |
| 105 | (9) | (I) |
| 106 | (9) | (J) |
| 107 | (9) | (K) |
| 108 | (9) | (L) |
| 109 | (10) | (A) |
| 110 | (10) | (B) |
| 111 | (10) | (C) |
| 112 | (10) | (D) |
| 113 | (10) | (E) |
| 114 | (10) | (F) |
| 115 | (10) | (G) |
| 116 | (10) | (H) |
| 117 | (10) | (I) |
| 118 | (10) | (J) |
| 119 | (10) | (K) |
| 120 | (10) | (L) |
| 121 | (11) | (A) |
| 122 | (11) | (B) |
| 123 | (11) | (C) |
| 124 | (11) | (D) |
| 125 | (11) | (E) |
| 126 | (11) | (F) |
| 127 | (11) | (G) |
| 128 | (11) | (H) |
| 129 | (11) | (I) |
| 130 | (11) | (J) |
| 131 | (11) | (K) |
| 132 | (11) | (L) |
| 133 | (1) | sitagliptin |
| 134 | (1) | vildagliptin |
| 135 | (1) | saxagliptin |
| 136 | (1) | alogliptin |
| 137 | (2) | sitagliptin |
| 138 | (2) | vildagliptin |
| 139 | (2) | saxagliptin |
| 140 | (3) | alogliptin |
| 141 | (3) | sitagliptin |
| 142 | (3) | vildagliptin |
| 143 | (3) | saxagliptin |
| 144 | (3) | alogliptin |

TABLE 1-continued

| No. | Compound No. of the SGLT2 inhibitor | DPP IV Inhibitor |
|---|---|---|
| 145 | (4) | sitagliptin |
| 146 | (4) | vildagliptin |
| 147 | (4) | saxagliptin |
| 148 | (4) | alogliptin |
| 149 | (5) | sitagliptin |
| 150 | (5) | vildagliptin |
| 151 | (5) | saxagliptin |
| 152 | (5) | alogliptin |
| 153 | (6) | sitagliptin |
| 154 | (6) | vildagliptin |
| 155 | (6) | saxagliptin |
| 156 | (6) | alogliptin |
| 157 | (7) | sitagliptin |
| 158 | (7) | vildagliptin |
| 159 | (7) | saxagliptin |
| 160 | (7) | alogliptin |
| 161 | (8) | sitagliptin |
| 162 | (8) | vildagliptin |
| 163 | (8) | saxagliptin |
| 164 | (8) | alogliptin |
| 165 | (9) | sitagliptin |
| 166 | (9) | vildagliptin |
| 167 | (9) | saxagliptin |
| 168 | (9) | alogliptin |
| 169 | (10) | sitagliptin |
| 170 | (10) | vildagliptin |
| 171 | (10) | saxagliptin |
| 172 | (10) | alogliptin |
| 173 | (11) | sitagliptin |
| 174 | (11) | vildagliptin |
| 175 | (11) | saxagliptin |
| 176 | (11) | alogliptin |

Among the combinations No. 1-176 according to the present invention listed in Table 1, combinations No. 1, 13, 25, 37, 49, 61, 73, 85, 97, 109, 121, and 133-176, in particular 61, 73, 85, 97, 121, 153 to 168 and 173 to 176, even more preferably 97, 165, 166, 167 and 168 are to be emphasized.

The combination of a glucopyranosyl-substituted benzene derivative and a DPP IV inhibitor according to this invention significantly improves the glycemic control, in particular in patients as described hereinafter, compared with a monotherapy using either the glucopyranosyl-substituted benzene derivative or the DPP IV inhibitor. The improved glycemic control is determined as an increased lowering of blood glucose and an increased reduction of HbA1c. With monotherapy in a patient, in particular in patients as described hereinafter, the glycemic control can usually not be further improved significantly by an administration of the drug above a certain highest dose. In addition, a long term treatment using a highest dose may be unwanted in view of potential side effects. Therefore, a full glycemic control cannot be achieved in all patients via a monotherapy using either the glucopyranosyl-substituted benzene derivative or the DPP IV inhibitor. In such patients a progression of the diabetes mellitus may continue and complications associated with diabetes mellitus may occur, such as macrovascular complications. The pharmaceutical composition as well as the methods according to the present invention allow a reduction of the HbA1c value to a desired target range, for example <7% and preferably <6.5%, for a higher number of patients compared with a corresponding monotherapy.

In addition, the combination of a glucopyranosyl-substituted benzene derivative and a DPP IV inhibitor according to this invention allows a reduction in the dose of either the glucopyranosyl-substituted benzene derivative or the DPP IV inhibitor or of both active ingredients. A dose reduction is beneficial for patients which otherwise would potentially suffer from side effects in a monotherapy using a higher dose of either the glucopyranosyl-substituted benzene derivative or the DPP IV inhibitor. Therefore, the pharmaceutical composition as well as the methods according to the present invention, show less side effects, thereby making the therapy more tolerable and improving the patients compliance with the treatment.

A monotherapy using a DPP IV inhibitor according to the present invention is not independent from the insulin secretory capacity or the insulin sensitivity of a patient. On the other hand, a treatment with the administration of a glucopyranosyl-substituted benzene derivative according the present invention does not depend on the insulin secretory capacity or the insulin sensitivity of the patient. Therefore, any patient independent of the prevailing insulin levels or insulin resistance and/or hyperinsulinemia may benefit from a therapy using a combination of a glucopyranosyl-substituted benzene derivative and a DPP IV inhibitor according to this invention. Independent of their prevailing insulin levels or their insulin resistance or hyperinsulinemia these patients can still be treated with the DPP IV inhibitor because of the combined or alternate administration of the glucopyranosyl-substituted benzene derivative.

A DPP IV inhibitor according to the present invention is able—via the increases in active GLP-1 levels—to reduce the glucagon secretion in a patient. This will therefore limit the hepatic glucose production. Furthermore, the elevated active GLP-1 levels produced by the DPP IV inhibitor will have beneficial effects on beta-cell regeneration and neogenesis. All these features of DPP IV inhibitors render a combination with a glucopyranosyl-substituted benzene derivative quite useful and therapeutically relevant.

When this invention refers to patients requiring treatment or prevention, it relates primarily to treatment and prevention in humans, but the pharmaceutical composition may also be used accordingly in veterinary medicine on mammals.

As described hereinbefore by the administration of the pharmaceutical composition according to this invention and in particular in view of the high SGLT2 inhibitory activity of the glucopyranosyl-substituted benzene derivative therein, excessive blood glucose is excreted through the urine of the patient, so that no gain in weight or even a reduction in body weight may result. Therefore, a treatment or prophylaxis according to this invention is advantageously suitable in those patients in need of such treatment or prophylaxis who are diagnosed of one or more of the conditions selected from the group consisting of overweight, class I obesity, class II obesity, class III obesity, visceral obesity and abdominal obesity or for those individuals in which a weight increase is contraindicated.

The pharmaceutical composition according to this invention and in particular the glucopyranosyl-substituted benzene derivative therein exhibits a very good efficacy with regard to glycemic control, in particular in view of a reduction of fasting plasma glucose, postprandial plasma glucose and/or glycosylated hemoglobin (HbA1c). By administering a pharmaceutical composition according to this invention, a reduction of HbA1c equal to or greater than preferably 0.5%, even more preferably equal to or greater than 1.0% can be achieved and the reduction is particularly in the range from 1.0% to 1.5%.

Furthermore, the method and/or use according to this invention is advantageously applicable in those patients who show one, two or more of the following conditions:
(a) a fasting blood glucose or serum glucose concentration greater than 110 mg/dL, in particular greater than 125 mg/dL;

(b) a postprandial plasma glucose equal to or greater than 140 mg/dL;
(c) an HbA1c value equal to or greater than 6.5%, in particular equal to or greater than 8.0%.

The present invention also discloses the use of the pharmaceutical composition for improving glycemic control in patients having type 2 diabetes or showing first signs of pre-diabetes. Thus, the invention also includes diabetes prevention. If therefore a pharmaceutical composition according to this invention is used to improve the glycemic control as soon as one of the above-mentioned signs of pre-diabetes is present, the onset of manifest type 2 diabetes mellitus can be delayed or prevented.

Furthermore, the pharmaceutical composition according to this invention is particularly suitable in the treatment of patients with insulin dependency, i.e. in patients who are treated or otherwise would be treated or need treatment with an insulin or a derivative of insulin or a substitute of insulin or a formulation comprising an insulin or a derivative or substitute thereof. These patients include patients with diabetes type 2 and patients with diabetes type 1.

It can be found that by using a pharmaceutical composition according to this invention, an improvement of the glycemic control can be achieved even in those patients who have insufficient glycemic control in particular despite treatment with an antidiabetic drug, for example despite maximal tolerated dose of oral monotherapy with either metformin or a SGLT2 inhibitor, in particular a SGLT2 inhibitor according to this invention, or a DPP IV inhibitor, in particular a DPP IV inhibitor according to this invention. A maximal tolerated dose with regard to metformin is for example 850 mg three times a day or any equivalent thereof. A maximal tolerated dose with regard to a SGLT2 inhibitor according to this invention, in particular with regard to the compounds (6), (7), (8), (9) or (11), is for example 100 mg, preferably 50 mg or even 30 mg once per day or any equivalent thereof. A maximal tolerated dose with regard to a DPP IV inhibitor according to this invention, in particular with regard to the compound (A) (1-[(4-methyl-quinazolin-2-yl)methyl]-3-methyl-7-(2-butyn-1-yl)-8-(3-(R)-amino-piperidin-1-yl)-xanthine), is for example 10 mg once daily or any equivalent thereof. A maximal tolerated dose with regard to a DPP IV inhibitor according to his invention is for example Sitagliptin 100 mg once daily or any equivalent thereof. In the scope of the present invention, the term "insufficient glycemic control" means a condition wherein patients show HbA1c values above 6.5%, in particular above 8%.

Therefore, according to a preferred embodiment of the present invention, there is provided a method for improving glycemic control and/or for reducing of fasting plasma glucose, of postprandial plasma glucose and/or of glycosylated hemoglobin HbA1c in a patient in need thereof who is diagnosed with impaired glucose tolerance (IGT), impaired fasting blood glucose (IFG) with insulin resistance, with metabolic syndrome and/or with type 2 or type 1 diabetes mellitus characterized in that a glucopyranosyl-substituted benzene derivative as defined hereinbefore and hereinafter is administered in combination or alternation with a DPP IV inhibitor as defined hereinbefore and hereinafter.

The lowering of the blood glucose level by the administration of a glucopyranosyl-substituted benzene derivative according to this invention is insulin-independent. Therefore, a pharmaceutical composition according to this invention is particularly suitable in the treatment of patients who are diagnosed having one or more of the following conditions insulin resistance,
hyperinsulinemia,
pre-diabetes,
type 2 diabetes mellitus, particular having a late stage type 2 diabetes mellitus,
type 1 diabetes mellitus.

Furthermore, a pharmaceutical composition according to this invention is particularly suitable in the treatment of patients who are diagnosed having one or more of the following conditions
(a) obesity (including class I, II and/or III obesity), visceral obesity and/or abdominal obesity,
(b) triglyceride blood level ≥150 mg/dL,
(c) HDL-cholesterol blood level <40 mg/dL in female patients and <50 mg/dL in male patients,
(d) a systolic blood pressure ≥130 mm Hg and a diastolic blood pressure ≥85 mm Hg,
(e) a fasting blood glucose level ≥110 mg/dL.

It is assumed that patients diagnosed with impaired glucose tolerance (IGT), impaired fasting blood glucose (IFG), with insulin resistance and/or with metabolic syndrome suffer from an increased risk of developing a cardiovascular disease, such as for example myocardial infarction, coronary heart disease, heart insufficiency, thromboembolic events. A glycemic control according to this invention may result in a reduction of the cardiovascular risks.

A pharmaceutical composition according to this invention, in particular due to the glucopyranosyl-substituted benzene derivative therein, exhibits a good safety profile. Therefore, a treatment or prophylaxis according to this invention is advantageously possible in those patients for which the monotherapy with another antidiabetic drug, such as for example metformin, is contraindicated and/or who have an intolerance against such drugs at therapeutic doses. In particular, a treatment or prophylaxis according to this invention may be advantageously possible in those patients showing or having an increased risk for one or more of the following disorders: renal insufficiency or diseases, cardiac diseases, cardiac failure, hepatic diseases, pulmonal diseases, catabolytic states and/or danger of lactate acidosis, or female patients being pregnant or during lactation.

Furthermore, it can be found that the administration of a pharmaceutical composition according to this invention results in no risk or in a low risk of hypoglycemia. Therefore, a treatment or prophylaxis according to this invention is also advantageously possible in those patients showing or having an increased risk for hypoglycemia.

A pharmaceutical composition according to this invention is particularly suitable in the long term treatment or prophylaxis of the diseases and/or conditions as described hereinbefore and hereinafter, in particular in the long term glycemic control in patients with type 2 diabetes mellitus.

The term "long term" as used hereinbefore and hereinafter indicates a treatment of or administration in a patient within a period of time longer than 12 weeks, preferably longer than 25 weeks, even more preferably longer than 1 year.

Therefore, a particularly preferred embodiment of the present invention provides a method for therapy, preferably oral therapy, for improvement, especially long term improvement, of glycemic control in patients with type 2 diabetes mellitus, especially in patients with late stage type 2 diabetes mellitus, in particular in patients additionally diagnosed of overweight, obesity (including class I, class II and/or class III obesity), visceral obesity and/or abdominal obesity.

The effects mentioned above are observed both, when the glucopyranosyl-substituted benzene derivative and the DPP IV inhibitor are administered in combination, for example simultaneously, and when they are administered in alternation, for example successively in separate formulations.

It will be appreciated that the amount of the pharmaceutical composition according to this invention to be administered to the patient and required for use in treatment or prophylaxis according to the present invention will vary with the route of administration, the nature and severity of the condition for which treatment or prophylaxis is required, the age, weight and condition of the patient, concomitant medication and will be ultimately at the discretion of the attendant physician. In general, however, the glucopyranosyl-substituted benzene derivative according to this invention and the DPP IV inhibitor are included in the pharmaceutical composition or dosage form in an amount sufficient that by their administration in combination or alternation the glycemic control in the patient to be treated is improved.

In the following preferred ranges of the amount of glucopyranosyl-substituted benzene derivative and of the DPP IV inhibitor to be employed in the pharmaceutical composition and the methods and uses according to this invention are described. These ranges refer to the amounts to be administered per day with respect to an adult patient and can be adapted accordingly with regard to an administration 2, 3, 4 or more times daily and with regard to other routes of administration and with regard to the age of the patient.

Within the scope of the present invention, the pharmaceutical composition is preferably administered orally. Other forms of administration are possible and described hereinafter. Preferably the dosage form comprising the glucopyranosyl-substituted benzene derivative is administered orally. The route of administration of the DPP IV inhibitor is oral or usually well known.

In general, the amount of the glucopyranosyl-substituted benzene derivative in the pharmaceutical composition and methods according to this invention is preferably in the range from 1/5 to 1/1 of the amount usually recommended for a monotherapy using said glucopyranosyl-substituted benzene derivative. Advantageously, the combination therapy according to the present invention utilizes lower dosages of the individual glucopyranosyl-substituted benzene derivative or of the individual DPP IV inhibitor used in monotherapy or used in conventional therapeutics, thus avoiding possible toxicity and adverse side effects incurred when those agents are used as monotherapies.

The amount of the glucopyranosyl-substituted benzene derivative is preferably in the range from 0.5 mg to 200 mg, even more preferably from 1 to 100 mg, most preferably from 5 to 50 mg per day for a human being, for example for approximately 70 kg body weight. The oral administration is preferred. Therefore, a pharmaceutical composition may comprise the hereinbefore mentioned amounts for once daily administration and from 0.25 mg to 100 mg, even more preferably from 0.5 to 50 mg, most preferably from 2.5 to 25 mg for twice daily administration. Particular dosage strengths (e.g. per tablet or capsule) are for example 5, 10, 15, 20, 25 or 50 mg of the compound (6), (7), (8), (9) or (11), in particular of the compound (9).

In general, the amount of the DPP IV inhibitor in the pharmaceutical composition and methods according to this invention is preferably in the range from 1/5 to 1/1 of the amount usually recommended for a monotherapy using said DPP IV inhibitor.

With respect to the first embodiment (embodiment A), the dosage typically required of the DPP IV inhibitors mentioned herein in embodiment A when administered intravenously is 0.1 mg to 10 mg, preferably 0.25 mg to 5 mg, and when administered orally 0.5 mg to 100 mg, preferably 2.5 mg to 50 mg, or 0.5 mg to 10 mg, more preferably 2.5 mg to 10 mg or 1 mg to 5 mg, in each case 1 to 4 times a day. Thus, the dosage required of the compound (A) (1-[(4-methyl-quinazolin-2-yl)methyl]-3-methyl-7-(2-butyn-1-yl)-8-(3-(R)-amino-piperidin-1-yl)-xanthine) when administered orally is 0.5 mg to 10 mg per patient per day, preferably 2.5 mg to 10 mg per patient per day (more preferably 5 mg to 10 mg per patient per day) or 1 mg to 5 mg per patient per day.

A dosage form prepared with a pharmaceutical composition comprising a DPP IV inhibitor mentioned herein in embodiment A contain the active ingredient in a dosage range of 0.1-100 mg, in particular 0.5 to 10 mg. Thus, particular dosage strengths of the compound (A) (1-[(4-methyl-quinazolin-2-yl)methyl]-3-methyl-7-(2-butyn-1-yl)-8-(3-(R)-amino-piperidin-1-yl)-xanthine) are 0.5 mg, 1 mg, 2.5 mg, 5 mg and 10 mg, more particular dosage strengths thereof are 1 mg, 2.5 mg and 5 mg.

With respect to the second embodiment (embodiment B), the doses of DPP IV inhibitors mentioned herein in embodiment B to be administered to mammals, for example human beings, of, for example, approximately 70 kg body weight, may be generally from about 0.5 mg to about 350 mg, for example from about 10 mg to about 250 mg, preferably 20-200 mg, more preferably 20-100 mg, of the active moiety per person per day, or from about 0.5 mg to about 20 mg, preferably 2.5-10 mg, per person per day, divided preferably into 1 to 4 single doses which may, for example, be of the same size. Single dosage strengths comprise, for example, 10, 25, 40, 50, 75, 100, 150 and 200 mg of the DPP IV inhibitor active moiety.

A dosage strength of the DPP IV inhibitor sitagliptin is usually between 25 and 200 mg of the active moiety. A recommended dose of sitagliptin is 100 mg calculated for the active moiety (free base anhydrate) once daily. Unit dosage strengths of sitagliptin free base anhydrate (active moiety) are 25, 50, 75, 100, 150 and 200 mg. Particular unit dosage strengths of sitagliptin (e.g. per tablet) are 25, 50 and 100 mg. An equivalent amount of sitagliptin phosphate monohydrate to the sitagliptin free base anhydrate is used in the pharmaceutical compositions, namely, 32.13, 64.25, 96.38, 128.5, 192.75, and 257 mg, respectively. Adjusted dosages of 25 and 50 mg sitagliptin are used for patients with renal failure.

A dosage range of the DPP IV inhibitor vildagliptin is usually between 10 and 150 mg daily, in particular between 25 and 150 mg, 25 and 100 mg or 25 and 50 mg or 50 and 100 mg daily. Particular examples of daily oral dosage are 25, 30, 35, 45, 50, 55, 60, 80, 100 or 150 mg. In a more particular aspect, the daily administration of vildagliptin is between 25 and 150 mg or between 50 and 100 mg. In another more particular aspect, the daily administration of vildagliptin is 50 or 100 mg. The application of the active ingredient may occur up to three times a day, preferably one or two times a day. Particular dosage forms (e.g. tablets) comprise 50 mg or 100 mg vildagliptin.

Alogliptin may be administered to a patient at a daily dose of between 5 mg/day and 250 mg/day, optionally between 10 mg and 200 mg, optionally between 10 mg and 150 mg, and optionally between 10 mg and 100 mg of alogliptin (in each instance based on the molecular weight of the free base form of alogliptin). Thus, specific dosage amounts that may be used include, but are not limited to 10 mg, 12.5 mg, 20 mg, 25 mg, 50 mg, 75 mg and 100 mg of alogliptin per day. Alogliptin may be administered in its free base form or as a pharmaceutically acceptable salt.

Saxagliptin may be administered to a patient at a daily dose of between 2.5 mg/day and 100 mg/day, optionally between 2.5 mg and 50 mg. Specific dosage amounts that may be used include, but are not limited to 2.5 mg, 5 mg, 10 mg, 15 mg, 20 mg, 30 mg, 40 mg, 50 mg and 100 mg of saxagliptin per day.

The amount of the glucopyranosyl-substituted benzene derivative and of the DPP IV inhibitor in the pharmaceutical composition according to this invention correspond to the respective dosage ranges as provided hereinbefore. For example, a pharmaceutical composition comprises an amount of 5 to 50 mg of the compound (6), (7), (8), (9) or (11), in particular of the compound (9), and of the compound (A) (1-[(4-methyl-quinazolin-2-yl)methyl]-3-methyl-7-(2-butyn-1-yl)-8-(3-(R)-amino-piperidin-1-yl)-xanthine) in an amount of 0.5 mg to 10 mg.

Another example of a pharmaceutical composition comprises an amount of 5 to 50 mg of the compound (6), (7), (8), (9) or (11), in particular of the compound (9), and of sitagliptin in an amount of 1 to 100 mg active moiety.

A further example of a pharmaceutical composition comprises an amount of 5 to 50 mg of the compound (6), (7), (8), (9) or (11), in particular of the compound (9), and of vildagliptin in an amount of 1 to 100 mg active moiety.

A further example of a pharmaceutical composition comprises an amount of 5 to 50 mg of the compound (6), (7), (8), (9) or (11), in particular of the compound (9), and of alogliptin in an amount of 1 to 100 mg active moiety.

A further example of a pharmaceutical composition comprises an amount of 5 to 50 mg of the compound (6), (7), (8), (9) or (11), in particular of the compound (9), and of saxagliptin in an amount of 1 to 100 mg active moiety.

In the methods and uses according to the present invention the glucopyranosyl-substituted benzene derivative and the DPP IV inhibitor are administered in combination or alternation. The term "administration in combination" means that both active ingredients are administered at the same time, i.e. simultaneously, or essentially at the same time. The term "administration in alternation" means that at first a first active ingredient is administered and after a period of time the second active ingredient is administered, i.e. both active ingredients are administered sequentially. The period of time may be in the range from 30 min to 12 hours. The administration which is in combination or in alternation may be once, twice, three times or four times daily.

With regard to the administration of the glucopyranosyl-substituted benzene derivative in combination with the DPP IV inhibitor both active ingredients may be present in a single dosage form, for example in a tablet or capsule, or each active ingredient may be present in a separate dosage form, for example in two different or identical dosage forms.

With regard to their administration in alternation, each of the active ingredients is present in a separate dosage form, for example in two different or identical dosage forms.

Therefore, the pharmaceutical composition according to this invention may be present as single dosage forms which comprise both the glucopyranosyl-substituted benzene derivative and the DPP IV inhibitor as well as separate dosage forms wherein one dosage form comprises the glucopyranosyl-substituted benzene derivative and the other dosage form comprises the DPP IV inhibitor.

The case may arise in which one active ingredient has to be administered more often, for example twice per day, than the other active ingredient, which for example needs administration once daily. Therefore the term "administration in combination or alternation" also includes an administration scheme in which first both active ingredients are administered in combination or alternation and after a period of time only one active ingredient is administered again or vice versa.

Therefore, the present invention also includes pharmaceutical compositions which are present a separate dosage forms wherein one dosage form comprises the glucopyranosyl-substituted benzene derivative and the DPP IV inhibitor and the other dosage form comprises either the glucopyranosyl-substituted benzene derivative or the DPP IV inhibitor.

A pharmaceutical composition which is present as a separate or multiple dosage form, preferably as a kit of parts, is useful in combination therapy to flexibly suit the individual therapeutic needs of the patient.

A preferred kit of parts comprises
(a) a first containment containing a dosage form comprising the glucopyranosyl-substituted benzene derivative and at least one pharmaceutically acceptable carrier, and
(b) a second containment containing a dosage form comprising the DPP IV inhibitor and at least one pharmaceutically acceptable carrier.

A further aspect of the present invention is a manufacture comprising the pharmaceutical composition being present as separate dosage forms according to the present invention and a label or package insert comprising instructions that the separate dosage forms are to be administered in combination or alternation.

A yet further aspect of the present invention is a manufacture comprising a medicament which comprises a glucopyranosyl-substituted benzene derivative according to the present invention and a label or package insert which comprises instructions that the medicament may or is to be administered in combination or alternation with a medicament comprising a DPP IV inhibitor according to the present invention.

Another further aspect of the present invention is a manufacture comprising a medicament which comprises a DPP IV inhibitor according to the present invention and a label or package insert which comprises instructions that the medicament may or is to be administered in combination or alternation with a medicament comprising a glucopyranosyl-substituted benzene derivative according to the present invention.

The desired dose of the pharmaceutical composition according to this invention may conveniently be presented in a once daily or as divided dose administered at appropriate intervals, for example as two, three or more doses per day.

The pharmaceutical composition may be formulated for oral, rectal, nasal, topical (including buccal and sublingual), transdermal, vaginal or parenteral (including intramuscular, sub-cutaneous and intravenous) administration in liquid or solid form or in a form suitable for administration by inhalation or insufflation. Oral administration is preferred. The formulations may, where appropriate, be conveniently presented in discrete dosage units and may be prepared by any of the methods well known in the art of pharmacy. All methods include the step of bringing into association the active ingredient with one or more pharmaceutically acceptable carriers, like liquid carriers or finely divided solid carriers or both, and then, if necessary, shaping the product into the desired formulation.

The pharmaceutical composition may be formulated in the form of tablets, granules, fine granules, powders, capsules, caplets, soft capsules, pills, oral solutions, syrups, dry syrups, chewable tablets, troches, effervescent tablets, drops, suspension, fast dissolving tablets, oral fast-dispersing tablets, etc.

The pharmaceutical composition and the dosage forms preferably comprises one or more pharmaceutical acceptable carriers which must be "acceptable" in the sense of being compatible with the other ingredients of the formulation and not deleterious to the recipient thereof.

Pharmaceutical compositions suitable for oral administration may conveniently be presented as discrete units such as capsules, including soft gelatin capsules, cachets or tablets each containing a predetermined amount of the active ingredient; as a powder or granules; as a solution, a suspension or as an emulsion, for example as syrups, elixirs or self-emulsifying delivery systems (SEDDS). The active ingredients may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The pharmaceutical composition according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilisation from solution, for constitution with a suitable vehicle, e.g. sterile, pyrogen-free water, before use.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the active compound(s) with the softened or melted carrier(s) followed by chilling and shaping in moulds.

The pharmaceutical compositions and methods according to this invention show advantageous effects in the treatment and prevention of those diseases and conditions as described hereinbefore compared with pharmaceutical compositions and methods which comprise only one of both active ingredients. Advantageous effects may be seen for example with respect to efficacy, dosage strength, dosage frequency, pharmacodynamic properties, pharmacokinetic properties, fewer adverse effects, etc.

Examples of pharmaceutically acceptable carriers are known to the one skilled in the art.

Methods for the manufacture of glucopyranosyl-substituted benzene derivatives according to this invention and of prodrugs thereof are known to the one skilled in the art. Advantageously, the compounds according to this invention can be prepared using synthetic methods as described in the literature, in particular as described in the WO 01/27128, WO 03/099836, WO 2005/092877, WO 2006/034489, WO 2006/064033, WO 2007/025943 and WO 2007/031548. The compounds (1) to (6) may preferably be prepared following the synthetic methods described in WO 2007/093610 and WO 2008/055870. Advantageously, the compound (7) is prepared as described in the WO 2005/092877 (see example 12).

Advantageous methods of synthesis of the compounds (8) and (9) are described in the WO 2005/092877 (see examples 2 and 3), WO 2006/117360, WO 2006/117359 and WO 2006/120208. The compounds (10) and (11) are preferably obtained via the synthetic methods described in the WO 2006/064033.

With respect to embodiment A, the methods of synthesis for the DPP IV inhibitors according to embodiment A of this invention are known to the skilled person. Advantageously, the DPP IV inhibitors according to embodiment A of this invention can be prepared using synthetic methods as described in the literature. Thus, for example, purine derivatives of formula (I) can be obtained as described in WO 2002/068420, WO 2004/018468, WO 2005/085246, WO 2006/029769 or WO 2006/048427, the disclosures of which are incorporated herein. Purine derivatives of formula (II) can be obtained as described, for example, in WO 2004/050658 or WO 2005/110999, the disclosures of which are incorporated herein. Purine derivatives of formula (III) and (IV) can be obtained as described, for example, in WO 2006/068163, WO 2007/071738 or WO 2008/017670, the disclosures of which are incorporated herein. The preparation of those DPP IV inhibitors, which are specifically mentioned hereinabove, is disclosed in the publications mentioned in connection therewith. Polymorphous crystal modifications and formulations of particular DPP IV inhibitors are disclosed in WO 2007/054201 and WO 2007/128724, respectively, the disclosures of which are incorporated herein in their entireties.

With respect to embodiment B, the methods of synthesis for the DPP IV inhibitors of embodiment B are described in the scientific literature and/or in published patent documents, particularly in those cited above in paragraph "background of the invention".

The DPP IV inhibitor may be present in the form of a pharmaceutically acceptable salt. Pharmaceutically acceptable salts include, without being restricted thereto, such as salts of inorganic acid like hydrochloric acid, sulfuric acid and phosphoric acid; salts of organic carboxylic acid like oxalic acid, acetic acid, citric acid, malic acid, benzoic acid, maleic acid, fumaric acid, tartaric acid, succinic acid and glutamic acid and salts of organic sulfonic acid like methanesulfonic acid and p-toluenesulfonic acid. The salts can be formed by combining the compound and an acid in the appropriate amount and ratio in a solvent and decomposer. They can be also obtained by the cation or anion exchange from the form of other salts. The DPP IV inhibitor may be present in the form of a pharmaceutically acceptable salt. Pharmaceutically acceptable salts include such as salts of inorganic acid like hydrochloric acid, sulfuric acid and phosphoric acid; salts of organic carboxylic acid like oxalic acid, acetic acid, citric acid, malic acid, benzoic acid, maleic acid, fumaric acid, tartaric acid, succinic acid and glutamic acid and salts of organic sulfonic acid like methanesulfonic acid and p-toluenesulfonic acid. The salts can be formed by combining the compound and an acid in the appropriate amount and ratio in a solvent and decomposer. They can be also obtained by the cation or anion exchange from the form of other salts.

The glucopyranosyl-substituted benzene derivative and/or the DPP IV inhibitor or a pharmaceutically acceptable salt thereof may be present in the form of a solvate such as a hydrate or alcohol adduct.

Any of the above mentioned combinations and methods within the scope of the invention may be tested by animal models known in the art. In the following, in vivo experiments are described which are suitable to evaluate pharmacologically relevant properties of pharmaceutical compositions and methods according to this invention:

Pharmaceutical compositions and methods according to this invention can be tested in genetically hyperinsulinemic or diabetic animals like db/db mice, ob/ob mice, Zucker Fatty (fa/fa) rats or Zucker Diabetic Fatty (ZDF) rats. In addition, they can be tested in animals with experimentally induced diabetes like HanWistar or Sprague Dawley rats pretreated with streptozotocin.

The effect on glycemic control of the combinations according to this invention can be tested after single dosing of a glucopyranosyl-substituted benzene derivative and a DPP IV inhibitor alone and in combination in an oral glucose tolerance test in the animal models described hereinbefore. The time course of blood glucose is followed after on oral glucose challenge in overnight fasted animals. The combinations according to the present invention significantly improve glucose excursion compared to each monotherapy as measured by reduction of peak glucose concentrations or reduction of glucose AUC. In addition, after multiple dosing of a glucopyranosyl-substituted benzene derivative and a DPP IV inhibitor alone and in combination in the animal models described hereinbefore, the effect on glycemic control can be determined by measuring the HbA1c value in blood. The combinations according to this invention significantly reduce HbA1c compared to each monotherapy.

The possible dose reduction of either the glucopyranosyl-substituted benzene derivative or the DPP-IV inhibitor or of both active ingredients can be tested by the effect on glycemic control of lower doses of the combinations and monotherapies in the animal models described hereinbefore. The combinations according to this invention at the lower doses significantly improve glycemic control compared to placebo treatment whereas the monotherapies at lower doses do not.

The improved independence from insulin of the treatment according to this invention can be shown after single dosing in oral glucose tolerance tests in the animal models described hereinbefore. The time course of plasma insulin is followed after a glucose challenge in overnight fasted animals. The glucopyranosyl-substituted benzene derivative in combination with the DPP IV inhibitor will exhibit lower insulin peak concentrations or insulin AUC at lower blood glucose excursion than the DPP IV inhibitor alone.

The increase in active GLP-1 levels by treatment according to this invention after single or multiple dosing can be determined by measuring those levels in the plasma of animal models described hereinbefore in either the fasting or postprandial state. Likewise, a reduction in glucagon levels in plasma can be measured under the same conditions. The glucopyranosyl-substituted benzene derivative in combination with the DPP IV inhibitor will exhibit higher active GLP-1 concentrations and lower glucagon concentrations than the glucopyranosyl-substituted benzene derivative alone.

A superior effect of the combination of a glucopyranosyl-substituted benzene derivative and a DPP IV inhibitor according to the present invention than of the glucopyranosyl-substituted benzene derivative alone on beta-cell regeneration and neogenesis can be determined after multiple dosing in the animal models described hereinbefore by measuring the increase in pancreatic insulin content, or by measuring increased beta-cell mass by morphometric analysis after immunohistochemical staining of pancreatic sections, or by measuring increased glucose-stimulated insulin secretion in isolated pancreatic islets.

In the foregoing and following text, H atoms of hydroxyl groups are not explicitly shown in every case in structural formulae. The Examples that follow are intended to illustrate the present invention without restricting it. The terms "room temperature" and "ambient temperature" are used interchangeably and denote temperatures of about 20° C. The following abbreviations are used:
tBu tert.butyl
dba dibenzylidenaceton
DMF dimethylformamide
DMSO dimethyl sulfoxide
NMP N-methyl-2-pyrrolidone
THF tetrahydrofuran Preparation of the Starting Compounds:

Example I

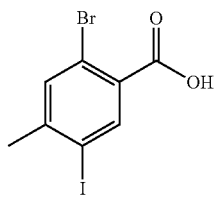

2-Bromo-5-iodo-4-methyl-benzoic acid

N-Iodosuccinimide (19.1 g) is added in portions to an ice-cold solution of 2-bromo-4-methyl-benzoic acid (18.4 g) dissolved in sulphuric acid (20 mL). The resulting mixture is stirred at 5-10° C. for 3 h before warming to room temperature overnight. Then, the mixture is poured on crushed ice and the resultant solution is extracted with ethyl acetate. The combined extracts are washed in succession with aqueous 10% $Na_2S_2O_3$ solution (2×), water (3×), and brine (1×). After drying ($MgSO_4$), the organic solvent is evaporated under reduced. The remaining solid is taken up in water and the resulting slurry is stirred at 70° C. for 5 min. The non-dissolving part is separated by filtration and dried to give the desired product.

Yield: 27.2 g (96% of theory)
Mass spectrum (ESI⁻): m/z=339/341 (Br) [M−H]⁻
The following compound may be obtained analogously to Example I:

(1) (2-Bromo-5-iodo-4-methoxy-phenyl)-(4-ethyl-phenyl)-methanone

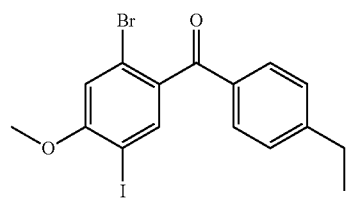 [SMILES: CCc1ccc(C(=O)c2cc(I)c(OC)cc2Br)cc1]

Mass spectrum (ESI⁺): m/z=445/447 (Br) [M+H]⁺
The starting material, (2-bromo-4-methoxy-phenyl)-(4-ethyl-phenyl)-methanone, is prepared as described under Examples II and III.

Example II

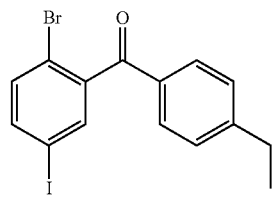 [SMILES: CCc1ccc(C(=O)c2cc(I)ccc2Br)cc1]

(2-Bromo-5-iodo-phenyl)-(4-ethyl-phenyl)-methanone

Oxalyl chloride (9.5 mL) is added to a solution of 2-bromo-5-iodo-benzoic acid (25.0 g) in dichloromethane (50 mL). A few drops of DMF are added and the mixture is stirred at room temperature overnight. Then, the reaction solution is concentrated under reduced pressure and the residue is taken up in dichloromethane (50 mL) and ethylbenzene (23 mL). The resulting solution is cooled in an ice-bath and aluminum trichloride (12.5 g) is added in portions. Then, the cooling bath is removed and the reaction mixture is stirred at room temperature for 4 h. After consumption of the intermediate substituted benzoyl chloride, the reaction mixture is poured onto crushed ice and the organic phase is separated off. The aqueous phase is extracted with ethyl acetate and the combined organic phases are washed in succession with 1 M hydrochloric acid, 1 M potassium hydroxide solution and brine. The organic phase is dried (sodium sulphate) and the solvent is removed under reduced pressure to give the product as an oil that crystallizes on standing.

Yield: 30.8 g (97% of theory)

Mass spectrum (ESI$^+$): m/z=415/417 (Br) [M+H]$^+$

The following compounds may be obtained analogously to Example II:

(1) (2-Bromo-5-iodo-4-methyl-phenyl)-(4-ethyl-phenyl)-methanone

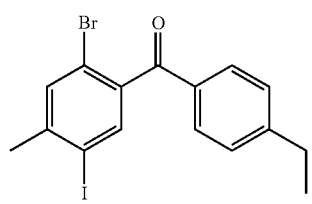 [SMILES: CCc1ccc(C(=O)c2cc(I)c(C)cc2Br)cc1]

Mass spectrum (ESI$^+$): m/z=429/431 (Br) [M+H]$^+$

(2) (2-Bromo-4-fluoro-phenyl)-(4-ethyl-phenyl)-methanone

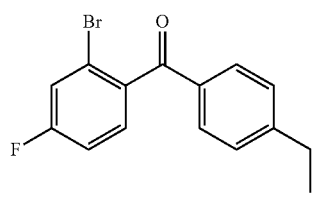 [SMILES: CCc1ccc(C(=O)c2ccc(F)cc2Br)cc1]

Mass spectrum (ESI$^+$): m/z=307/309 (Br) [M+H]$^+$

Example III

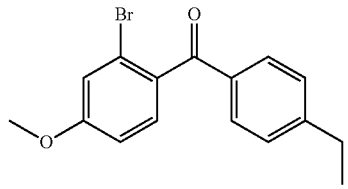 [SMILES: CCc1ccc(C(=O)c2ccc(OC)cc2Br)cc1]

(2-Bromo-4-methoxy-phenyl)-(4-ethyl-phenyl)-methanone

Sodium methoxide (10.5 g) is added portionwise to (2-bromo-4-fluoro-phenyl)-(4-ethyl-phenyl)-methanone (43.0 g) dissolved in DMF (200 mL). The solution is stirred overnight, before another portion of sodium methoxide (5.5 g) is added. After another 3 h of stirring, water is added and the resulting mixture is extracted with ethyl acetate. The organic phase is dried (sodium sulphate), the solvent is removed and the residue is chromatographed on silica gel (cyclohexane/ethyl acetate 20:1->9:1).

Yield: 33.7 g (75% of theory)

Mass spectrum (ESI$^+$): m/z=319/321 (Br) [M+H]$^+$

Example IV

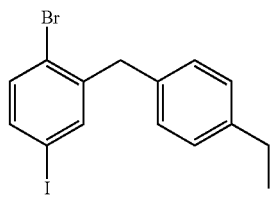 [SMILES: CCc1ccc(Cc2cc(I)ccc2Br)cc1]

4-Bromo-3-(4-ethyl-benzyl)-1-iodo-benzene

A solution of (2-bromo-5-iodo-phenyl)-(4-ethyl-phenyl)-methanone (32 g) and triethylsilane (50 mL) in dichloromethane (30 mL) and acetonitrile (100 mL) is cooled in an ice-bath. Then, boron trifluoride diethyletherate (20 mL) is added dropwise over 5 min. The cooling bath is removed and the solution is heated to 45-50° C. and stirred at this temperature for 4 h. After cooling to ambient temperature, 4 M aqueous KOH solution is added and the resulting mixture is extracted with ethyl acetate. The combined organic phases are washed with 2 M potassium hydroxide solution and brine and then dried (sodium sulphate). After the solvent is evaporated, the residue is chromatographed on silica gel (cyclohexane/ethyl acetate 1:0->9:1).

Yield: 21 g (68% of theory)

Mass spectrum (ESI$^+$): m/z=418/420 (Br) [M+NH$_4$]$^+$

The following compounds may be obtained analogously to Example IV:

(1) 4-Bromo-5-(4-ethyl-benzyl)-1-iodo-2-methyl-benzene

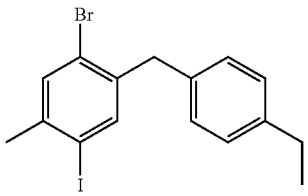 [SMILES: CCc1ccc(Cc2cc(I)c(C)cc2Br)cc1]

Mass spectrum (ESI$^+$): m/z=432/434 (Br) [M+NH$_4$]$^+$ (2) 4-Bromo-5-(4-ethyl-benzyl)-1-iodo-2-methoxy-benzene

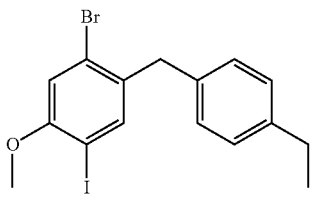 [SMILES: CCc1ccc(Cc2cc(I)c(OC)cc2Br)cc1]

Mass spectrum (ESI$^+$): m/z=448/450 (Br) [M+NH$_4$]$^+$

Example V

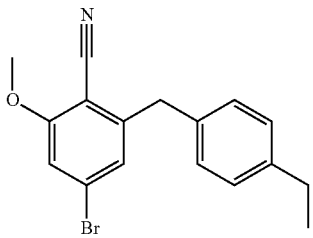 [SMILES: CCc1ccc(Cc2cc(Br)cc(OC)c2C#N)cc1]

1-Bromo-4-cyano-3-methoxy-5-(4-ethyl-benzyl)-benzene

KOtBu (11.8 g) is added to a flask charged with a stir bar and dry NMP (40 mL) and chilled to −10° C. under argon atmosphere. A solution of ethyl (4-ethyl-phenyl)-acetate (10.1 g) and 1-bromo-4-cyano-3,5-difluoro-benzene (11.5 g) in NMP (40 mL) is added at such a rate that the reaction temperature maintains below 10° C. After stirring for 1 hour at room temperature, methanol (50 mL) and 1 M aqueous sodium hydroxide solution (39 mL) are added and the resulting mixture is stirred overnight at 100° C. Then, 4 M aqueous hydrochloric acid (100 mL) is added and the mixture is stirred for another h at 100° C. The methanol fraction is evaporated, water (200 mL) is added to the residue and the resulting mixture is extracted with ethyl acetate. The combined organic extracts are washed twice with water, twice with brine and dried (MgSO$_4$). The solvent is evaporated and the residue is washed with methanol. The insoluble residue is separated by filtration and dried to give the white product.

Yield: 10.0 g (58% of theory)
Mass spectrum (ESI$^+$): m/z=330/332 (Br) [M+H]$^+$ Example VI

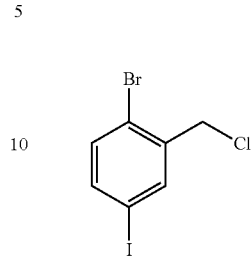

4-Bromo-3-chloromethyl-1-iodo-benzene

Thionyl chloride (13 mL) is added to a suspension of 4-bromo-3-hydroxymethyl-1-iodo-benzene (47.0 g) in dichloromethane (100 mL) containing DMF (0.1 mL). The mixture is stirred at ambient temperature for 3 h. Then, the solvent and the excess reagent is removed under reduced pressure. The residue is triturated with methanol and dried.
Yield: 41.0 g (82% of theory)

Example VII

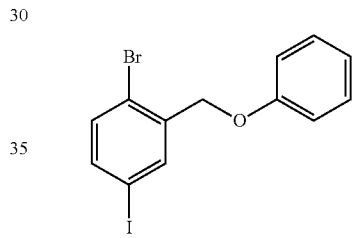

4-Bromo-1-iodo-3-phenoxymethyl-benzene

Phenol (13 g) dissolved in aqueous 4 M KOH solution (60 mL) is added to 4-bromo-3-chloromethyl-1-iodo-benzene (41.0 g) dissolved in acetone (50 mL). NaI (0.5 g) is added and the resulting mixture is stirred at 50° C. overnight. Then, water is added and the resulting mixture is extracted with ethyl acetate. The combined extracts are dried (Na$_2$SO$_4$) and the solvent is evaporated under reduced pressure. The residue is purified by chromatography on silica gel (cyclohexane/ethyl acetate 19:1).
Yield: 38.0 g (79% of theory)

Example VIII

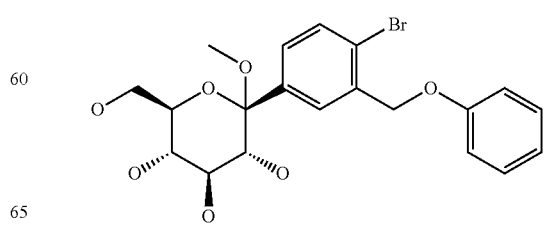

1-Bromo-4-(1-methoxy-D-glucopyranos-1-yl)-2-(phenoxymethyl)-benzene

A 2 M solution of iPrMgCl in THF (11 mL) is added to dry LiCl (0.47 g) suspended in THF (11 mL). The mixture is stirred at room temperature until all the LiCl is dissolved. This solution is added dropwise to a solution of 4-bromo-1-iodo-3-phenoxymethyl-benzene (8.0 g) in tetrahydrofuran (40 mL) cooled to −60° C. in argon atmosphere. The resulting solution is warmed to −40° C. and then 2,3,4,6-tetrakis-O-(trimethylsilyl)-D-glucopyranone (10.7 g, 90% pure) in tetrahydrofuran (5 mL) is added. The resulting solution is warmed to −5° C. in the cooling bath and stirred for another 30 min at this temperature. Aqueous NH$_4$Cl solution is added and the resultant mixture is extracted with ethyl acetate. The combined organic extracts are dried over sodium sulphate and the solvent is removed under reduced pressure. The residue is dissolved in methanol (80 mL) and treated with methanesulfonic acid (0.6 mL). After stirring the reaction solution at 35-40° C. overnight, the solution is neutralized with solid NaHCO$_3$ and the methanol is removed under reduced pressure. The remainder is diluted with aqueous NaHCO$_3$ solution and the resulting mixture is extracted with ethyl acetate. The combined extracts are dried over sodium sulphate and the solvent is evaporated to yield the crude product that is submitted to reduction without further purification.

Yield: 7.8 g (93% of theory)

The following compounds may be obtained analogously to Example VIII:

(1) 1-Bromo-2-(4-ethylbenzyl)-4-(1-methoxy-D-glucopyranos-1-yl)-benzene

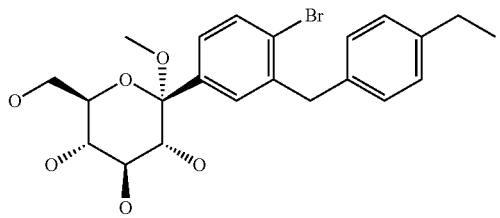 [SMILES: CCc1ccc(Cc2cc([C@]3(OC)O[C@H](CO)[C@@H](O)[C@H](O)[C@H]3O)ccc2Br)cc1]

Mass spectrum (ESI$^-$): m/z=511/513 (Br) [M+HCOO]$^-$

(2) 1-Bromo-2-(4-ethylbenzyl)-4-(1-methoxy-D-glucopyranos-1-yl)-5-methyl-benzene

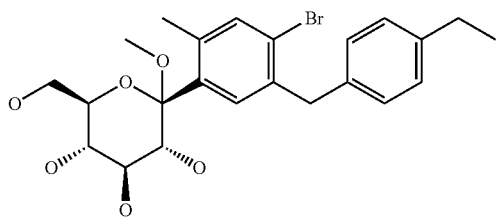 [SMILES: CCc1ccc(Cc2cc([C@]3(OC)O[C@H](CO)[C@@H](O)[C@H](O)[C@H]3O)c(C)cc2Br)cc1]

Alternatively, the reaction may be conducted with 2,3,4,6-tetra-O-benzyl-D-glucopyranone instead of 2,3,4,6-tetrakis-O-(trimethylsilyl)-D-glucopyranone to obtain the analogous tetra-O-benzyl protected addition product of this compound. The benzyl groups may be taken off after the reduction of the anomeric center by using BCl$_3$ in dichloromethane.

(3) 1-Bromo-2-(4-ethylbenzyl)-4-(1-methoxy-D-glucopyranos-1-yl)-5-methoxy-benzene

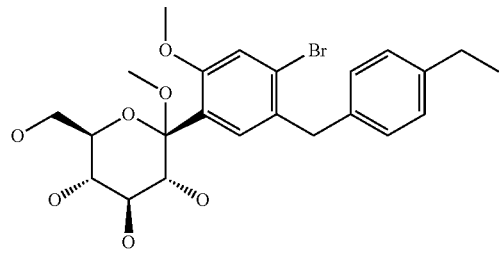 [SMILES: CCc1ccc(Cc2cc([C@]3(OC)O[C@H](CO)[C@@H](O)[C@H](O)[C@H]3O)c(OC)cc2Br)cc1]

Example IX

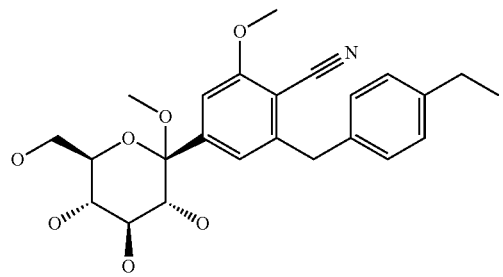 [SMILES: CCc1ccc(Cc2cc([C@]3(OC)O[C@H](CO)[C@@H](O)[C@H](O)[C@H]3O)cc(OC)c2C#N)cc1]

6-(4-Ethylbenzyl)-2-methoxy-4-(1-methoxy-D-glucopyranos-1-yl)-benzonitrile

A 1.7 M solution of tBuLi in pentane (18.3 mL) cooled to −78° C. is added dropwise to a solution of 1-bromo-4-cyano-5-(4-ethyl-benzyl)-3-methoxy-benzene (5.0 g) in hexane (40 mL) and THF (20 mL) chilled to −78° C. nBuLi or sBuLi instead of tBuLi may be used as well. After complete addition and additional 15 min of stirring, a solution of 2,3,4,6-tetrakis-O-(trimethylsilyl)-D-glucopyranone (90%, 7.9 g) in hexane (30 mL) cooled to −78° C. is added via a transfer needle. The resulting solution is stirred at −70° C. for 2 h and then slowly warmed to −5° C. The reaction is quenched with 1% acetic acid in water (100 mL) and the resulting mixture is extracted with ethyl acetate. The combined organic extracts are washed with brine and dried (sodium sulphate). After removal of the solvent, the residue is dissolved in methanol (50 mL) and treated with methanesulfonic acid (2.5 mL) to produce the desired more stable anomeric linkage. The solution is stirred at 50° C. overnight and then neutralized by the addition of solid NaHCO$_3$. The solvent is removed under reduced pressure and the residue is taken up in ethyl acetate. The organic solution is washed with water and brine and dried (sodium sulphate). After the removal of the solvent, the crude product is purified by chromatography on silica gel (dichloromethane/methanol 1:0->2:1).

Yield: 0.5 g (7% of theory)

Alternatively, the reaction may be conducted with 2,3,4,6-tetra-O-benzyl-D-glucopyranone instead of 2,3,4,6-tetrakis-O-(trimethylsilyl)-D-glucopyranone to obtain the analogous tetra-O-benzyl protected addition product of this compound. The benzyl groups may be taken off after the reduction of the anomeric center by using BCl$_3$ in dichloromethane.

Example X

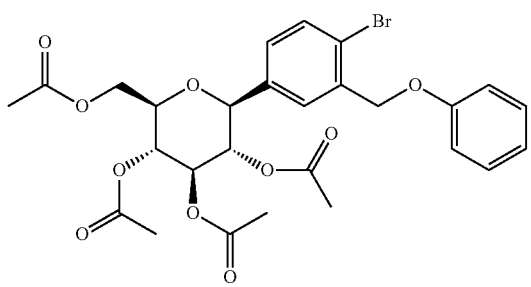 [SMILES: CC(=O)OC[C@H]1O[C@@H](c2ccc(Br)c(COc3ccccc3)c2)[C@H](OC(C)=O)[C@@H](OC(C)=O)[C@@H]1OC(C)=O]

1-Bromo-4-(2,3,4,6-tetra-O-acetyl-(3-D-glucopyranos-1-yl)-2-(phenoxymethyl)-benzene Boron trifluoride etherate (4.9 mL) is added to a solution of 1-bromo-4-(1-methoxy-D-glucopyranos-1-yl)-2-(phenoxymethyl)-benzene (8.7 g) and triethylsilane (9.1 mL) in dichloromethane (35 mL) and acetonitrile (50 mL) cooled to −20° C. at such a rate that the temperature maintains below −10° C. The resultant solution is warmed to 0° C. over a period of 1.5 h and then treated with aqueous sodium hydrogen carbonate solution. The resulting mixture is stirred for 0.5 h, the organic solvent is removed and the residue is extracted with ethyl acetate. The combined organic layers are dried over sodium sulphate and the solvent is removed. The residue is taken up in dichloromethane (50 mL) and pyridine (9.4 mL), acetic anhydride (9.3 mL) and 4-dimethylaminopyridine (0.5 g) are added in succession to the solution. The solution is stirred for 1.5 h at ambient temperature and then diluted with dichloromethane. This solution is washed twice with 1 M hydrochloric acid and dried over sodium sulfate. After the solvent is removed, the residue is recrystallized from ethanol to furnish the product as a colorless solid.

Yield: 6.78 g (60% of theory)

Mass spectrum (ESI$^+$): m/z=610/612 (Br) [M+NH$_4$]$^+$

The following compounds may be obtained analogously to Example X:

(1) 1-Bromo-2-(4-ethylbenzyl)-4-(2,3,4,6-tetra-O-acetyl-β-D-glucopyranos-1-yl)-benzene

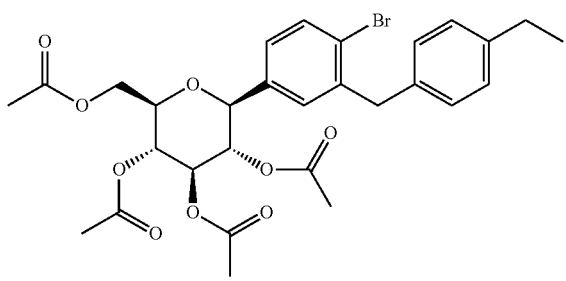 [SMILES: CCc1ccc(Cc2cc([C@@H]3O[C@H](COC(C)=O)[C@@H](OC(C)=O)[C@H](OC(C)=O)[C@H]3OC(C)=O)ccc2Br)cc1]

Mass spectrum (ESI$^+$): m/z=622/624 [M+NH$_4$]$^+$ (2) 1-Bromo-2-(4-ethylbenzyl)-4-(2,3,4,6-tetra-O-acetyl-β-D-glucopyranos-1-yl)-5-methoxy-benzene

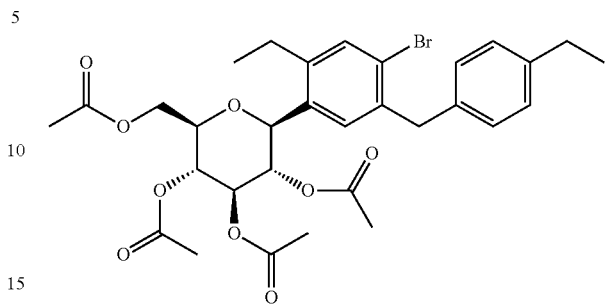

Mass spectrum (ESI$^+$): m/z=652/654 (Br) [M+NH$_4$]$^+$ (3) 6-(4-Ethylbenzyl)-4-(2,3,4,6-tetra-O-acetyl-β-D-glucopyranos-1-yl)-2-methoxy-benzonitrile

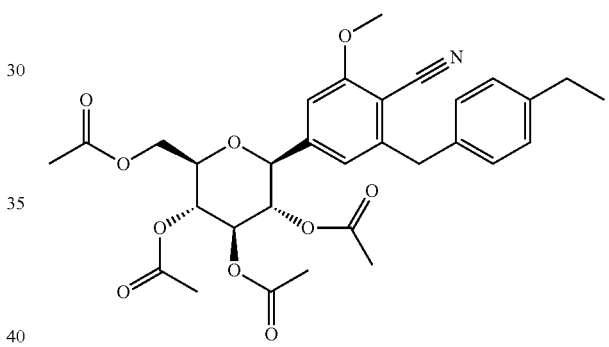

Mass spectrum (ESI$^+$): m/z=599 [M+NH$_4$]$^+$

The reduction is conducted on 6-(4-ethylbenzyl)-4-(1-methoxy-D-glucopyranos-1-yl)-2-methoxy-benzonitrile in analogy to the procedure described above.

(4) 1-Bromo-2-(4-ethylbenzyl)-4-(β-D-glucopyranos-1-yl)-5-methyl-benzene

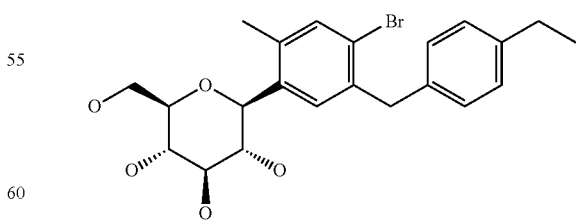

Mass spectrum (ESI$^+$): m/z=468/470 (Br) [M+NH$_4$]$^+$

This compound is isolated with the free hydroxyl groups after the reduction according to the procedure described above is finished.

Example XI

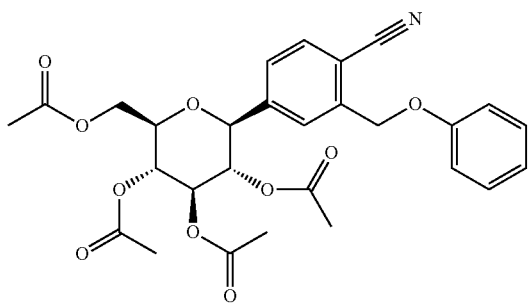 [SMILES: CC(=O)OC[C@H]1O[C@@H](c2ccc(C#N)c(COc3ccccc3)c2)[C@H](OC(C)=O)[C@@H](OC(C)=O)[C@@H]1OC(C)=O]

2-(Phenoxymethyl)-4-(2,3,4,6-tetra-O-acetyl-(β-D-glucopyranos-1-yl)-benzonitrile A flask charged with a stir bar, 1-bromo-4-(2,3,4,6-tetra-O-acetyl-β-D-glucopyranos-1-yl)-2-(phenoxymethyl)-benzene (5.4 g), zinc cyanide (1.0 g), zinc (30 mg), Pd$_2$(dibenzylideneacetone)$_3$*CHCl$_3$ (141 mg) and tri-tert-butylphosphonium tetrafluoroborate (111 mg) is flushed with argon. Then degassed NMP (12 mL) containing 0.1% water is added (alternatively, the glucoside dissolved in NMP is added) and the resulting mixture is stirred at room temperature for 18 h. After dilution with ethyl acetate, the mixture is filtered and the filtrate is washed with aqueous sodium hydrogen carbonate solution. The organic phase is dried (sodium sulphate) and the solvent is removed. The residue is recrystallized from ethanol.

Yield: 4.10 g (84% of theory)

Mass spectrum (ESI$^+$): m/z=557 [M+NH$_4$]$^+$

Alternatively, the compound may also be obtained employing the procedures described under Examples XII and 3

Example XII

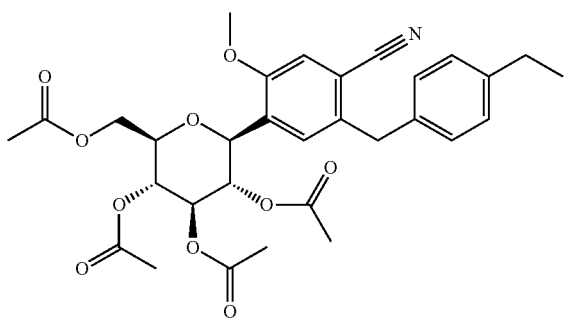 [SMILES: CCc1ccc(Cc2cc([C@@H]3O[C@H](COC(C)=O)[C@@H](OC(C)=O)[C@H](OC(C)=O)[C@H]3OC(C)=O)c(OC)cc2C#N)cc1]

2-(4-Ethylbenzyl-1)-5-methoxy-4-(2,3,4,6-tetra-O-acetyl-β-D-glucopyranos-1-yl)-benzonitrile A flask charged with a stir bar, 1-bromo-2-(4-ethylbenzyl)-5-methoxy-4-(2,3,4,6-tetra-O-acetyl-β-D-glucopyranos-1-yl)benzene (1.6 g), copper(I) cyanide (0.56 g) and NMP (10 mL) is stirred at 215° C. for 3 h. Then, water is added and the precipitate is separated by filtration. The precipitate is dissolved in ethyl acetate (50 mL) and filtered over Celite. The filtrate is dried (Na$_2$SO$_4$) and concentrated. The residue is purified by chromatography on silica gel (cyclohexane/ethyl acetate 2:1->1:2).

Yield: 1.1 g (75% of theory)

Mass spectrum (ESI$^+$): m/z=583 [M+NH$_4$]$^+$

This compound can also be prepared using the procedures described for Examples XI and 3.

Example XIII

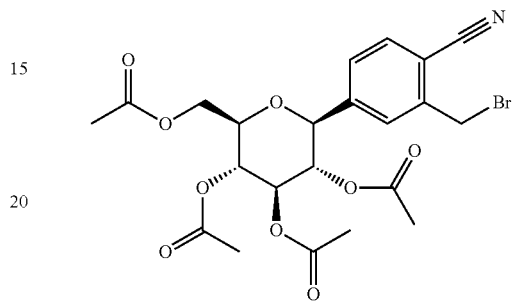

2-Bromomethyl-4-(2,3,4,6-tetra-O-acetyl-β-D-glucopyranos-1-yl)-benzonitrile

A 33% solution of hydrobromic acid in acetic acid (15 mL) is added to a solution of 2-phenyloxymethyl-4-(2,3,4,6-tetra-O-acetyl-β-D-glucopyranos-1-yl)-benzonitrile (0.71 g) and acetic anhydride (0.12 mL) in acetic acid (10 ml). The resulting solution is stirred at 55° C. for 6 h and then cooled in an ice-bath. The reaction mixture is neutralized with chilled aqueous potassium carbonate solution, and the resultant mixture is extracted with ethyl acetate. The combined organic extracts are dried over sodium sulfate and the solvent is removed under reduced pressure. The residue is taken up in ethyl acetate/cyclohexane (1:5), and the precipitate is separated by filtration and dried at 50° C. to give the product.

Yield: 0.52 g (75% of theory)

Mass spectrum (ESI$^+$): m/z=543/545 (Br) [M+NH$_4$]$^+$

Example XIV

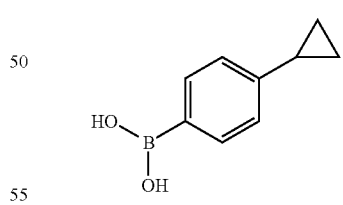

4-Cyclopropyl-phenylboronic acid 2.5 M nButyllithium in hexane (14.5 mL) is added dropwise to a solution of 1-bromo-4-cyclopropyl-benzene (5.92 g) in THF (14 mL) and toluene (50 mL) chilled to −70° C. The resultant solution is stirred at −70° C. for 30 min before triisopropyl borate (8.5 mL) is added. The solution is warmed to −20° C. and then treated with 4 M aqueous hydrochloric acid (15.5 mL). The reaction mixture is further warmed to room temperature and then the organic phase is separated.

The aqueous phase is extracted with ethyl acetate and the combined organic phases are dried (sodium sulphate). The solvent is evaporated and the residue is triturated with a mixture of ether and cyclohexane to give the product as a colorless solid.

Yield: 2.92 g (60% of theory)

Mass spectrum (ESI$^-$): m/z=207 (Cl) [M+HCOO]$^-$

Preparation of the End Compounds:

Example (1)

6-(4-Ethylbenzyl)-4-(β-D-glucopyranos-1-yl)-2-methoxy-benzonitrile

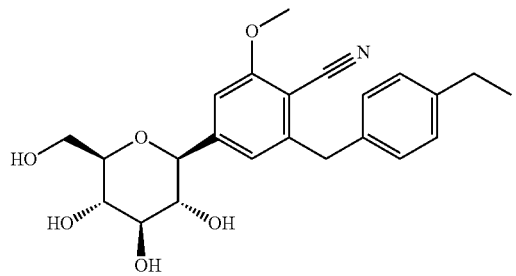 [SMILES: CCc1ccc(Cc2cc([C@@H]3O[C@H](CO)[C@@H](O)[C@H](O)[C@H]3O)cc(OC)c2C#N)cc1]

Aqueous sodium hydroxide solution (1.4 mL, 1 mol/L) is added to 6-(4-ethylbenzyl)-4-(2,3,4,6-tetra-O-acetyl-β-D-glucopyranos-1-yl)-2-methoxy-benzonitrile (0.16 g) dissolved in methanol (1 mL) and THF (1 mL). The solution is stirred at room temperature for 1 h and then neutralized with hydrochloric acid (1 mol/L). After removal of the organic solvents, the residue is diluted with aqueous sodium bicarbonate solution and the resulting mixture is extracted with ethyl acetate. The combined organic extracts are dried (sodium sulphate) and the solvent is evaporated. The remainder is purified by chromatography on silica gel (dichloromethane/methanol 1:0->8:1).

Yield: 65 mg (57% of theory)

Mass spectrum (ESI$^+$): m/z=431 [M+NH$_4$]$^+$

The following compound is obtained analogously to Example 1:

Example (2)

2-(4-Ethylbenzyl)-4-(β-D-glucopyranos-1-yl)-5-methoxy-benzonitrile

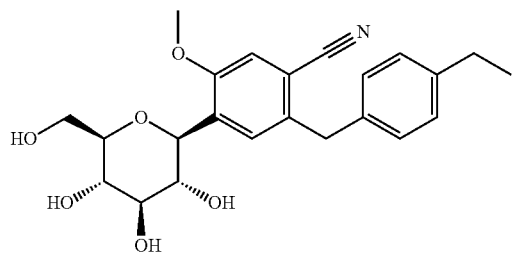 [SMILES: CCc1ccc(Cc2cc([C@@H]3O[C@H](CO)[C@@H](O)[C@H](O)[C@H]3O)c(OC)cc2C#N)cc1]

Mass spectrum (ESI$^+$): m/z=431 [M+NH$_4$]$^+$

Example (3)

1-Cyano-2-(4-ethylbenzyl)-4-(β-D-glucopyranos-1-yl)-5-methyl-benzene

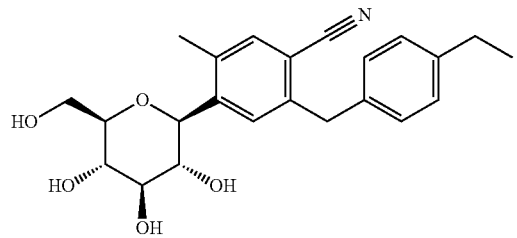 [SMILES: CCc1ccc(Cc2cc([C@@H]3O[C@H](CO)[C@@H](O)[C@H](O)[C@H]3O)c(C)cc2C#N)cc1]

A microwave oven-suited vessel charged with a stir bar, 1-bromo-2-(4-ethylbenzyl)-4-(6-D-glucopyranos-1-yl)-5-methyl-benzene (0.40 g), Ni(CN)$_2$ (0.10 g) and NMP (4 mL) and flushed with argon is heated in a microwave oven at 220° C. for 1 h. Then, water is added and the resulting mixture is extracted with ethyl acetate. The combined organic extracts are dried (sodium sulphate) and the solvent is evaporated. The remainder is purified by HPLC on reversed phase (YMC C18, acetonitrile/water).

Yield: 0.30 g (85% of theory)

Mass spectrum (ESI$^+$): m/z=415 [M+NH$_4$]$^+$

Example (4)

2-(4-Ethylbenzyl)-4-(β-D-glucopyranos-1-yl)-5-hydroxy-benzonitrile

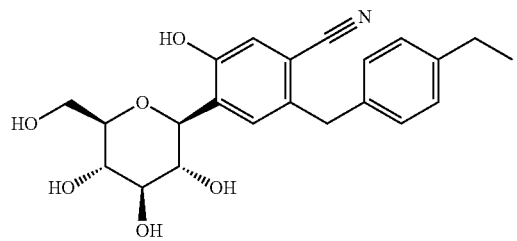 [SMILES: CCc1ccc(Cc2cc([C@@H]3O[C@H](CO)[C@@H](O)[C@H](O)[C@H]3O)c(O)cc2C#N)cc1]

A mixture of 2-(4-ethylbenzyl)-5-methoxy-4-(2,3,4,6-tetra-O-acetyl-β-D-glucopyranos-1-yl)-benzonitrile (0.80 g) and pyridinium hydrochloride (9.0 g) is heated at 215° C. for 1 h. After cooling to ambient temperature, water is added and the resulting solution is extracted with ethyl acetate. The combined organic extracts are dried (MgSO$_4$) and the solvent is removed under reduced pressure. The residue is dissolved in methanol (10 mL) and treated with 4 M aqueous NaOH solution (2.2 mL). The solution is stirred at room temperature for 1 h and then acidified using hydrochloric acid (4 mol/L). After removal of the organic solvents, the residue is extracted with ethyl acetate, the combined organic extracts are dried (sodium sulphate) and the solvent is evaporated. The remainder is purified by HPLC on reversed phase (YMC C18, acetonitrile/water).

Yield: 0.25 g (46% of theory)

Mass spectrum (ESI$^-$): m/z=398 [M−H]$^-$

Example (5)

2-(4-Ethyl-benzyl)-4-(β-D-glucopyranos-1-yl)-benzonitrile

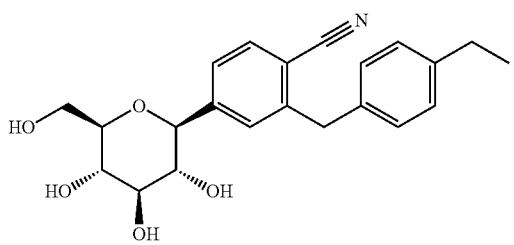 [SMILES: CCc1ccc(Cc2cc([C@@H]3O[C@H](CO)[C@@H](O)[C@H](O)[C@H]3O)ccc2C#N)cc1]

A flask is charged with a stir bar, zinc (10 mg), zinc cyanide (0.12 g), Pd$_2$(dba)$_3$*CHCl$_3$ (42 mg) and tri-tertbutylphosphonium tetrafluoroborate (26 mg) and put under Ar atmosphere. Then, 1-bromo-2-(4-ethylbenzyl)-4-(2,3,4,6-tetra-O-acetyl-β-D-glucopyranos-1-yl)-benzene (1.0 g) dissolved in degassed NMP containing 0.1% water (2 mL) is added and the mixture is stirred at room temperature for 18 h. Then, ethyl acetate is added, the resulting mixture is filtered and the filtrate is washed with aqueous NaHCO$_3$ solution. After drying (sodium sulphate) of the organic solution, the solvent is removed under reduced pressure and the residue is dissolved in methanol (10 mL). 4 M aqueous potassium hydroxide solution (2 mL) is added and the solution is stirred at ambient temperature for 1 h. The solution is neutralized with 1 M hydrochloric acid and the methanol is evaporated. The residue is extracted with ethyl acetate, the combined extracts are dried over sodium sulfate and the solvent is removed under reduced pressure. The residue is purified by chromatography on silica gel (dichloromethane/methanol 1:0->4:1).

Yield: 0.51 g (81% of theory)
Mass spectrum (ESI$^+$): m/z=401 [M+NH$_4$]$^+$

Example (6)

2-(4-Cyclopropyl-benzyl)-4-(β-D-glucopyranos-1-yl)-benzonitrile

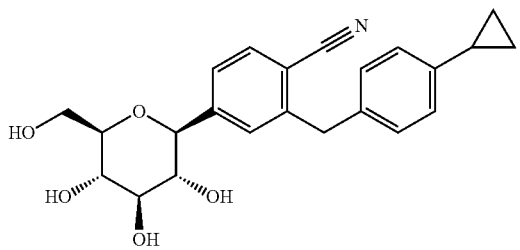 [SMILES: N#Cc1ccc([C@@H]2O[C@H](CO)[C@@H](O)[C@H](O)[C@H]2O)cc1Cc1ccc(C2CC2)cc1]

An Ar filled flask is charged with a stir bar, 2-bromomethyl-4-(2,3,4,6-tetra-O-acetyl-β-D-glucopyranos-1-yl)-benzonitrile (1.78 g), 4-cyclopropyl-phenylboronic acid (1.00 g), potassium carbonate (1.85 g) and a 3:1 mixture of degassed acetone and water (22 mL). The mixture is stirred at room temperature for 5 min, before it is cooled in an ice-bath. Then palladium dichloride (30 mg) is added and the reaction mixture is stirred for 16 h at ambient temperature. The mixture is then diluted with brine and extracted with ethyl acetate. The combined extracts are dried over sodium sulfate and the solvent is removed under reduced pressure. The residue is dissolved in methanol (20 mL) and treated with 4 M aqueous potassium hydroxide solution (3.8 mL). The resulting solution is stirred at ambient temperature for 1 h and then neutralized with 1 M hydrochloric acid. The methanol is evaporated, and the residue is diluted with brine and extracted with ethyl acetate. The organic extracts collected are dried over sodium sulfate, and the solvent is removed. The residue is chromatographed on silica gel (dichloromethane/methanol 1:0->8:1).

Yield: 0.91 g (76% of theory)
Mass spectrum (ESI$^+$): m/z=413 [M+NH$_4$]$^+$

Example (7)

1-chloro-4-(β-D-glucopyranos-1-yl)-2-(4-ethynyl-benzyl)-benzene

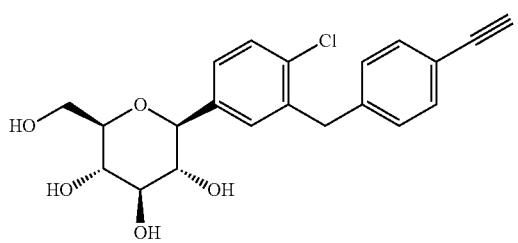 [SMILES: C#Cc1ccc(Cc2cc([C@@H]3O[C@H](CO)[C@@H](O)[C@H](O)[C@H]3O)ccc2Cl)cc1]

The compound (7) can advantageously be prepared according to the example 12 described in the WO 2005/092877.

Example (8)

1-chloro-4-(β-D-glucopyranos-1-yl)-2-[4-((R)-tetrahydrofuran-3-yloxy)-benzyl]-benzene

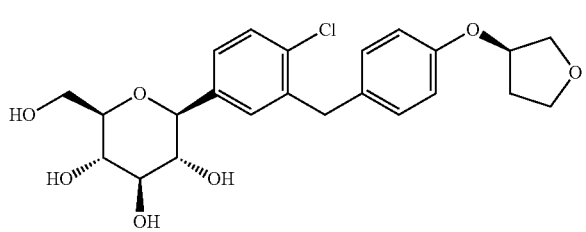 [SMILES: OC[C@H]1O[C@@H](c2ccc(Cl)c(Cc3ccc(O[C@@H]4CCOC4)cc3)c2)[C@H](O)[C@@H](O)[C@@H]1O]

The compound (8) can advantageously be prepared according to the example 2 described in the WO 2005/092877.

Example (9)

1-chloro-4-(β-D-glucopyranos-1-yl)-2-[4-((S)-tetrahydrofuran-3-yloxy)-benzyl]-benzene

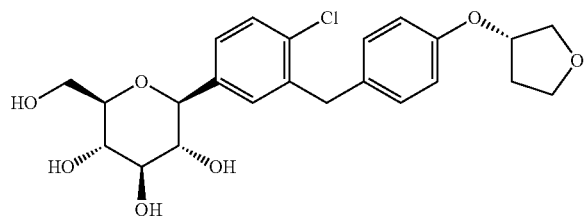 [SMILES: OC[C@H]1O[C@@H](c2ccc(Cl)c(Cc3ccc(O[C@H]4CCOC4)cc3)c2)[C@H](O)[C@@H](O)[C@@H]1O]

The compound (9) can advantageously be prepared according to the example 3 described in the WO 2005/092877.

Example (10)

1-methyl-2-[4-((R)-tetrahydrofuran-3-yloxy)-benzyl]-4-(β-D-glucopyranos-1-yl)-benzene

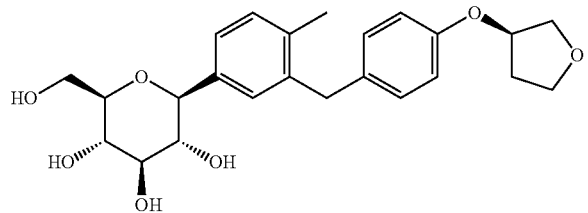 [SMILES: Cc1ccc([C@@H]2O[C@H](CO)[C@@H](O)[C@H](O)[C@H]2O)cc1Cc1ccc(O[C@@H]2CCOC2)cc1]

The compound (10) can advantageously be prepared according to the example 2 described in the WO 2006/064033.

Example (11)

1-methyl-2-[4-((S)-tetrahydrofuran-3-yloxy)-benzyl]-4-(β-D-glucopyranos-1-yl)-benzene

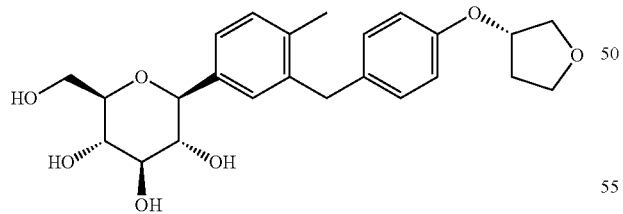

The compound (10) can advantageously be prepared according to the example 3 described in the WO 2006/064033.

PHARMACOLOGICAL EXAMPLES

The following examples show the beneficial effect on glycemic control of the combination of a glucopyranosyl-substituted benzene derivative and a DPP IV inhibitor according to the present invention as compared to the respective monotherapies. All experimental protocols concerning the use of laboratory animals are reviewed by a federal Ethics Committee and approved by governmental authorities.

1st Example

According to a first example an oral glucose tolerance test is performed in overnight fasted 9-weeks old male Zucker Diabetic Fatty (ZDF) rats (ZDF/Crl-Lepr$^{fa}$). A pre-dose blood sample is obtained by tail bleed. Blood glucose is measured with a glucometer, and the animals are randomized for blood glucose (n=5/group). Subsequently, the groups receive a single oral administration of either vehicle alone (0.5% aqueous hydroxyethylcellulose containing 3 mM HCl and 0.015% Polysorbat 80) or vehicle containing either the glucopyranosyl-substituted benzene derivative or the DPP IV inhibitor or the combination of the glucopyranosyl-substituted benzene derivative with the DPP IV inhibitor. The animals receive an oral glucose load (2 g/kg) 30 min after compound administration. Blood glucose is measured in tail blood 30 min, 60 min, 90 min, 120 min, and 180 min after the glucose challenge. Glucose excursion is quantified by calculating the reactive glucose AUC. The data are presented as mean±SEM. The two-sided unpaired Student t-test is used for statistical comparison of the control group and the active groups.

The result is shown in FIG. 1. "Cpd. A" is the DPP IV inhibitor 1-[(4-methyl-quinazolin-2-yl)methyl]-3-methyl-7-(2-butyn-1-yl)-8-(3-(R)-amino-piperidin-1-yl)-xanthine at a dose of 1 mg/kg. Cpd. B is the glucopyranosyl-substituted benzene derivative (9), i.e. 1-chloro-4-(β-D-glucopyranos-1-yl)-2-[4-((S)-tetrahydrofuran-3-yloxy)-benzyl]-benzene, at a dose of 3 mg/kg. Combination A+B is the combination of said DPP IV inhibitor and said glucopyranosyl-substituted benzene derivative at the same doses. P-values versus control are indicated by symbols above the bars. P-values of the combination versus the monotherapies are indicated below the figure (*, p<0.05; , p<0.01; *, p<0.001). The DPP IV inhibitor reduces glucose excursion by 56%, the glucopyranosyl-substituted benzene derivative reduces glucose excursion by 51%. The combination decreased glucose excursion in the oral glucose tolerance test by 84%, and this reduction in glucose AUC is statistically significant versus each monotherapy.

2nd Example

According to a second example an oral glucose tolerance test is performed in overnight fasted male Sprague Dawley rats (Crl:CD(SD)) with a body weight of about 200 g. A pre-dose blood sample is obtained by tail bleed. Blood glucose is measured with a glucometer, and the animals are randomized for blood glucose (n=5/group). Subsequently, the groups receive a single oral administration of either vehicle alone (0.5% aqueous hydroxyethylcellulose containing 0.015% Polysorbat 80) or vehicle containing either the glucopyranosyl-substituted benzene derivative or the DPPIV inhibitor or the combination of the glucopyranosyl-substituted benzene derivative with the DPPIV inhibitor. The animals receive an oral glucose load (2 g/kg) 30 min after compound administration. Blood glucose is measured in tail blood 30 min, 60 min, 90 min, and 120 min after the glucose challenge. Glucose excursion is quantified by calculating the reactive glucose AUC. The data are presented as mean±S.E.M. Statistical comparisons are conducted by Student's t test.

Figure 2:
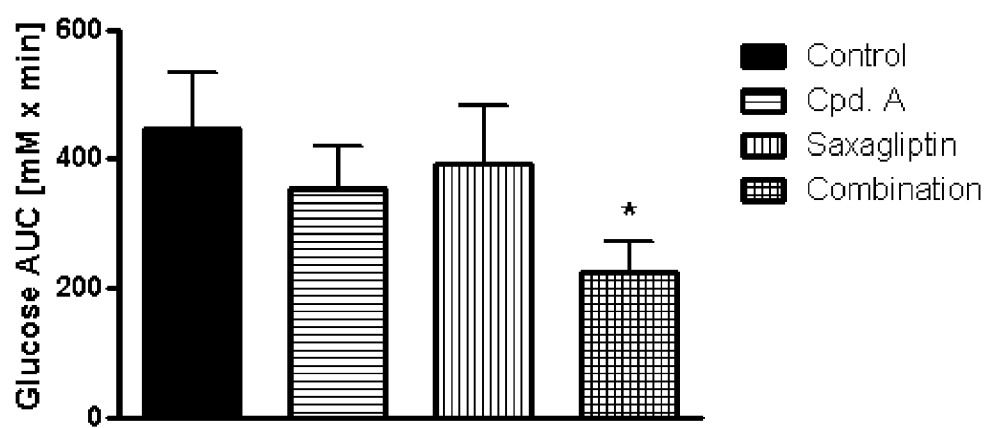

The result is shown in FIG. 2. "Cpd. A" is the glucopyranosyl-substituted benzene derivative (9), i.e. 1-chloro-4-(β-D-glucopyranos-1-yl)-2-[4-((S)-tetrahydrofuran-3-yloxy)-benzyl]-benzene, administered at a dose of 3 mg/kg. The DPPIV inhibitor saxagliptin is administered at a dose of 0.3 mg/kg. In the combination, the glucopyranosyl-substituted benzene derivative and saxagliptin are administered together at the same doses as in the respective monotherapies. P values versus control are indicated by symbols above the bars. (*, p<0.05). The glucopyranosyl-substituted benzene derivative and saxagliptin reduces glucose excursion by 21% and 12%, respectively, albeit the reduction is not statistically significant in these non-diabetic animals. The combination decreases glucose excursion in the oral glucose tolerance test by 50%, and this reduction in glucose AUC is statistically significant.

3$^{rd}$ Example

Figure 3:
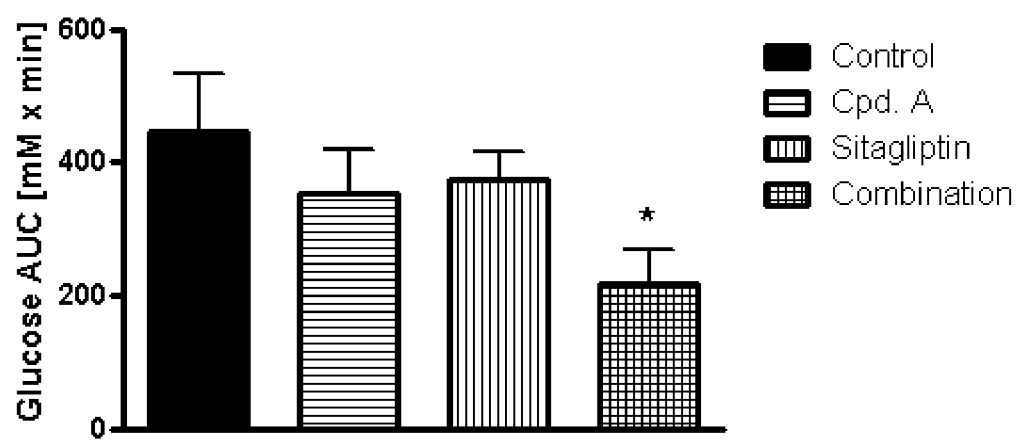

In a third example the same experimental setting is employed as in the second example as described herein before. The glucopyranosyl-substituted benzene derivative (9), i.e. 1-chloro-4-(β-D-glucopyranos-1-yl)-2-[4-((S)-tetrahydrofuran-3-yloxy)-benzyl]-benzene, is administered at a dose of 3 mg/kg. The DPPIV inhibitor sitagliptin is administered at a dose of 10 mg/kg. In the combination, the glucopyranosyl-substituted benzene derivative and sitagliptin are administered together at the same doses as in the respective monotherapies. The result is shown in the FIG. 3 wherein "Cpd. A" is said glucopyranosyl-substituted benzene derivative (9). P values versus control are indicated by symbols above the bars. (*, p<0.05). The glucopyranosyl-substituted benzene derivative and sitagliptin reduces glucose excursion by 21% and 16%, respectively, albeit the reduction is not statistically significant in these non-diabetic animals. The combination decreases glucose excursion in the oral glucose tolerance test by 51%, and this reduction in glucose AUC is statistically significant.

EXAMPLES OF FORMULATIONS

The following examples of formulations, which may be obtained analogously to methods known in the art, serve to illustrate the present invention more fully without restricting it to the contents of these examples. The term "active substance" denotes one or more compounds according to the invention, i.e. denotes a glucopyranosyl-substituted benzene derivative according to this invention or a DPP IV inhibitor according to this invention or a combination of said glucopyranosyl-substituted benzene derivative with said DPP IV inhibitor, for example selected from the combinations 1 to 176 as listed in Table 1. Additional suitable formulations for the DPP IV inhibitors of embodiment A may be those formulations disclosed in the application WO 2007/128724, the disclosure of which is incorporated herein in its entirety. Additional suitable formulations for the DPP IV inhibitors of embodiment B may be those formulations which are available on the market, or formulations described in the patent applications cited above in paragraph "background of the invention", or those described in the literature, for example as disclosed in current issues of "Rote Liste®" (Editio Cantor Verlag Aulendorf, Germany) or of "Physician's Desk Reference".

Example 1

Dry Ampoule Containing 75 mg of Active Substance Per 10 ml

Composition:
Active substance 75.0 mg
Mannitol 50.0 mg
water for injections ad 10.0 ml
Preparation:
Active substance and mannitol are dissolved in water. After packaging the solution is freeze-dried. To produce the solution ready for use, the product is dissolved in water for injections.

Example 2

Dry Ampoule Containing 35 mg of Active Substance Per 2 ml

Composition:
Active substance 35.0 mg
Mannitol 100.0 mg
water for injections ad 2.0 ml
Preparation:
Active substance and mannitol are dissolved in water. After packaging, the solution is freeze-dried.
To produce the solution ready for use, the product is dissolved in water for injections.

Example 3

Tablet Containing 50 mg of Active Substance

Composition:
(1) Active substance 50.0 mg
(2) Lactose 98.0 mg
(3) Maize starch 50.0 mg
(4) Polyvinylpyrrolidone 15.0 mg
(5) Magnesium stearate 2.0 mg
    215.0 mg
Preparation:
(1), (2) and (3) are mixed together and granulated with an aqueous solution of (4). (5) is added to the dried granulated material. From this mixture tablets are pressed, biplanar, faceted on both sides and with a dividing notch on one side.
Diameter of the tablets: 9 mm.

Example 4

Tablet Containing 350 mg of Active Substance

Preparation:
(1) Active substance 350.0 mg
(2) Lactose 136.0 mg
(3) Maize starch 80.0 mg
(4) Polyvinylpyrrolidone 30.0 mg
(5) Magnesium stearate 4.0 mg
    600.0 mg
(1), (2) and (3) are mixed together and granulated with an aqueous solution of (4). (5) is added to the dried granulated material. From this mixture tablets are pressed, biplanar, faceted on both sides and with a dividing notch on one side.
Diameter of the tablets: 12 mm.

Example 5

Capsules Containing 50 mg of Active Substance

Composition:
(1) Active substance 50.0 mg
(2) Dried maize starch 58.0 mg
(3) Powdered lactose 50.0 mg
(4) Magnesium stearate 2.0 mg
  160.0 mg Preparation:

(1) is triturated with (3). This trituration is added to the mixture of (2) and (4) with vigorous mixing. This powder mixture is packed into size 3 hard gelatin capsules in a capsule filling machine.

Example 6

Capsules Containing 350 mg of Active Substance

Composition:
(1) Active substance 350.0 mg
(2) Dried maize starch 46.0 mg
(3) Powdered lactose 30.0 mg
(4) Magnesium stearate 4.0 mg
  430.0 mg Preparation:

(1) is triturated with (3). This trituration is added to the mixture of (2) and (4) with vigorous mixing. This powder mixture is packed into size 0 hard gelatin capsules in a capsule filling machine.

The invention claimed is:

1. A phamaceutical composition comprising the glucopyranosyl-substituted benzene derivative 1-chloro-4-(β-D-glucopyranos-1-yl)-2-[4-((S)-tetrahydrofuran-3-yloxy)-benzyl]-benzene in combination with the DPP IV inhibitor 1-[(4-methyl-quinazolin-2-yl)methyl]-3-methyl-7-(2-butyn-1-yl)-8-(3-(R)-amino-piperidin-1-yl)-xanthine, or a pharmaceutically acceptable salt thereof.

2. The pharmaceutical composition according to claim 1, wherein the glucopyranosyl-substituted benzene derivative and the DPP IV inhibitor are present in a single dosage form.

3. The pharmaceutical composition according to claim 1, wherein the glucopyranosyl-substituted benzene derivative and the DPP IV inhibitor are present each in a separate dosage form.

4. Method for slowing the progression of, delaying or treating a metabolic disorder selected from the group consisting of type 1 diabetes mellitus, type 2 diabetes mellitus, impaired glucose tolerance, impaired fasting blood glucose, hyperglycemia, postprandial hyperglycemia, overweight, obesity and metabolic syndrome in a patient in need thereof comprising administering to the patient the glucopyranosyl-substituted benzene derivative according to claim 1 in combination or alternation with the DPP IV inhibitor according to claim 1.

5. Method for improving glycemic control and/or for reducing of fasting plasma glucose, of postprandial plasma glucose and/or of glycosylated hemoglobin HbA1c in a patient in need thereof comprising administering to the patient the glucopyranosyl-substituted benzene derivative according to claim 1 in combination or alternation with the DPP IV inhibitor according to claim 1.

6. Method for slowing, delaying or reversing progression from impaired glucose tolerance, impaired fasting blood glucose, insulin resistance and/or from metabolic syndrome to type 2 diabetes mellitus in a patient in need thereof comprising administering to the patient the glucopyranosyl-substituted benzene derivative according to claim 1 in combination or alternation with a DPP IV inhibitor according to claim 1.

7. Method for slowing the progression of, or delaying a condition or disorder selected from the group consisting of complications of diabetes mellitus consisting of cataracts and micro- and macrovascular diseases consisting of nephropathy, retinopathy, neuropathy, tissue ischaemia, arteriosclerosis, myocardial infarction, stroke and peripheral arterial occlusive disease, in a patient in need thereof comprising administering to the patient the glucopyranosyl-substituted benzene derivative according to claim 1 in combination or alternation with a DPP IV inhibitor according to claim 1.

8. Method for reducing body weight or facilitating a reduction in body weight in a patient in need thereof comprising administering to the patient the glucopyranosyl-substituted benzene derivative according to claim 1 in combination or alternation with a DPP IV inhibitor according to claim 1.

9. Method for slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion in a patient in need thereof comprising administering to the patient the glucopyranosyl-substituted benzene derivative according to claim 1 in combination or alternation with a DPP IV inhibitor according to claim 1.

10. Method for slowing, delaying or treating diseases or conditions attributed to an abnormal accumulation of liver fat in a patient in need thereof comprising administering to the patient the glucopyranosyl-substituted benzene derivative according to claim 1 in combination or alternation with a DPP IV inhibitor according to claim 1.

11. Method for maintaining and/or improving the insulin sensitivity and/or for treating hyperinsulinemia and/or insulin resistance in a patient in need thereof comprising administering to the patient the glucopyranosyl-substituted benzene derivative according to claim 1 in combination or alternation with a DPP IV inhibitor according to claim 1.

12. Method according to claim 4 wherein the patient is:
  (1) an individual diagnosed of one or more of the conditions selected from the group consisting of overweight, obesity, visceral obesity and abdominal obesity; or
  (2) an individual who shows one, two or more of the following conditions:
    (a) a fasting blood glucose or serum glucose concentration greater than 110 mg/dL, in particular greater than 125 mg/dL;
    (b) a postprandial plasma glucose equal to or greater than 140 mg/dL;
    (c) an HbA1c value equal to or greater than 6.5%, in particular equal to or greater than 8.0%; or
  (3) an individual wherein one, two, three or more of the following conditions are present:
    (a) obesity, visceral obesity and/or abdominal obesity,
    (b) triglyceride blood level ≥150 mg/dL,
    (c) HDL-cholesterol blood level <40 mg/dL in female patients and <50 mg/dL in male patients,
    (d) a systolic blood pressure ≥130 mm Hg and a diastolic blood pressure ≥85 mm Hg,
    (e) a fasting blood glucose level ≥110 mg/dL; or
  (4) an individual for whom the monotherapy with metformin is contraindicated and/or who has an intolerance against metformin at therapeutic doses; or
  (5) an individual with insufficient glycemic control despite monotherapy with a SGLT2 inhibitor; or (6) an individual with insufficient glycemic control despite monotherapy with a DPP IV inhibitor.

13. Method according to claim 5 wherein the patient is:
(1) an individual diagnosed of one or more of the conditions selected from the group consisting of overweight, obesity, visceral obesity and abdominal obesity; or
(2) an individual who shows one, two or more of the following conditions:
(a) a fasting blood glucose or serum glucose concentration greater than 110 mg/dL, in particular greater than 125 mg/dL;
(b) a postprandial plasma glucose equal to or greater than 140 mg/dL;
(c) an HbA1c value equal to or greater than 6.5%, in particular equal to or greater than 8.0%; or
(3) an individual wherein one, two, three or more of the following conditions are present:
(a) obesity, visceral obesity and/or abdominal obesity,
(b) triglyceride blood level ≥150 mg/dL,
(c) HDL-cholesterol blood level <40 mg/dL in female patients and <50 mg/dL in male patients,
(d) a systolic blood pressure ≥130 mm Hg and a diastolic blood pressure ≥85 mm Hg,
(e) a fasting blood glucose level ≥110 mg/dL; or
(4) an individual for whom the monotherapy with metformin is contraindicated and/or who has an intolerance against metformin at therapeutic doses; or
(5) an individual with insufficient glycemic control despite monotherapy with a SGLT2 inhibitor; or
(6) an individual with insufficient glycemic control despite monotherapy with a DPP IV inhibitor.

14. Method according to claim 6 wherein the patient is:
(1) an individual diagnosed of one or more of the conditions selected from the group consisting of overweight, obesity, visceral obesity and abdominal obesity; or
(2) an individual who shows one, two or more of the following conditions:
(a) a fasting blood glucose or serum glucose concentration greater than 110 mg/dL, in particular greater than 125 mg/dL;
(b) a postprandial plasma glucose equal to or greater than 140 mg/dL;
(c) an HbA1c value equal to or greater than 6.5%, in particular equal to or greater than 8.0%; or
(3) an individual wherein one, two, three or more of the following conditions are present:
(a) obesity, visceral obesity and/or abdominal obesity,
(b) triglyceride blood level ≥150 mg/dL,
(c) HDL-cholesterol blood level <40 mg/dL in female patients and <50 mg/dL in male patients,
(d) a systolic blood pressure ≥130 mm Hg and a diastolic blood pressure ≥85 mm Hg,
(e) a fasting blood glucose level ≥110 mg/dL; or
(4) an individual for whom the monotherapy with metformin is contraindicated and/or who has an intolerance against metformin at therapeutic doses; or
(5) an individual with insufficient glycemic control despite monotherapy with a SGLT2 inhibitor; or
(6) an individual with insufficient glycemic control despite monotherapy with a DPP IV inhibitor.

15. Method according to claim 7 wherein the patient is:
(1) an individual diagnosed of one or more of the conditions selected from the group consisting of overweight, obesity, visceral obesity and abdominal obesity; or
(2) an individual who shows one, two or more of the following conditions:
(a) a fasting blood glucose or serum glucose concentration greater than 110 mg/dL, in particular greater than 125 mg/dL;
(b) a postprandial plasma glucose equal to or greater than 140 mg/dL;
(c) an HbA1c value equal to or greater than 6.5%, in particular equal to or greater than 8.0%; or
(3) an individual wherein one, two, three or more of the following conditions are present:
(a) obesity, visceral obesity and/or abdominal obesity,
(b) triglyceride blood level ≥150 mg/dL,
(c) HDL-cholesterol blood level <40 mg/dL in female patients and <50 mg/dL in male patients,
(d) a systolic blood pressure ≥130 mm Hg and a diastolic blood pressure ≥85 mm Hg,
(e) a fasting blood glucose level ≥110 mg/dL; or
(4) an individual for whom the monotherapy with metformin is contraindicated and/or who has an intolerance against metformin at therapeutic doses; or
(5) an individual with insufficient glycemic control despite monotherapy with a SGLT2 inhibitor; or
(6) an individual with insufficient glycemic control despite monotherapy with a DPP IV inhibitor.

16. Method according to claim 8 wherein the patient is:
(1) an individual diagnosed of one or more of the conditions selected from the group consisting of overweight, obesity, visceral obesity and abdominal obesity; or
(2) an individual who shows one, two or more of the following conditions:
(a) a fasting blood glucose or serum glucose concentration greater than 110 mg/dL, in particular greater than 125 mg/dL;
(b) a postprandial plasma glucose equal to or greater than 140 mg/dL;
(c) an HbA1c value equal to or greater than 6.5%, in particular equal to or greater than 8.0%; or
(3) an individual wherein one, two, three or more of the following conditions are present:
(a) obesity, visceral obesity and/or abdominal obesity,
(b) triglyceride blood level ≥150 mg/dL,
(c) HDL-cholesterol blood level <40 mg/dL in female patients and <50 mg/dL in male patients,
(d) a systolic blood pressure ≥130 mm Hg and a diastolic blood pressure ≥85 mm Hg,
(e) a fasting blood glucose level ≥110 mg/dL; or
(4) an individual for whom the monotherapy with metformin is contraindicated and/or who has an intolerance against metformin at therapeutic doses; or
(5) an individual with insufficient glycemic control despite monotherapy with a SGLT2 inhibitor; or
(6) an individual with insufficient glycemic control despite monotherapy with a DPP IV inhibitor.

17. Method according to claim 9 wherein the patient is:
(1) an individual diagnosed of one or more of the conditions selected from the group consisting of overweight, obesity, visceral obesity and abdominal obesity; or
(2) an individual who shows one, two or more of the following conditions:
(a) a fasting blood glucose or serum glucose concentration greater than 110 mg/dL, in particular greater than 125 mg/dL;
(b) a postprandial plasma glucose equal to or greater than 140 mg/dL;
(c) an HbA1c value equal to or greater than 6.5%, in particular equal to or greater than 8.0%; or
(3) an individual wherein one, two, three or more of the following conditions are present:

(a) obesity, visceral obesity and/or abdominal obesity,
(b) triglyceride blood level ≥150 mg/dL,
(c) HDL-cholesterol blood level <40 mg/dL in female patients and <50 mg/dL in male patients,
(d) a systolic blood pressure ≥130 mm Hg and a diastolic blood pressure ≥85 mm Hg,
(e) a fasting blood glucose level ≥110 mg/dL; or
(4) an individual for whom the monotherapy with metformin is contraindicated and/or who has an intolerance against metformin at therapeutic doses; or
(5) an individual with insufficient glycemic control despite monotherapy with a SGLT2 inhibitor; or
(6) an individual with insufficient glycemic control despite monotherapy with a DPP IV inhibitor.

18. Method according to claim 10 wherein the patient is:
(1) an individual diagnosed of one or more of the conditions selected from the group consisting of overweight, obesity, visceral obesity and abdominal obesity; or
(2) an individual who shows one, two or more of the following conditions:
(a) a fasting blood glucose or serum glucose concentration greater than 110 mg/dL, in particular greater than 125 mg/dL;
(b) a postprandial plasma glucose equal to or greater than 140 mg/dL;
(c) an HbA1c value equal to or greater than 6.5%, in particular equal to or greater than 8.0%; or
(3) an individual wherein one, two, three or more of the following conditions are present:
(a) obesity, visceral obesity and/or abdominal obesity,
(b) triglyceride blood level ≥150 mg/dL,
(c) HDL-cholesterol blood level <40 mg/dL in female patients and <50 mg/dL in male patients,
(d) a systolic blood pressure ≥130 mm Hg and a diastolic blood pressure ≥85 mm Hg,
(e) a fasting blood glucose level ≥110 mg/dL; or
(4) an individual for whom the monotherapy with metformin is contraindicated and/or who has an intolerance against metformin at therapeutic doses; or
(5) an individual with insufficient glycemic control despite monotherapy with a SGLT2 inhibitor; or
(6) an individual with insufficient glycemic control despite monotherapy with a DPP IV inhibitor.

19. Method according to claim 11 wherein the patient is:
(1) an individual diagnosed of one or more of the conditions selected from the group consisting of overweight, obesity, visceral obesity and abdominal obesity; or
(2) an individual who shows one, two or more of the following conditions:
(a) a fasting blood glucose or serum glucose concentration greater than 110 mg/dL, in particular greater than 125 mg/dL;
(b) a postprandial plasma glucose equal to or greater than 140 mg/dL;
(c) an HbA1c value equal to or greater than 6.5%, in particular equal to or greater than 8.0%; or
(3) an individual wherein one, two, three or more of the following conditions are present:
(a) obesity, visceral obesity and/or abdominal obesity,
(b) triglyceride blood level ≥150 mg/dL,
(c) HDL-cholesterol blood level <40 mg/dL in female patients and <50 mg/dL in male patients,
(d) a systolic blood pressure ≥130 mm Hg and a diastolic blood pressure ≥85 mm Hg,
(e) a fasting blood glucose level ≥110 mg/dL; or
(4) an individual for whom the monotherapy with metformin is contraindicated and/or who has an intolerance against metformin at therapeutic doses; or
(5) an individual with insufficient glycemic control despite monotherapy with a SGLT2 inhibitor; or
(6) an individual with insufficient glycemic control despite monotherapy with a DPP IV inhibitor.

20. The pharmaceutical composition according to claim 1, wherein said pharmaceutical composition is formulated for oral administration.

21. The pharmaceutical composition according to claim 1, wherein said pharmaceutical composition is formulated for oral administration in solid form.

22. The pharmaceutical composition according to claim 1, wherein said pharmaceutical composition comprises an amount of 5 to 50 mg of the glucopyranosyl-substituted benzene derivative.

23. The pharmaceutical composition according to claim 1, wherein said pharmaceutical composition comprises an amount of 0.5 to 10 mg of the DPP IV inhibitor.

24. The pharmaceutical composition according to claim 1, wherein said pharmaceutical composition comprises an amount of 5 to 50 mg of the glucopyranosyl-substituted benzene derivative and an amount of 0.5 to 10 mg of the DPP IV inhibitor.

25. Method for treating type 2 diabetes mellitus in a patient in need thereof comprising administering to the patient the glucopyranosyl-substituted benzene derivative according to claim 1 in combination or alternation with the DPP IV inhibitor according to claim 1.

26. Method according to claim 25, wherein the glucopyranosyl-substituted benzene derivative is administered in an amount of 0.5 to 50 mg once daily.

27. Method according to claim 25, wherein the DPP IV inhibitor is administered in an amount of 0.5 to 10 mg once daily.

28. Method according to claim 25, wherein the glucopyranosyl-substituted benzene derivative is administered in an amount of 0.5 to 50 mg once daily and the DPP IV inhibitor is administered in an amount of 0.5 to 10 mg once daily.

29. Method according to claim 25, wherein the glucopyranosyl-substituted benzene derivative and the DPP IV inhibitor are present in a single dosage form.

30. Method according to claim 29, wherein the single dosage form is administered orally.

31. The pharmaceutical composition according to claim 22, wherein said pharmaceutical composition comprises an amount of 5 mg, 10 mg, 15 mg, 20 mg, 25 mg or 50 mg of the glucopyranosyl-substituted benzene derivative.

32. The pharmaceutical composition according to claim 22, wherein said pharmaceutical composition comprises an amount of 10 mg of the glucopyranosyl-substituted benzene derivative.

33. The pharmaceutical composition according to claim 22, wherein said pharmaceutical composition comprises an amount of 25 mg of the glucopyranosyl-substituted benzene derivative.

34. The pharmaceutical composition according to claim 23, wherein said pharmaceutical composition comprises an amount of 0.5 mg, 1 mg, 2.5 mg, 5 mg or 10 mg of the DPP IV inhibitor.

35. The pharmaceutical composition according to claim 23, wherein said pharmaceutical composition comprises an amount of 1 mg, 2.5 mg or 5 mg of the DPP IV inhibitor.

36. The pharmaceutical composition according to claim 23, wherein said pharmaceutical composition comprises an amount of 5 mg of the DPP IV inhibitor.

37. A pharmaceutical composition comprising the glucopyranosyl-substituted benzene derivative 1-chloro-4-(β-D-glucopyranos-1-yl)-2-[4-((S)-tetrahydrofuran-3-yloxy)-benzyl]-benzene in combination with the DPP IV inhibitor 1-[(4-methyl-quinazolin-2-yl)methyl]-3-methyl-7-(2-butyn-1-yl)-8-(3-(R)-amino-piperidin-1-yl)-xanthine, or a pharmaceutically acceptable salt thereof, wherein said pharmaceutical composition comprises an amount of 10 mg of the glucopyranosyl-substituted benzene derivative and an amount of 5 mg of the DPP IV inhibitor.

38. A pharmaceutical composition comprising the glucopyranosyl-substituted benzene derivative 1-chloro-4-(β-D-glucopyranos-1-yl)-2-[4-((S)-tetrahydrofuran-3-yloxy)-benzyl]-benzene in combination with the DPP IV inhibitor 1-[(4-methyl-quinazolin-2-yl)methyl]-3-methyl-7-(2-butyn-1-yl)-8-(3-(R)-amino-piperidin-1-yl)-xanthine, or a pharmaceutically acceptable salt thereof, wherein said pharmaceutical composition comprises an amount of 10 mg of the glucopyranosyl-substituted benzene derivative and an amount of 5 mg of the DPP IV inhibitor, wherein the glucopyranosyl-substituted benzene derivative and the DPP IV inhibitor are present in a single dosage form.

39. A pharmaceutical composition comprising the glucopyranosyl-substituted benzene derivative 1-chloro-4-(β-D-glucopyranos-1-yl)-2-[4-((S)-tetrahydrofuran-3-yloxy)-benzyl]-benzene in combination with the DPP IV inhibitor 1-[(4-methyl-quinazolin-2-yl)methyl]-3-methyl-7-(2-butyn-1-yl)-8-(3-(R)-amino-piperidin-1-yl)-xanthine, or a pharmaceutically acceptable salt thereof, wherein said pharmaceutical composition comprises an amount of 25 mg of the glucopyranosyl-substituted benzene derivative and an amount of 5 mg of the DPP IV inhibitor.

40. A pharmaceutical composition comprising the glucopyranosyl-substituted benzene derivative 1-chloro-4-(β-D-glucopyranos-1-yl)-2-[4-((S)-tetrahydrofuran-3-yloxy)-benzyl]-benzene in combination with the DPP IV inhibitor 1-[(4-methyl-quinazolin-2-yl)methyl]-3-methyl-7-(2-butyn-1-yl)-8-(3-(R)-amino-piperidin-1-yl)-xanthine, or a pharmaceutically acceptable salt thereof, wherein said pharmaceutical composition comprises an amount of 25 mg of the glucopyranosyl-substituted benzene derivative and an amount of 5 mg of the DPP IV inhibitor, wherein the glucopyranosyl-substituted benzene derivative and the DPP IV inhibitor are present in a single dosage form.

41. The method according to claim 26, wherein the glucopyranosyl-substituted benzene derivative is administered in an amount of 5 mg, 10 mg, 15 mg, 20 mg, 25 mg or 50 mg once daily.

42. The method according to claim 26, wherein the glucopyranosyl-substituted benzene derivative is administered in an amount of 10 mg once daily.

43. The method according to claim 26, wherein the glucopyranosyl-substituted benzene derivative is administered in an amount of 25 mg once daily.

44. The method according to claim 27, wherein the DPP IV inhibitor is administered in an amount of 0.5 mg, 1 mg, 2.5 mg, 5 mg or 10 mg once daily.

45. The method according to claim 27, wherein the DPP IV inhibitor is administered in an amount of 1 mg, 2.5 mg or 5 mg once daily.

46. The method according to claim 27, wherein the DPP IV inhibitor is administered in an amount of 5 mg once daily.

47. The method according to claim 28, wherein the glucopyranosyl-substituted benzene derivative is administered in an amount of 10 mg once daily and the DPP IV inhibitor is administered in an amount of 5 mg once daily.

48. The method according to claim 28, wherein the glucopyranosyl-substituted benzene derivative is administered in an amount of 25 mg once daily and the DPP IV inhibitor is administered in an amount of 5 mg once daily.

* * * * *

UNITED STATES PATENT AND TRADEMARK OFFICE
CERTIFICATE OF CORRECTION

PATENT NO. : 8,551,957 B2  Page 1 of 1
APPLICATION NO. : 12/673327
DATED : October 8, 2013
INVENTOR(S) : Klaus Dugi et al.

It is certified that error appears in the above-identified patent and that said Letters Patent is hereby corrected as shown below:

In the Claims

In Column fifty-three (53), line thirty-four (34), in Claim 1, please change "62" to --β--.

Signed and Sealed this
Twelfth Day of May, 2015

Michelle K. Lee
*Director of the United States Patent and Trademark Office*